(12) United States Patent
Desouza et al.

(10) Patent No.: US 11,607,482 B2
(45) Date of Patent: Mar. 21, 2023

(54) FLOW BALANCING DEVICES, METHODS, AND SYSTEMS

(71) Applicant: NxStage Medical, Inc., Lawrence, MA (US)

(72) Inventors: David Desouza, Essex, MA (US); Daniel Joseph Rubery, Jr., Nashua, NH (US); Dennis M. Treu, Castle Rock, CO (US); Mark T. Wyeth, Andover, MA (US); Jerome James, Vestavia, AL (US); Garrett D. Casey, Methuen, MA (US); James M. Brugger, Newburyport, MA (US); William J. Schnell, Libertyville, IL (US); Jeffrey H. Burbank, Manchester, MA (US); Goetz Friederichs, Beverly, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 17/122,772

(22) Filed: Dec. 15, 2020

(65) Prior Publication Data

US 2021/0128812 A1 May 6, 2021

Related U.S. Application Data

(63) Continuation of application No. 16/317,903, filed as application No. PCT/US2017/042683 on Jul. 18, 2017, now Pat. No. 10,898,635.

(Continued)

(51) Int. Cl.
*A61M 1/36* (2006.01)
*A61M 1/16* (2006.01)

(52) U.S. Cl.
CPC ........ *A61M 1/3663* (2013.01); *A61M 1/1601* (2014.02); *A61M 1/1647* (2014.02);
(Continued)

(58) Field of Classification Search
CPC .............. A61M 1/1601; A61M 1/1635; A61M 1/1647; A61M 1/3607; A61M 1/3663; A61M 2205/3334; A61M 2205/3393
See application file for complete search history.

(56) References Cited

U.S. PATENT DOCUMENTS 4,009,078 A 2/1977 Wilkins et al.
4,728,433 A 3/1988 Buck et al.
(Continued)

FOREIGN PATENT DOCUMENTS

EP 2163271 B1 3/2010
EP 2279768 A1 2/2011
(Continued)

OTHER PUBLICATIONS

Extended European Search Report dated Feb. 3, 2020 for European Patent Application No. 17831728.5.
(Continued)

*Primary Examiner* — Terry K Cecil
(74) *Attorney, Agent, or Firm* — Potomac Law Group, PLLC; Brian Hairston

(57) ABSTRACT

The disclosed subject matter relates to extracorporeal blood processing or other processing of fluids. Volumetric fluid balance, a required element of many such processes, may be achieved with multiple pumps or other proportioning or balancing devices which are to some extent independent of each other. This need may arise in treatments that involve multiple fluids. Safe and secure mechanisms to ensure fluid balance in such systems are described.

20 Claims, 27 Drawing Sheets

Related U.S. Application Data

(60) Provisional application No. 62/524,518, filed on Jun. 24, 2017, provisional application No. 62/363,394, filed on Jul. 18, 2016.

(52) U.S. Cl.
CPC ... *A61M 1/3607* (2014.02); *A61M 2205/3334* (2013.01); *A61M 2205/3393* (2013.01)

(56) References Cited

U.S. PATENT DOCUMENTS

| | | |
|---|---|---|
| 4,769,001 A | 9/1988 | Prince |
| 4,894,150 A | 1/1990 | Schurek et al. |
| 5,344,568 A | 9/1994 | Kitaevich et al. |
| 5,792,367 A | 8/1998 | Mattisson et al. |
| 5,836,908 A | 11/1998 | Beden et al. |
| 5,932,103 A | 8/1999 | Kenley et al. |
| 5,984,893 A | 11/1999 | Ward |
| 6,217,539 B1 | 4/2001 | Goldau |
| 6,221,672 B1 | 4/2001 | Baugh et al. |
| 6,284,131 B1 | 9/2001 | Hogard et al. |
| 7,112,273 B2 | 9/2006 | Weigel et al. |
| 7,341,568 B2 | 3/2008 | Zhang |
| 7,699,992 B2 | 4/2010 | Sternby |
| 7,727,222 B2 | 6/2010 | Silva et al. |
| 7,931,610 B2 | 4/2011 | Murakami et al. |
| 8,012,114 B2 | 9/2011 | Daniel et al. |
| 8,060,190 B2 | 11/2011 | Sömmo et al. |
| 8,086,323 B2 | 12/2011 | Reghabi et al. |
| 8,092,414 B2 | 1/2012 | Schnell et al. |
| 8,182,692 B2 | 5/2012 | Gotch |
| 8,209,033 B2 | 6/2012 | Zhang et al. |
| 8,216,478 B2 | 7/2012 | Noack et al. |
| 8,239,010 B2 | 8/2012 | Banet et al. |
| 8,246,546 B2 | 8/2012 | Huiku |
| 8,246,567 B2 | 8/2012 | Bene |
| 8,287,739 B2 | 10/2012 | Barrett |
| 8,361,006 B2 | 1/2013 | Kraemer |
| 8,524,154 B2 | 9/2013 | Shekalim et al. |
| 8,529,767 B2 | 9/2013 | Zhang |
| 8,583,226 B2 | 11/2013 | Moissl et al. |
| 8,591,865 B2 | 11/2013 | Wang et al. |
| 8,613,705 B2 | 12/2013 | Scheurer et al. |
| 8,632,485 B2 | 1/2014 | Schlaeper et al. |
| 8,663,931 B2 | 3/2014 | Saito et al. |
| 8,792,089 B2 | 7/2014 | Zhang et al. |
| 8,858,486 B2 | 10/2014 | Zhang et al. |
| 8,900,172 B2 | 12/2014 | Pohlmeier |
| 9,037,207 B2 | 5/2015 | Al-Ali et al. |
| 9,144,639 B2 | 9/2015 | Vantard et al. |
| 9,220,827 B2 | 12/2015 | Meibaum et al. |
| 9,278,171 B2 | 3/2016 | Brandl et al. |
| 9,381,289 B2 | 7/2016 | Hedmann et al. |
| 9,423,338 B2 | 8/2016 | Alic et al. |
| 9,566,377 B2 | 2/2017 | Jones et al. |
| 9,610,393 B2 | 4/2017 | Rada et al. |
| 9,724,455 B2 | 8/2017 | Kopperschmidt et al. |
| 9,743,843 B2 | 8/2017 | Chamney et al. |
| 9,795,739 B2 | 10/2017 | Al-Ali et al. |
| 9,814,412 B2 | 11/2017 | Zhang et al. |
| 9,943,633 B2 | 4/2018 | Sigg et al. |
| 9,968,298 B2 | 5/2018 | Heppe et al. |
| 9,980,663 B2 | 5/2018 | Wabel et al. |
| 9,987,406 B2 | 6/2018 | Wright et al. |
| 10,001,454 B2 | 6/2018 | Schick et al. |
| 10,010,289 B2 | 7/2018 | Gagel et al. |
| 10,016,549 B2 | 7/2018 | Stonger et al. |
| 10,092,249 B2 | 10/2018 | Kiani et al. |
| 10,117,590 B2 | 11/2018 | Barrett et al. |
| 10,155,077 B2 | 12/2018 | Maierhofer et al. |
| 10,328,192 B2 | 6/2019 | Jansson et al. |
| 2001/0016699 A1 | 8/2001 | Burbank et al. |
| 2003/0113933 A1 | 6/2003 | Jansson et al. |
| 2004/0245161 A1 | 12/2004 | Treu et al. |
| 2005/0113735 A1 | 5/2005 | Brugger et al. |
| 2005/0126961 A1 | 6/2005 | Bissler et al. |
| 2005/0133735 A1 | 6/2005 | Tatsumi et al. |
| 2005/0251086 A1 | 11/2005 | Sternby |
| 2009/0076434 A1 | 3/2009 | Mischelevich et al. |
| 2009/0078622 A1 | 3/2009 | Zhang et al. |
| 2010/0016777 A1 | 1/2010 | Burbank et al. |
| 2010/0099958 A1 | 4/2010 | Kotanko et al. |
| 2010/0112583 A1 | 5/2010 | Ichiishi et al. |
| 2010/0137693 A1 | 6/2010 | Porras et al. |
| 2010/0247377 A1 | 9/2010 | Tsutsumida et al. |
| 2010/0298751 A1 | 11/2010 | Schulte et al. |
| 2011/0000830 A1 | 1/2011 | Ikeda |
| 2011/0066043 A1 | 3/2011 | Banet et al. |
| 2011/0077474 A1 | 3/2011 | Huiku |
| 2011/0132838 A1 | 6/2011 | Curtis et al. |
| 2011/0208072 A1 | 8/2011 | Pfeiffer et al. |
| 2011/0230744 A1 | 9/2011 | Ripoll et al. |
| 2012/0118801 A1 | 5/2012 | Rada et al. |
| 2012/0150049 A1 | 6/2012 | Zielinski et al. |
| 2012/0181189 A1 | 7/2012 | Merchant |
| 2012/0203573 A1 | 8/2012 | Mayer et al. |
| 2012/0228226 A1 | 9/2012 | Castellarnau et al. |
| 2012/0232364 A1 | 9/2012 | Delmage |
| 2012/0310135 A1 | 12/2012 | Bauer et al. |
| 2012/0316465 A1 | 12/2012 | Maier et al. |
| 2013/0134077 A1 | 5/2013 | Wieskotten et al. |
| 2013/0153474 A1 | 6/2013 | Frorip et al. |
| 2013/0280104 A1 | 10/2013 | Heide et al. |
| 2014/0012097 A1 | 1/2014 | McCrea et al. |
| 2014/0224736 A1 | 8/2014 | Heide et al. |
| 2015/0005699 A1 | 1/2015 | Burbank et al. |
| 2015/0100009 A1 | 4/2015 | Bearss |
| 2015/0133854 A1 | 5/2015 | Zhu et al. |
| 2015/0164370 A1 | 6/2015 | Wabel et al. |
| 2015/0258277 A1 | 9/2015 | Halpert et al. |
| 2015/0320363 A1 | 11/2015 | Haan |
| 2016/0151554 A1 | 6/2016 | Jansson et al. |
| 2016/0166748 A1 | 6/2016 | Meyer et al. |
| 2016/0374596 A1 | 12/2016 | Barrett |
| 2016/0377530 A1 | 12/2016 | Barrett |
| 2017/0072125 A1 | 3/2017 | Wallenås et al. |
| 2017/0196517 A1 | 7/2017 | Zhang |
| 2017/0202493 A1 | 7/2017 | Bezemer |
| 2017/0224897 A1 | 8/2017 | Kopperschmidt et al. |
| 2017/0232174 A1 | 8/2017 | Gerlach et al. |
| 2017/0239409 A1 | 8/2017 | Reyes et al. |
| 2017/0258979 A1 | 9/2017 | Fulkerson et al. |
| 2017/0265793 A1 | 9/2017 | Maierhofer |
| 2017/0281849 A1 | 10/2017 | Goto et al. |
| 2017/0340801 A1 | 11/2017 | Roger et al. |
| 2017/0348471 A1 | 12/2017 | Goto et al. |
| 2018/0055988 A1 | 3/2018 | Brun |
| 2018/0140761 A1 | 5/2018 | Rovatti et al. |
| 2018/0169315 A1 | 6/2018 | Rovatti et al. |

FOREIGN PATENT DOCUMENTS

| | | |
|---|---|---|
| EP | 2388030 B1 | 11/2011 |
| EP | 2558967 A1 | 2/2013 |
| EP | 2656785 A1 | 10/2013 |
| EP | 2678070 A2 | 1/2014 |
| EP | 2734111 A2 | 5/2014 |
| EP | 2735323 B1 | 5/2014 |
| EP | 2730302 B1 | 12/2014 |
| EP | 2836112 A1 | 2/2015 |
| EP | 2670454 B1 | 12/2015 |
| EP | 2578147 B1 | 4/2016 |
| EP | 3145393 A1 | 3/2017 |
| JP | 2004313522 A | 11/2004 |
| JP | 2008264217 A | 11/2008 |
| JP | 2009273749 A | 11/2009 |
| JP | 2009273750 A | 11/2009 |
| JP | 2009297403 A | 12/2009 |
| JP | 2009297404 A | 12/2009 |
| JP | 2009297405 A | 12/2009 |
| JP | 2010029434 A | 2/2010 |
| JP | 2011047767 A | 3/2011 |
| JP | 4905475 B2 | 3/2012 |

(56) References Cited

FOREIGN PATENT DOCUMENTS

| JP | 5278681 | B2 | 9/2013 |
| JP | 5280874 | B2 | 9/2013 |
| JP | 5301259 | B2 | 9/2013 |
| JP | 5385763 | B2 | 1/2014 |
| JP | 5385764 | B2 | 1/2014 |
| JP | 5548917 | B2 | 7/2014 |
| JP | 2015029882 | A | 2/2015 |
| JP | 2016214367 | A | 12/2016 |
| WO | 2003028860 | A1 | 4/2003 |
| WO | 2011130669 | A1 | 10/2011 |
| WO | 2013010677 | A2 | 1/2013 |
| WO | 2013152854 | A1 | 10/2013 |
| WO | 2012116336 | A3 | 2/2014 |
| WO | 2014090746 | A1 | 6/2014 |
| WO | 2015007596 | A1 | 1/2015 |
| WO | 2015179523 | A1 | 11/2015 |
| WO | 2016057982 | A1 | 4/2016 |
| WO | 2018017623 | A1 | 1/2018 |

OTHER PUBLICATIONS

Extended European Search Report dated Jul. 19, 2019 for European Patent Application No. 19171893.1.
International Preliminary Report on Patentability for PCT/US2015/055031 dated Apr. 11, 2017, including the Written Opinion of the International Searching Authority dated Feb. 26, 2016.
International Search Report and Written Opinion for International Application No. PCT/US2015/055031 dated Feb. 26, 2016.
International Search Report and Written Opinion for International Patent Application No. PCT/US2017/042683 dated Dec. 7, 2017.
International Search Report and Written Opinion dated Aug. 4, 2020 for International Patent Application No. PCT/US2020/034420.
International Search Report issued in corresponding PCT/US2017/042683, dated Dec. 7, 2017.
Japanese Office Action dated Aug. 20, 2019, issued in Japanese Patent Application No. 2019-502220.
Office Action (Communication Pursuant to Article 94(3) EPC) dated Mar. 13, 2019 for European Patent Application No. 15790326.1.
Office Action (Decision of Rejection) dated Sep. 24, 2020 for Japanese Patent Application No. 2019-502220.
Office Action (Examination Report under Section 18(3)) dated Apr. 17, 2019 for UK Patent Application No. 1902215.1.
Office Action (Notice of Reasons for Rejection) dated Feb. 18, 2020 for Japanese Patent Application No. 2019-502220.
Communication under Rule 71(3) EPC dated Mar. 18, 2022 for European Patent Application No. 19171893.1.
Office Action (Notice of Reasons for Refusal) dated Mar. 8, 2022 for Japanese Patent Application No. 2021-007983.
Extended European Search Report dated Jul. 8, 2022 for European Patent Application No. 22169775.8.

Set target HD avg = avg(Pout1, EP)
Set target EP = EP

Set FP3, sync FP1 to
target, target = HD avg

Set FP3, sync FP2 to
target

Set FP3 = FP1-sync+FP2-
sync, turn on PC

Command predefined flow rates

Run sync

Adjust and turn on pressure compensation

FLOW BALANCING DEVICES, METHODS, AND SYSTEMS

CROSS-REFERENCE TO RELATED APPLICATIONS

This application is a continuation of U.S. application Ser. No. 16/317,903, filed on Jan. 15, 2019, which is a U.S. national stage filing under 35 U.S.C. § 371 of International Application No. PCT/US2017/042683, filed Jul. 18, 2017, which claims the benefit of U.S. Provisional Application Nos. 62/524,518 filed Jun. 24, 2017 and 62/363,394 filed Jul. 18, 2016, all of which are hereby incorporated by reference in their entireties.

STATEMENT OF GOVERNMENT SUPPORT

This invention was made with government support under HR0011-13-C-0023 awarded by Department of Defense/ Defense Advanced Research Projects Agency (DOD/ DARPA). The government has certain rights in the invention.

BACKGROUND

A basic function of many extra corporeal blood treatment systems (ECBT systems), including hemodialysis, hemofiltration, hemodiafiltration, apheresis systems, etc., is the maintenance of the overall fluid balance between the fluid added to the patient and the fluid withdrawn from the patient. Ideally, this exchange will result in a net loss or gain of fluid to/from the patient that precisely matches the patient's treatment requirement. To achieve this, the ECBT may employ a volumetric fluid balancing system, of which a variety of different types are known. For example, see U.S. Pat. Nos. 5,836,908, 4,728,433, 5,344,568, 4,894,150, and 6,284,131, each of which is hereby incorporated by reference as if fully set forth in their entireties herein.

Fluid balancing mechanisms generally attempt to ensure that the total mass or volume of fluid pumped into, and removed from, the non-blood side of a filter or dialysis are equal. To provide for a desired differential between the net quantity removed/added, the inflow and outflow rates can be controlled to produce a net difference. This may be provided by regulating the relative flow rates provided by ingoing and outgoing pumps or by using a separate bypass, driven by a separate pump. In an example, such a bypass pump pumps at an ultrafiltration ("UF") line rate which is added to the balanced withdrawal rate.

Gravimetric systems that balance flow by weighing mass from a source and collected fluid from the treatment device and comparing the two are known. Another approach is to measure incremental volume transfer. Hard plumbed or disposable lined balance chambers alternately fill and empty in a manner that assures equal and opposite volume exchange. Systems using this approach are balancing a single inlet fluid flow with an effluent stream. A second stream of fluid is frequently added to the extracorporeal circuit using an additional pump, or external IV pump. The volume of this second stream may be balanced by the isolated ultrafiltration (UF) pump in an attempt to maintain patient fluid balance. This approach is limited by the calibration inaccuracies of the additional or external pump and the isolated UF pump. These inaccuracies are acceptable at low flow rates. However, at higher flow rates the cumulative volumetric inaccuracies may not achieve the desired patient volumetric balance. Additionally, this approach requires an operator to independently set the pump rates to achieve the desired balance.

SUMMARY

The disclosed subject matter described in this disclosure is an alternate approach to volumetric fluid balance using multiple volumetric or fixed-displacement pumps to control inflows and outflows from an extracorporeal circuit that have corresponding pump rates synchronized relative to each other to assure balanced flow rates.

In certain systems, volumetric fluid balancing may be performed for a single therapy fluid stream using a system configuration including balance chambers, peristaltic pumps, and mechanically controlled pinch valves. The therapy fluid entering the blood path of the extracorporeal circuit may be balanced with effluent removed from the blood path through the dialyzer of the circuit so that the patient volume is not affected by this exchange of fluids. The limitation to a single therapy fluid inlet flow is a common limitation of various dialysis machines that use balance chambers. Some extracorporeal therapies can use more than one therapy fluid inlet flow that may be volumetrically controlled to achieve an overall patient fluid balance. For example, the difference between the total fluid that moves into the patient (for example, by flowing into the patient's blood stream) and that withdrawn from the patient must be precisely controlled. For example, in dialysis treatment, the amount of fluid entering the patient, for example through predilution, post-dilution, citrate infusion, and reverse ultrafiltration streams may be balanced against the net ultrafiltration stream to achieve a target net ultrafiltration rate. The subject matter described in this disclosure provides alternate machine configurations that support one or more therapy fluid flows synchronized with the effluent fluid flow from the extracorporeal circuit to achieve accurate fluid balance.

The disclosed subject matter includes several different system configurations that support one or more therapy fluid inlet flows balanced with the effluent flow by diverting each therapy flow pump individually using a valving/flow diversion mechanisms that flow fluids, including blood and/or treatment fluid treatment configuration into a series configuration in which fluid is pumped from one pump to another and the pumping rates synchronized using an imbalance detection device. One imbalance detection is the change in weight of fluid accumulating due to back-up of the serial flow. Another imbalance detection is the pressure buildup due to fluid volume accumulation caused by back-up of the serial flow. In other embodiments, pumps are individually calibrated at relevant times (one or more times per treatment for example) against a common or gold standard flow rate measurement device. In still other embodiments, imbalance is detected during treatment without establishing a special configuration by directly measuring the flow rates of fluid, directly by flow measurement or indirectly by measuring pressure changes to infer balanced or imbalanced flow conditions from a temporal trend which can be predict the magnitude of imbalance. For example, one of the pumps can be incrementally stepped, the pressure change or fluid weight trend sampled for a period of time for each step, to establish a trend, and perfect balance fitted to the trend in order to back out the synchronized flow rates arithmetically. Any type of fitting function may be used such as a straight line or polynomial. When pumps are synchronized, the operating condition are maintained to ensure the synchronization conditions, for example suction pressure, are comparable to those during synchronization.

In embodiments, reliable flow balance is obtained by synchronizing the pump flows and using the pressure sensor to synchronize the rates rather than enforcing a fixed-volume flow channel. A controller connected to the pressure sensor and pumps adjusts the effluent flow pump to the desired flow rate and the selected therapy fluid flow pump to achieve a desired pressure between the pumps and holds the pressure stable for a period of time to achieve a synchronization flow value for the therapy fluid pump. This can be repeated for one or multiple inlet pump pressure values and stabilization times to achieve a synchronization curve for the therapy fluid flow pump versus pressure. Alternatively, it can be done for a single condition that is to be maintained during treatment. If the system needs to change operation state due to an uncontrolled change such as a change of flow resistance of a patient access or a controlled change such as a shift to a lower or higher flow rate, new synchronization at the new condition may be performed. Once synchronized, small excursions from the synchronized condition that occur thereafter, for example during treatment, will be adjusted— for, such as when the rates of the pumps that were synchronized during synchronization are varied from their absolute or relative operating speeds, for example to provide a selected ultrafiltration rate. The accommodation is provided by continuously performing pump pressure compensation, which refers to recalculating the relationship between the commanded flow rate (or equivalent such as shaft speed or cycle rate depending on the type of pump) and estimated actual flow rate based on known or measured pump curves. The pump curves may flow versus outlet minus inlet pressure or flow versus inlet pressure only. Other variations are possible depending on the type of pump. In variations, the synchronization process may be triggered by change in arterial pressure, blood treatment device blood side pressure, blood treatment device treatment fluid side pressure, or after a time interval. Such triggered synchronizations may be done for prescribed (i.e., predefined) blood and treatment fluid flow rates only so that a synchronization process over multiple conditions is not required. This "spot synchronization" process is particularly relevant in combination synchronization processes where no bypass flow is established so that treatment does not have to be significantly disrupted as described below with reference to FIG. 8, for example. Synchronization may be done during a priming operation, during treatment, or both. Spot synchronization may be done after a period of time over a treatment as well. The reason for triggering a synchronization after a period of time in the absence of any other change may be, for example, changes in material properties over time or due to extended use, for example a plastic pumping tube segment may exhibit changes in characteristics over continued use during a treatment. Thus to maintain accuracy of balancing, a synchronization may be performed after a time estimated to ensure that the amount of change is limited.

In embodiments, rather than continuously or repeatedly readjusting the flow rates of pumps to compensate for inlet pressure variation, the cumulative error caused by variations in pumping rates over a treatment interval are calculated and stored over time. Then the pumping rates are adjusted at a single time (at several times) for a calculated period of time to compensate for the impact of the error on total ultrafiltration that occurred over the treatment interval. The stepwise correction may be done in a single operation at one time toward the end of a single treatment interval or multiple times over multiple treatment intervals into which a single treatment session is divided. These operations may be done automatically without operator intervention. The treatment intervals may be defined according to events such as shutdowns due to automatic alarms or operator commands. For example, the pumping rates may be adjusted according to cumulative effect of error prior to a shutdown by adjusting the pumping rates immediately after restart. Also, compensation by adjusting the pumping rates can be done multiple times at regular intervals or at other predefined times during a treatment.

Once synchronized, the pumps rates may be changed to implement a predefined difference in commanded pump speeds according to a stored pump curve. The pump curve is not limited to a stored formula or algorithm but may also be implemented as a look up table or equivalent. The difference in commanded pump speeds is adapted to provide for a prescribed or otherwise provided ultrafiltration rate. The different speeds may provide for a desired fluid balance outcome in the extracorporeal circuit (neutral, positive, or negative balance). In embodiments, the difference in speed may be limited to a minor fractional difference (i.e., less than 50% speed difference) and may be limited to fractional differences of less than 20% or 10% to ensure and improve accuracy during treatment. In any of the embodiments, the synchronization may include multiple flow, for example, a predilution flow of replacement fluid which would flow into a patient's blood during treatment, plus a fresh dialysate flow and synchronized with a flow of waste. As indicated, the pump rates may be further compensated to account for transient effects such as changes in inlet/outlet pressures, changes due to pump life, and other factors. A compliant accumulator or additional tubing lengths can be used to reduce pressure spikes and aid in achieving stable pressure control during the synchronization process.

The embodiments are applicable to synchronization of series (serially interconnected through a treatment device) blood pumps or series treatment fluid pumps. In embodiments, directly flow between the series pumps is provided by halting flow through lines that exchange fluid with the flow path connecting the series pumps to be synchronized. For example, two series blood pumps connected to a filter have a fixed volume path between then when flow through lines connected to the non-blood side is prevented, such as by halting one or more treatment fluid pumps, clamping one or more treatment fluid lines, or both. For another example, two series treatment fluid pumps connected to a filter have a fixed volume path between then when flow through lines connected to the blood side is prevented, such as by halting one or more pumps, clamping one or more blood lines, or both. The fixed volume can be implemented by any suitable means for halting flow on the other side (other side of the pumps used for balancing) of the treatment fluid device including halting inflow and outflow pumps on said other side or halting a single pump such as an inflow pump and clamping the other line, such as an outflow line. These may depend on the configuration.

All pumps may be equipped with an inlet pressure sensor and may also be fitted with an outlet pressure sensor to support pressure compensation of the pump rate. In a pressure compensation method, the flow rate of the pump may be derived from the pump rotation or reciprocation rate and adjusted responsively to the inlet and/or outlet pressure. This derivation and compensation may be done using a single function of both pressure (inlet, outlet, or pressure change) and rotation speed. For example, the function may be embodied in a look up table stored in a data store of a controller. Additionally, the control valves may be closed so that pump occlusion may be confirmed by the reading of the various pressure sensors.

In embodiments, flow is halted in the non-blood compartment of a treatment device and an average blood compartment pressure is established by flowing fluid through the blood compartment of the treatment device by pumping fluid into the blood compartment and with a predefined resistance at the outlet of the blood compartment. This average pressure is stored as a target. The dialysate compartment pressure is affected by the oncotic pressure caused by the presence of protein in the blood. Fresh and waste treatment fluid pumps connected to the non-blood compartment are then synchronized by commanding the waste treatment fluid pump to a predefined treatment fluid flow rate and adjusting the fresh treatment fluid pump rate until the target average blood compartment pressure is restored in the blood compartment. In alternative embodiments, the target may be established from the treatment fluid pressure (e.g., taking an average of the inlet and outlet treatment fluid pressure at the inlet and outlet ports of the treatment fluid device). By measuring the difference between treatment fluid device treatment fluid compartment pressure and blood compartment pressure during zero (or near-zero) transmembrane flow conditions, oncotic pressure may be directly determined. The technique may be used to determine the oncotic pressure which may be used as well for other purposes, such as determining the magnitude of ultrafiltration required (i.e., how much excess fluid is in the patient's blood—hypervolemia). The synchronized fresh treatment fluid pump rate is recorded. This procedure may be repeated for multiple predefined pumping rates and blood compartment pressures to record a table of blood compartment average pressures and predefined treatment fluid flow rates as the independent variables (e.g., rows and columns although any data storage element may be used) and a corresponding synchronized fresh treatment fluid flow rate for each combination (e.g., recorded in the cells of the table). The data may be fitted to a function to estimate a synchronized fresh treatment fluid pumping rate for any prescribed combination of treatment fluid flow rate and blood flow rate through the blood compartment, which will correspond, during treatment, to an average pressure of the blood compartment. When treatment is performed, the average blood compartment pressure is measured and applied to the fitted function, with a prescribed treatment fluid flow rate, to obtain an estimated fresh treatment fluid flow rate. A modified waste treatment fluid flow rate is then calculated to provide for a prescribed ultrafiltration rate. The pumping rate of the waste treatment fluid flow rate may be generated from a function of inlet pressure and target flow rate that provides a command flow rate to be applied to the pump. Such functions are commonly used for controlling peristaltic pumps. The step in commanded flow required by the waste treatment fluid pump to achieve the required ultrafiltration may be calculated from such a function and the current waste treatment fluid inlet pressure, then the waste treatment fluid pump commanded correspondingly. The new inlet pressure may be fed back iteratively to obtain a refined command flow for the waste treatment fluid pump until the inlet pressure stops changing within a predefined interval. Whenever, during treatment, the average blood compartment pressure changes beyond a predefined threshold, the fresh treatment fluid pump rate may be adjusted to return the average blood compartment pressure to the target and the waste treatment fluid pump rate reestablished iteratively as above. If the average blood compartment pressure changes beyond a greater threshold, the fresh treatment fluid pumping rate may be recalculated based on the prescribed treatment fluid flow rate as above and the waste treatment fluid pumping rate adjusted iteratively as above based upon a prescribed ultrafiltration rate.

The principles of the subject matter disclosed herein are applicable to both peristaltic pumps with disposable fluid pathways as well as hard plumbed systems and combinations of the two. In a hard plumbed configuration, the flow path components may require disinfection similar to standard dialysis machines and would require special techniques to meet the requirements for direct infusion of therapy fluids.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1A:
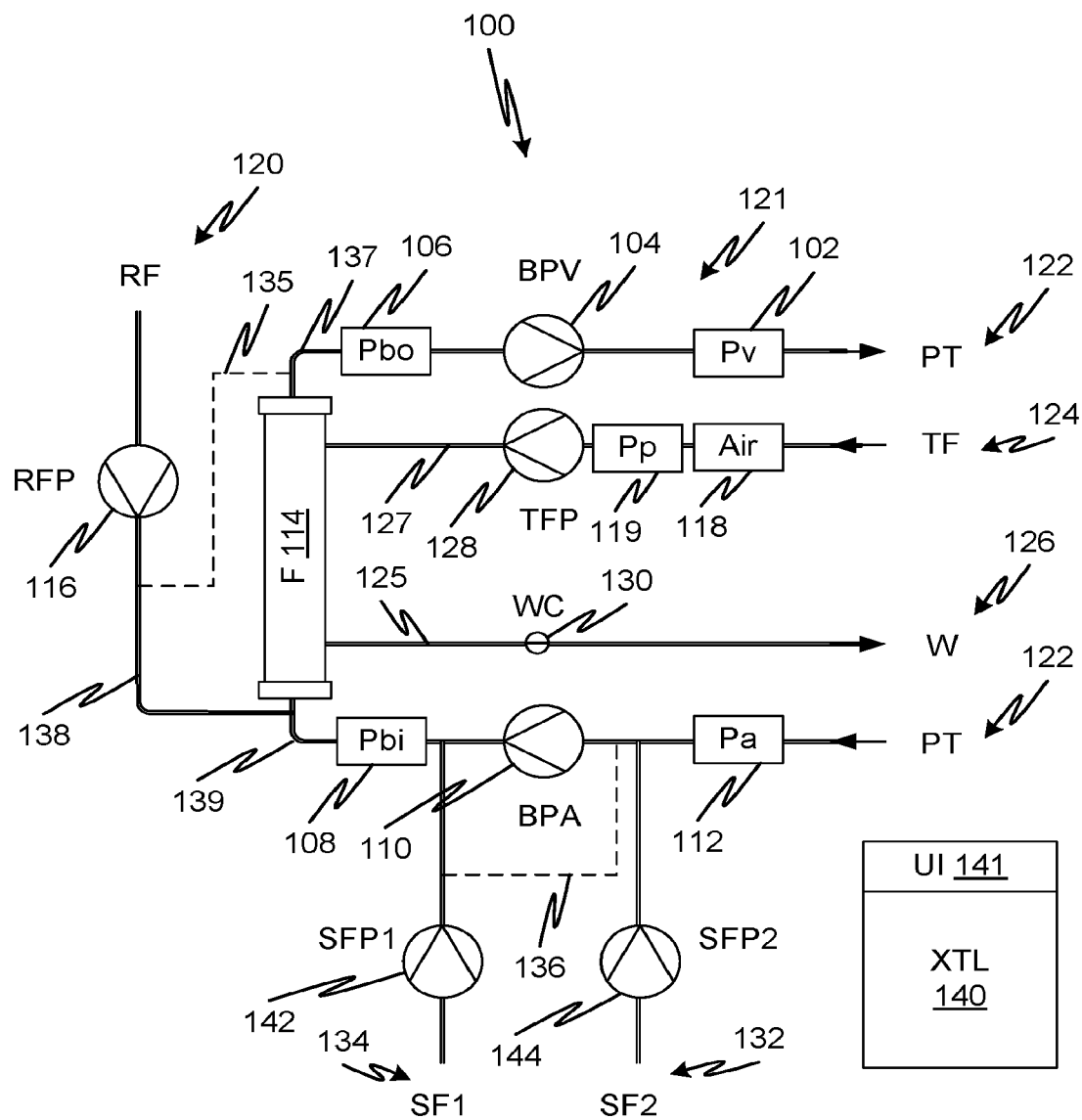
FIG. 1A shows a blood treatment system that regulates the flow of blood into and out of a treatment device to generate a cumulative target ratio of fluid drawn or infused into a patient over the course of a treatment according to various embodiments of the disclosed subject matter.

FIG. 1A shows a blood treatment system 100 that regulates the flow of fluid in a fluid circuit 121 that includes an arterial blood line 139, a venous blood line 137, a fresh treatment fluid line 127 and a waste treatment fluid line 125. In particular, the blood treatment system 100 regulates the flow of fluid across a membrane of a treatment device 114 to generate a cumulative target ratio of fluid drawn from, or infused into, a patient over the course of a treatment. During set-up procedures, instead of a patient being hooked up to the connections 122 and at those times, or in that case, 122 identifies sources and sinks (or a recirculating container) of priming fluid. The control of the pumps provides a net flow of fluid across a membrane (and concomitantly to/from a patient or priming fluid source/sink). Hereafter it should be understood that in any of the embodiments, any reference to "patient" and/or "blood" with reference to a fluid balancing or pump synchronization may be replaced by priming fluid and/or a combination source and sink thereof, because the fluid balancing and synchronization mode/operation modes discussed herein can be done during priming as well as using blood during a treatment. It should also be understood that the priming fluid source/sink may be a single recirculating channel or chamber as well as a single-pass arrangement with a separate source and sink. At any given time, the net rate of flow across the membrane (identified in renal treatment as the ultrafiltration rate) is determined by a then-instant difference between the volume of blood pumped out of a treatment device 114 (for example a dialyzer) to the volume of blood pumped into the treatment device 114 plus the fluid pumped into the blood lines. The ultrafiltration rate may also be understood as the total amount of fluid transferred from the patient taking into account any replacement fluid 120 and/or other fluid (supplemental fluids SF1 and SF2 such as anticoagulant or drug) that is conveyed directly to the patient's blood.

Returning to FIG. 1A, blood is pumped into the treatment device 114 by an arterial blood pump 110 and pumped from the treatment device 114 by a venous blood pump 104. The illustrated configuration is common for dialysis systems, and may include all the typical incidents thereof, but differs specifically in that there are two blood pumps: the arterial blood pump 110 and the venous blood pump 104.

During a treatment mode and also in embodiments of a synchronization mode, blood is pumped to and from a patient access 122. In other embodiments synchronization may be performed, instead, with a priming fluid. During priming operations, the patient access or priming connector(s) may be connected to priming fluid source, sink, or recirculating container instead. Thus, 122 may be considered generally to represent a patient access connected to a patient, in which case the circulating fluid is blood, or 122 may be at other times a priming fluid source, sink, or recirculating container, in which case, the circulating fluid would be priming fluid.

Control and sensing are provided by a controller 140 which may be of any form but typically some type of programmable digital controller, for example, an embedded computer. A treatment fluid is pumped from a treatment fluid source 124 through an air detector 118 (also referred to as an air sensor) through the treatment device 114, past a waste line clamp 130, to the drain 126 (indicated by W for waste). The pumps, clamp, and all sensors may be connected for control and input by the controller 140. Drain 126 may be a drain of a plumbing system or a collection container or any other device for disposal of waste treatment fluid. Treatment fluid 124 may be dialysate, replacement fluid, or any other medicament.

A replacement fluid 120 may be pumped into the arterial blood line 139 or the venous blood line 137 through a replacement fluid line 135 or 138, respectively (or both) for predilution, post-dilution or a combination of both. In alternative embodiments, the dilution may occur at a midpoint of the treatment device 114, for example in a case where the treatment device 114 were composed of two smaller units that provided a fluid connection junction between them to admit fluid at that point to the blood compartment. A mid-dilution treatment device may have a special construction to provide for mid-dilution. The treatment device 114 may be adapted for a variety of types of blood treatment that require balancing flows into and out of a patient blood compartment, including, but not limited to, dialysis, hemofiltration, hemodiafiltration, apheresis, adsorption, or hemoperfusion. These treatment modalities may apply as alternatives to any of the disclosed embodiments including those originally disclosed in the claims. Further supplemental fluids indicated by supplemental fluid 134 and supplemental fluid 132 may be pumped into the arterial blood line 139 by respective pumps, namely, a supplemental fluid pump 142 and a supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the arterial blood line 139 upstream of the arterial blood pump 110. In embodiments, each pump contributing to flow balance may have a pressure sensor up stream of it to ensure that pressure compensated control of its speed can be provided. For example, an additional treatment fluid pump pressure sensor 119 may be provided. In embodiments, pressure sensors used for pressure compensated speed control are positioned such that they provide a reliable and consistent indication of pressure upstream of the respective pump or pumps. Thus, they may be positioned close or at least such that there are no intervening possible interferences such as tube lengths that could become kinked. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 104 and downstream of the treatment device 114. A venous blood pressure sensor 102 may detect pressure in the venous blood line 137 downstream of the venous blood pump 104 and upstream of the patient access 122. The controller 140 receives signals from each of the arterial pressure sensor 112, blood inlet pressure sensor 108, blood outlet pressure sensor 106, and venous blood pressure sensor 102 as well as an air detector 118 that is positioned to detect air in the fresh treatment fluid line 127. The controller 140 is also connected to control each of the arterial blood pump 110, venous blood pump 104, replacement fluid pump 116, supplemental fluid pump 142, and supplemental fluid pump 144, as well the waste line clamp 130.

Note that the waste line clamp 130 could be replaced by any type of valve that selectively halts or permits flow or another pump. Note that the pressure sensors may be of any of a variety of types of pressure sensors used for indicating pressure in a fluid circuit, for example bubble chambers, pressure pods (e.g. U.S. Pat. No. 8,092,414), and the like.

In alternative configurations, instead of treatment fluid pump 128 and waste line clamp 130 being used to halt flow as described below, a waste fluid pump may be provided in the position of waste line clamp 130, which can halt flow by halting rotation. In any of the embodiments, including the present and further embodiments to be described below or described above, any element identified as a line or fluid line (or fluid circuit) could be any type of flow channel including interconnected tubes including pumping tube segments, channels formed in a cartridge (as a pattern of troughs sealed by an overlying welded film), a pattern-welded pair of weldable sheets, a laminated stack of elements that defines flow channels, or any other device that guides the flow of fluid. Any element identified as a pump may be any type of pump or actuator that is volumetric aka, positive displacement type. Such embodiments of lines and fluid lines or fluid circuits may be disposable or otherwise replaceable components that engage pumps, sensors, and actuators of a treatment machine that includes such pumps, sensors, and actuators as identified in the embodiments. Such a machine may be illustrated schematically in the drawings, but not necessarily as a separate component, for example a pump indicated by a single element may include a pump actuator, e.g., a rotor, that works together with a pump tubing segment of a fluid circuit, while both are indicated by a pump symbol schematically in the drawing. Similarly, sensors and clamps are not illustrated separately in all the drawings. Such a machine may be embodied in multiple separate components and may be generally described as having a receiving adapter to allow the connection of a disposable fluid circuit.

The term, receiving adapter, or similar term is an abstraction that may cover all the various mechanisms that permit the operative association between a permanent device and a disposable or replaceable component which together form one of the apparatuses disclosed or claimed. This applies to all the disclosed and claimed embodiments. For example, the drawings described above and below illustrate a system which, when considering that portions are replaceable, indicate the presence of a blood circuit receiving adapter and a medicament (treatment fluid, dialysate, or similar fluid) receiving adapter. The fluid circuits (including blood circuits) may include treatment components as well as portions that engage with sensors and actuators. Again, these comments apply to all embodiments.

Any element identified as a pressure sensor may be a combination of a fluid circuit portion such as a pressure pod or drip chamber and an electronic transducer such as a strain gauge or displacement encoder connected to an element such as a diaphragm that registers pressure. The foregoing elements are well known classes of devices and further elaboration is not needed to permit the skilled reader to develop the details of working embodiments of the described subject matter. Fluids may be supplied from containers such as bags or inline fluid generators such as used in dialysis clinics.

In a treatment operation of blood treatment system 100, arterial blood pump 110 and venous blood pump 104 pump blood or priming fluid in the directions indicated by the respective arrowhead of each pump symbol. They pump at rates controlled by the controller 140 to approximately balance (equivalently, "equalize") the flow of blood in the arterial blood line 139 against the flow of blood in the venous blood line 137 such that a net take-off of fluid (ultrafiltrate) or a net infusion of fluid takes place (which may be called negative ultrafiltrate). The instantaneous rate of ultrafiltrate referring to net loss of fluid by the patient and negative referring to net gain of fluid by the patient) is achieved through control of the total displaced volume by the arterial blood pump 110 relative to the venous blood pump 104. The ultrafiltrate may be established by a predetermined ratio of the flow rates of the arterial 110 and venous 104 blood pumps if the transfer is spread uniformly over the treatment interval or the net ultrafiltrate may be established in a discontinuous manner by varying the ratio of the flow rates of the arterial 110 and venous 104 blood pumps to achieve a cumulative ultrafiltrate. Thus, ultrafiltrate volume is established by the total volume transported by the venous blood pump 104 minus the total volume transported by the arterial blood pump 110 over the course of a treatment.

Ultrafiltrate rate may identify the instantaneous difference between the rates of the venous 104 and arterial 110 blood pumps.

The controller 140 may be programmed to ensure that the net volume of ultrafiltrate or infused fluid meets a prescribed target which may be stored by the controller 140. The pumping speeds required to achieve commanded flow rates may be determined by the controller 140 using data stored by the controller such as look up tables or formulas. A commanded flow rate refers to the operational property (e.g., shaft speed of a peristaltic pump) that is under directly control of the controller which corresponds more or less accurately to a flow rate, conditions that may vary from those used to establish a transfer function defining the relationship between the operational property and an actual flow rate produced by it. The conditions may include manufacturing variability such as pumping tube segment and fluid line diameter, material properties of the pumping tube segment, pump lubrication, as well as factors that change due to operation history and storage such as distortions, material creep, etc. The ratio of flow rate to pump speed may be presented by stored look-up table data to indicate target pump speeds by a relationship between pressure difference and flow rate.

Treatment fluid 124 is pumped by fresh treatment fluid pump 128 at a predefined rate stored in the controller 140, which rate may be selected to correspond to the blood flow rate. The replacement fluid 120 may be pumped at a rate controlled by the controller 140 by controlling the commanded rate of replacement fluid pump 116. The supplemental fluid 134 may be pumped at a rate controlled by the controller 140 by controlling the commanded rate of supplemental fluid pump 142. The supplemental fluid 132 may be pumped at a rate controlled by the controller 140 by controlling the commanded rate of supplemental fluid pump 144. Any of the replacement fluid 120, supplemental fluid 134, or supplemental fluid 132 are optional and may or may not be included, along with the respective lines and pumps, in alternative embodiments.

Valves or pinch clamps identified anywhere in the current patent application may be of any type. For example, flexible membranes closed over cartridge-embedded ports, electrically actuated pinch clamps employing linear actuators such as solenoid plungers or stepper motor actuators may be used. The particular type of valve mechanism does not limit the disclosed subject matter. Line 136 is present to indicate that in alternative embodiments, the supplemental fluids may enter the arterial blood line 139 upstream or downstream of the arterial blood pump 110.

As indicated above, in any of the embodiments, the fluid balance (net ultrafiltrate volume) resulting from the flows to and from a patient is understood to accrue over a period of time. Thus, although in the embodiments, the controller is described as controlling pumping rates to achieve a fluid balance, optionally offset by a net transfer of fluid to or from the patient (net ultrafiltrate volume), it is understood that the pumping rates need not be constant, define a constant ratio over time, or even define a smoothly varying ratio over time. Since the ultimate goal is to control the total loss or gain of fluid from a patient (net ultrafiltrate volume), pumping rates can establish a variety of rates over time such that the cumulative effect is the target ultrafiltrate volume at the end of the treatment. Rates may be constant or vary step-wise, smoothly, and may result in a temporary gain of fluid by the patient during a portion of a treatment interval and net loss during another portion to achieve a total gain or loss for the entire treatment. For another example, the entire fluid gain or loss can be confined to a single part of the treatment interval. The controller may also limit estimated ultrafiltrate so that overall balance does not exceed a certain volume at a given time. A rate of ultrafiltration may also, or alternatively, be limited by the controller.

Figure 1B:
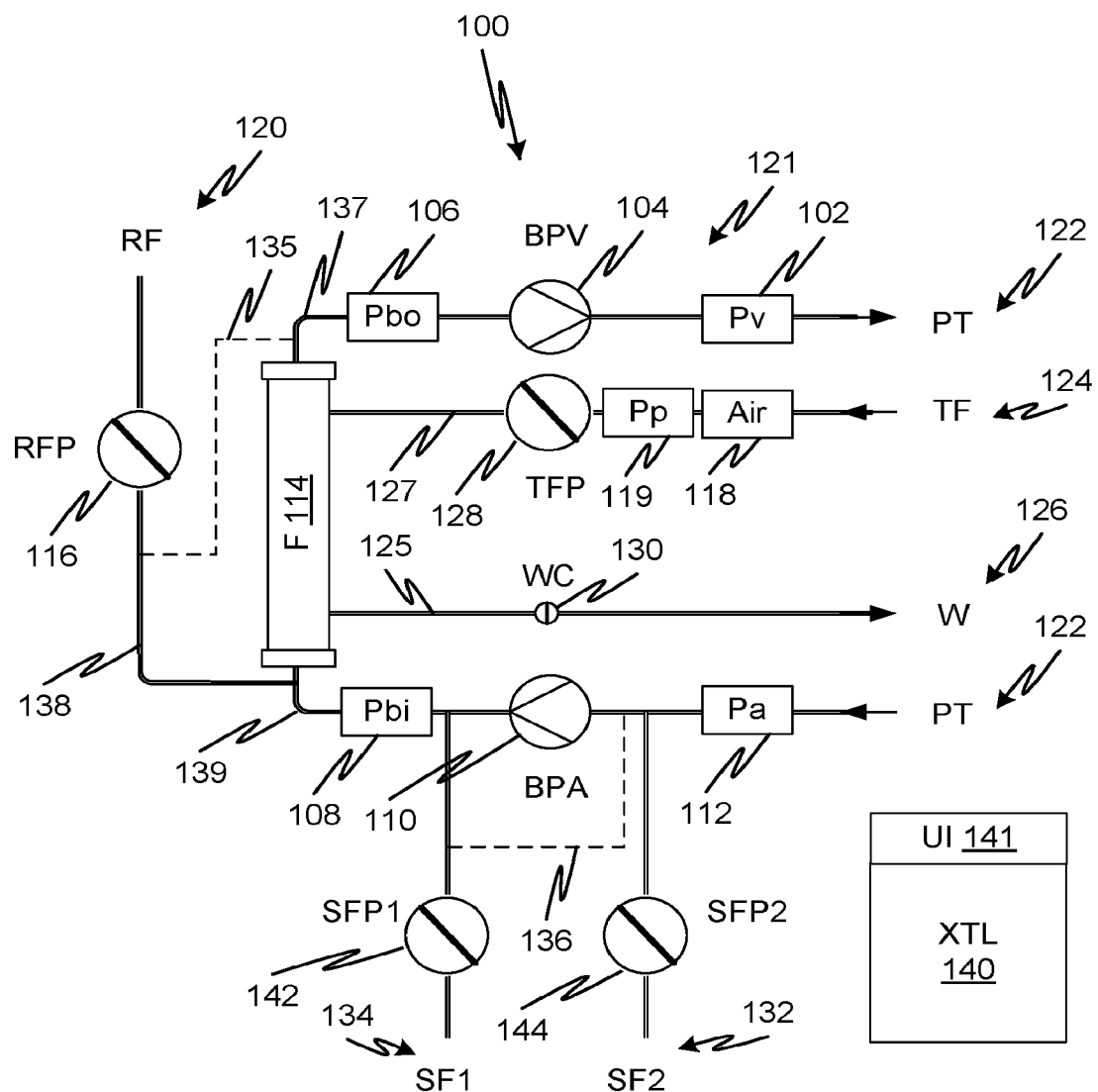
FIG. 1B shows the system of FIG. 1A in a configuration, implemented by the controller, for synchronizing pumps with only one fluid source according to various embodiments of the disclosed subject matter.

FIG. 1B shows the system of FIG. 1A in a configuration implemented by the controller 140 to synchronize the pumps for equal flow while pumping a single fluid, blood or priming fluid 123. At the beginning of a treatment or at times during a treatment (as further discussed later with reference to FIGS. 2A and 2B), a synchronization procedure is performed. The treatment fluid pump 128, the replacement fluid pump 116, supplemental fluid pump 142, and supplemental fluid pump 144 are all held in a halted configuration to block flow (i.e., prevent flow) through a respective line into or out of the treatment device 114. Where non-positive displacement pumps are used, an auxiliary valve, such as a pinch clamp, may be included to prevent flow and in such cases, the combination of the non-positive displacement pump and valve may by identified compactly in the current specification and claims as a pump. The halted flow configuration is indicated by the universal prohibition safety sign (/) overlying the pump symbols. The waste line clamp 130 is shown closed (again the waste line clamp 130 may be any type of valve). In this configuration, the arterial blood pump 110 and the venous blood pump 104 are directly connected in series such that there exists a fixed volume between the arterial blood pump 110 and the venous blood pump 104.

To perform a synchronization, during a synchronization mode, the arterial and venous blood pumps 110, 104 may be initially commanded to flow at a predefined pump speed corresponding to a commanded flow rate of the blood stored by the controller 140. During preparation for a treatment, this may be done, as indicated elsewhere, using priming fluid rather than blood. It may be done during treatment using blood. The commanded flow rate may be one indicated for a prescription for treatment. The latter may also be directly entered through a user interface 141 of the controller 140. Any differences in the volume flow rates pumped by the arterial blood pump 110 and venous blood pump 104 may be detected from the blood outlet pressure sensor 106, the blood inlet pressure sensor 108, or an average of the two. That is, a rising pressure trend indicates the arterial blood pump 110 is pumping at a higher flow rate than the venous blood pump 104 providing a feedback. Using the pressure signal, the controller may compensate by slaving one of the venous blood pump 104 and arterial blood pump 110 to the other of the venous blood pump 104 and arterial blood pump 110 until the volume rates of the two pumps are equal, i.e., the pumps are synchronized. By "slaving" it is meant that one pump is PID or PD feedback-controlled until the flow is synchronized with that of the other pump. The synchronization may be performed for one, or more than one flow rate. This may be done in this embodiment and others during an initial priming stage. For each flow rate, the relative speeds of the arterial blood pump 110 and venous blood pump 104 that correspond to identical flow rates may be recorded by the controller, for example as a ratio. The ratio corresponding to equal flows may then be compared to a predicted ratio stored by the controller and a control parameter used for future predicted ratios of commanded flow to actual flow may be derived and stored by the controller 140 for using during treatment. Other data structures to allow the controller 140 to determine and command one of the arterial blood pump 110 and venous blood pump 104 speed to be selected for a speed of the other calculated to provide a commanded flow rate of blood.

Note that in the foregoing embodiment, instead of blocking flow in the treatment fluid lines and synchronizing blood pumps, a system may balance flow using the treatment fluid pumps. In such a system, the flow of blood may be blocked forming a fixed volume channel between the treatment fluid pumps for synchronization. The procedure for this embodiments would be analogous.

Note that in all embodiments, a synchronization operation performed during a synchronization mode as described according to one embodiment above may provide a control parameter for treatment without fully synchronizing the pumps. That is, the controller 140 can determine from the dynamic response of the pressure and commanded flow rates, sufficient information to extrapolate the control parameter. This may save considerable time during a synchronization mode that is implemented during treatment. Thus, a dynamic hydraulic model of the flow system may provide a number of equations whose unknown parameters can be fitted using the pressure and flow rate signals over a period of time which is insufficient to establish equal flows of the pump but sufficient to estimate the control parameter for improving the equal flow estimate during a treatment. There are many choices for a dynamic model depending on the conditions and level of accuracy required. An unsteady hydrostatic model may be sufficient if pumping rates are so low as to produce low flow resistance. Factors such as flow resistance can be incorporated using steady state equations and time-varying flow for rheological fluid and non-rheological fluids may be used)

The synchronization mode operation of FIG. 1B may be triggered by various indications that may be automatically detected by the controller 140. For example, one trigger may be a command received from the user interface 141 to provide an ultrafiltrate volume that corresponds to an average or instantaneous ultrafiltration rate that exceeds a predefined magnitude. For example, the ultrafiltration rate may be recalculated to achieve an ultrafiltrate volume based on a remaining treatment time. The rate may correspond to rates of pumping of the arterial blood pump 110 and the venous blood pump 104 of a certain magnitude. The trigger point for implementing the synchronization mode may be stored as a predefined difference between the commanded pumping rates or a ratio thereof. Alternatively, numerical bounds on absolute or relative ultrafiltration (infusion) rate may be stored and applied by the controller 140. When the blood treatment system 100 is commanded to operate beyond those bounds, the synchronization mode may be implemented. The synchronization mode may be implemented with the additional flows of replacement fluid 120, supplemental fluid 134, and/or supplemental fluid 132 as discussed below.

In a preferred embodiment, the synchronization process covers multiple operating conditions and is done during priming. In this embodiment, the control parameters for multiple operating conditions are used to control the system during treatment. The need to perform a synchronization during a treatment can be avoided. However, various trigger conditions may cause the system to perform a synchronization during a treatment.

Figure 1C:
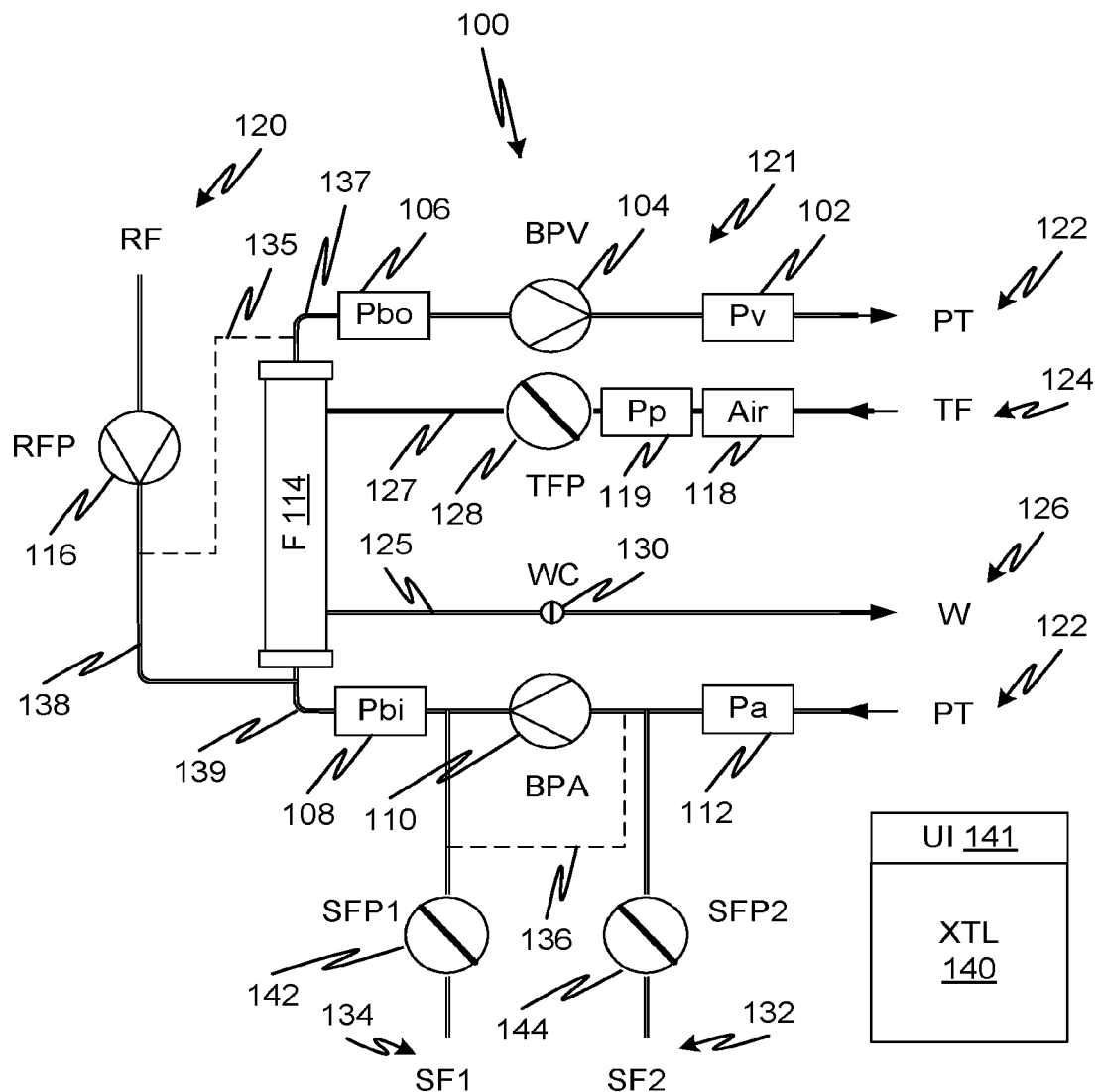
FIG. 1C shows the system of FIG. 1A in a configuration, implemented by the controller, for synchronizing pumps with more than one fluid source according to various embodiments of the disclosed subject matter.

FIG. 1C shows the system of FIG. 1A in a configuration, implemented by the controller, for synchronizing pumps with more than one fluid source. At the beginning of a treatment or at times (determined by trigger events) during a treatment, a further synchronization procedure is performed. The treatment fluid pump 128, supplemental fluid pump 142, and supplemental fluid pump 144 are all held in a halted configuration to prevent flow through a respective line into or out of the treatment device 114. The controller 140 calculates a speed for the venous blood pump 104 and then the controller 140 calculates a flow rate and a pump speed for the operation of each of the replacement fluid pump 116 and the arterial blood pump 110 based on a commanded ultrafiltration rate or infusion rate. The waste line clamp 130 is shown closed (again the waste line clamp 130 may be any type of valve). In this configuration, the arterial blood pump 110 and the replacement fluid pump 116 are connected in series with the venous blood pump 104 such that there exists a fixed volume between the parallel-arranged arterial blood pump 110 and replacement fluid pump 116 and the venous blood pump 104. Thus, the flow through the venous blood pump 104 must match the sum of the flows through the arterial blood pump 110 and replacement fluid pump 116 in order for the pumps to be synchronized.

To perform a synchronization, the pumps may be initially commanded to flow at a predefined pump speed corresponding to a commanded flow rate of the blood stored by the controller 140 and representing a prescription for treatment. The latter may also be directly entered through a user interface 141 of the controller 140. Any differences in the volume flow rates pumped by the arterial blood pump 110 and venous blood pump 104 may be detected from the blood outlet pressure sensor 106, the blood inlet pressure sensor 108, or an average of the two. Using the pressure signal, the controller may compensate by slaving one of the venous blood pump 104 and arterial blood pump 110 toward a matched flow with the other of the venous blood pump 104 and arterial blood pump 110 until the two pump flow rates equalized as indicated by the pressure of the fixed-volume channel. During a synchronization cycle, the replacement fluid pump 116 may be kept at a fixed ratio or a fixed rate of pumping and a slaved one of the arterial blood pump 110 and venous blood pump 104 may be varied until synchronization is achieved or (equivalently) sufficient information is obtained to fit a hydraulic model that can provide the required control parameter. Alternatively, other combinations of the pumps may be halted and/or operated to achieve a relevant target. A PID or PD algorithm, with the pressure signal as a feedback control variable, may be applied by the controller to achieve synchronized pumps. The synchronization may be performed for one, or more than one flow rate. For each, the relative speeds of the replacement fluid pump 116, arterial blood pump 110 and venous blood pump 104 that correspond to identical flow rates may be recorded by the controller, for example as a ratio. Various data structures may be used to store the relevant one or more control parameters to ensure the ratio of speeds of the pumps provides a balance or ultrafiltration rate that is required.

During any synchronization procedures, a target range for venous pressure, as indicated by venous blood pressure sensor 102, may be established. This pressure may be stored by the controller 140 and have a predefined magnitude that is selected based on safety or other operational requirements. Pumping rates may be commanded and regulated to achieve the target venous pressure. During any of the synchronizations and/or during treatment, a predefined flow rate of the supplemental fluid pump 142 and supplemental fluid pump 144 may be established according to prescription. The rates of the supplemental fluid pump 142 and supplemental fluid pump 144 may be imposed by controlling the corresponding pump speeds based on a predefined commanded rate. Generally, the supplemental fluid pump 142 and supplemental fluid pump 144 will not contribute sufficient volume to be relevant to include in fluid balance and thus synchronization may not take their contributions into account. However, this may or may not be the case.

Synchronization may be performed to provide accurate reproduction of balanced flow any time the operational configuration changes or will change, including when new fluid circuits are installed, a new treatment is begun, the flow rates are changed, a flow characteristic of a fluid circuit component (such as flow restriction of a flow element, the patient access, or treatment device) changes, or the commanded characteristics of a treatment are changed. In particular, the synchronization of pumps that contribute significantly to the balance of fluid of the patient is performed under conditions that are as close as possible to those that exist during treatment so that the synchronization data are valid during treatment. In embodiments, a new synchronization may be indicated by the controller based on variables that are estimated or predicted rather than directly measured. For example, the compliance of materials may change with time and/or temperature, for example pumping tube segments of peristaltic pumps. So the lapse of time may be used as a proxy for an indication of material changes. A pause in the operation of a machine, for example an alarm stoppage, may be a trigger for a synchronization mode immediately after restart.

Figure 2A:
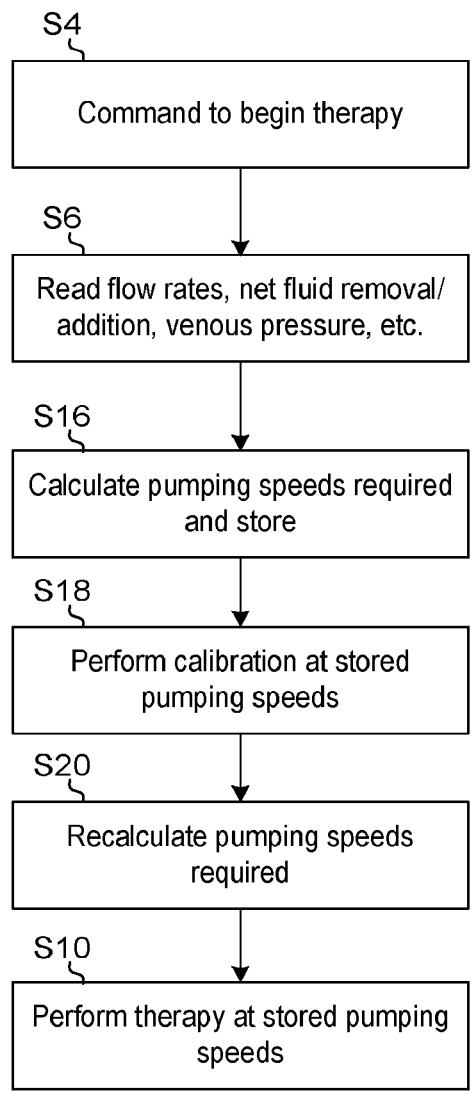
FIG. 2A shows a flow chart of a control method for delivering a treatment while providing balanced flows of independently-controlled pumps where two pumps, an inlet and outlet, are balanced according to various embodiments of the disclosed subject matter.

FIG. 2A illustrates an operating scenario. A command is received by the controller 140 at S4 to begin a treatment. The command may be entered through a user interface operated by the patient, caregiver, or clinician, or it may be received from a remote or local operator directly or indirectly through the user interface 141. At S6, the controller 140 reads prescription data from a data store, which may include user profile information, data about prior treatments and other information. At S16, the pumping speeds required to achieve the commanded flow rate are calculated for each pump based on stored data. Then at S18, the pumps are run and synchronized as described. When the synchronization is achieved, the data that permits the calculation of pump speeds from commanded flow rates are stored and then used at S20 to calculate the pump speeds for the treatment which is performed at S10.

Figure 2B:
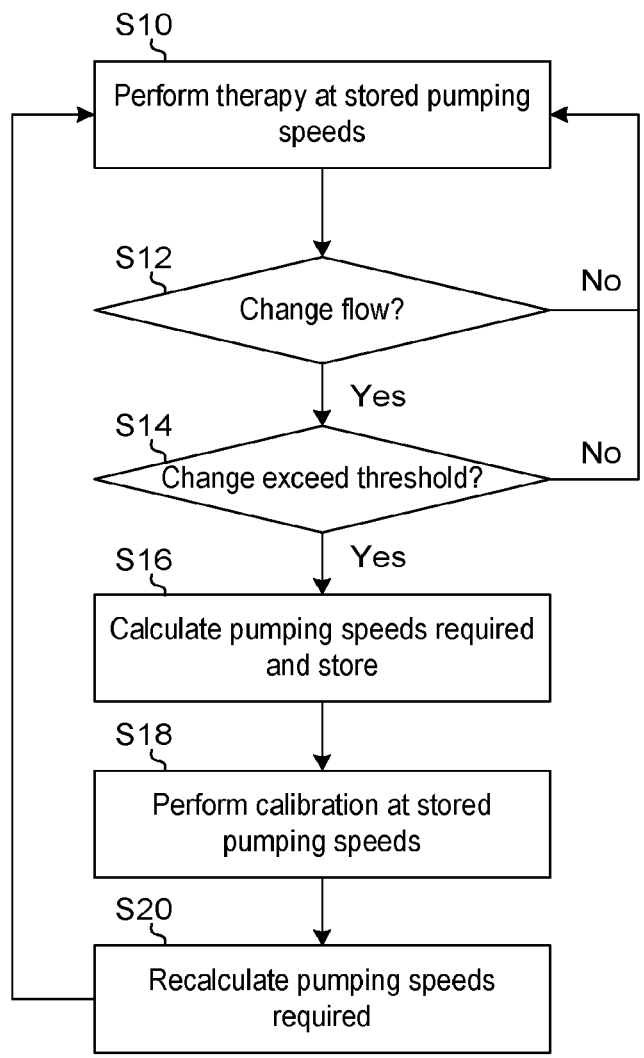
FIG. 2B shows a flow chart of a control method for delivering a treatment while providing balanced flows of independently-controlled pumps where multiple inlet pumps are balanced against one outlet pump according to various embodiments of the disclosed subject matter.

Referring now to FIG. 2B, at S10 (continued from FIG. 2A), before treatment or at any time during a treatment if conditions change such as a commanded change in flow rate as indicated at S12, the controller 140 may determine if a threshold of the flow change exceeds a predefined range at S14. If such an event is determined by the controller and the controller may perform a new synchronization procedure to generate updated control parameter for calculating pump speeds from commanded flow rates as described above. At S16, the pumping speeds required to achieve the commanded flow rate are calculated for each pump based on stored data. Then at S18, the pumps are run and synchronized as described. When the synchronization is achieved, the data that permits the calculation of pump speeds from commanded flow rates are stored and then used at S20 to calculate the pump speeds for the treatment which is performed at S10.

As indicated above, any change in conditions or a programmed lapse of time or other condition at S12 may indicate a candidate for resynchronization. For example, at S12, venous pressure rise to a predefined level may cause the controller to self-command a flow rate reduction. An operator command may indicate a change in flow rate or a change in hemofiltration rate. An operator command to reduce treatment time may require the controller to calculate new flow rates and attending new synchronization. The controller may store product-specific parameters such as the fluid circuit materials or product identifier which may in turn indicate schedule of resynchronization. This may allow the system to compensate for materials with known material property drift which can cause inaccuracy in net fluid balance over the course of a treatment. Such compensation may take the form of more frequent pre-schedule resynchronizations of the flow rate-to-pump speed data using pump synchronization as described.

Note that the system of FIGS. 1A-1C can be modified to place a line clamp like waste line clamp 130 in place of the venous blood pump 104 and using a pump on the waste treatment fluid line 125. In that case, fluid balancing can be done on the medicament side rather that the blood side. The fixed volume channel can be implemented for synchronization by clamping the blood line and stopping the blood pump. In other respects, the system may operate as described above.

Figure 3A:
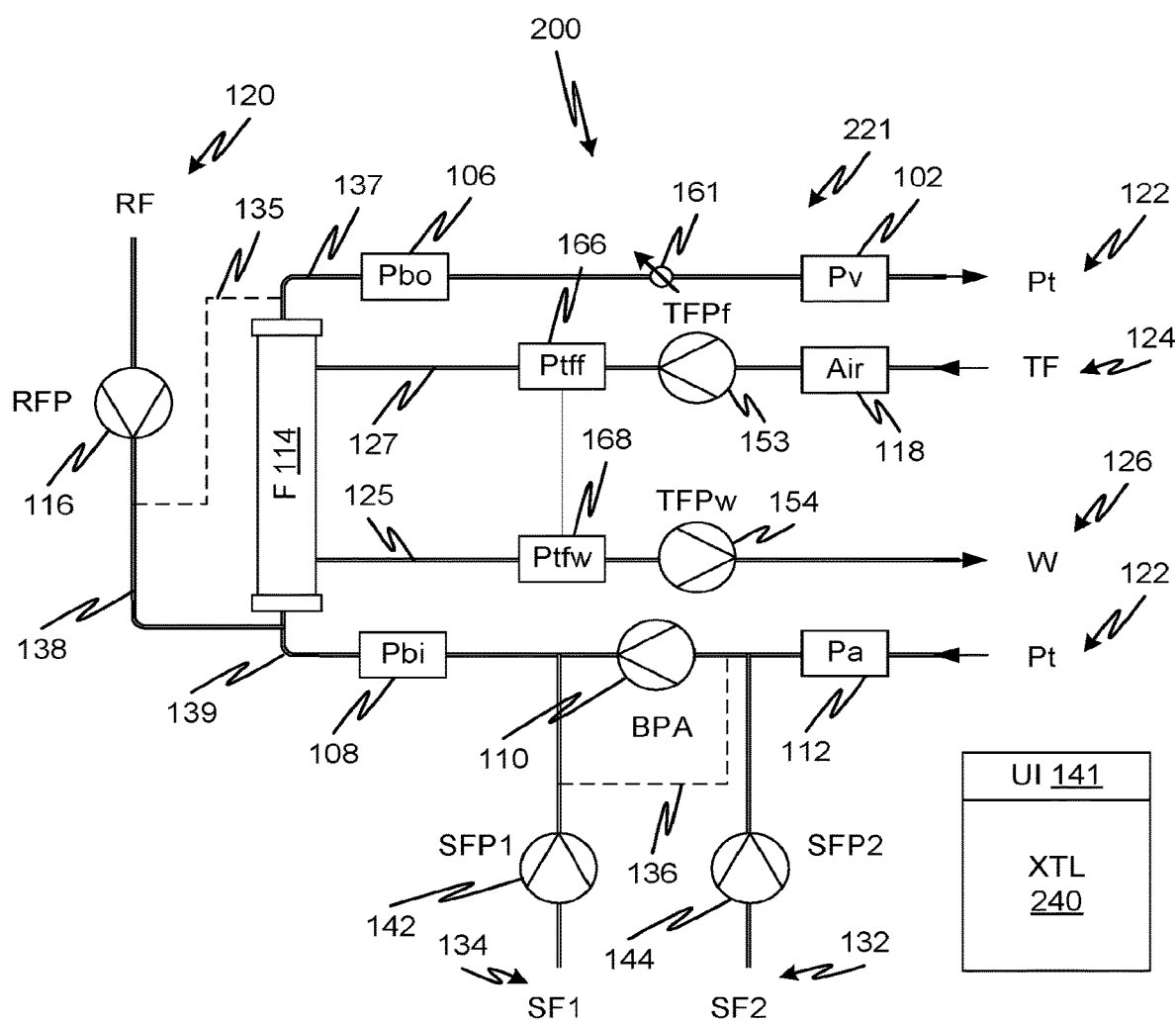
FIG. 3A shows a flow a blood treatment system that regulates the flow of treatment fluid into and out of a treatment device to generate a cumulative target ratio of fluid drawn or infused into a patient over the course of a treatment according to various embodiments of the disclosed subject matter.

FIG. 3A shows a flow a blood treatment system 200 that regulates the flow of treatment fluid relative to generate a cumulative target ratio of fluid drawn or infused into a patient 122 over the course of a treatment. The blood treatment system 200 regulates the flow of fluid in a fluid circuit 221 that includes an arterial blood line 139, a venous blood line 137, a fresh treatment fluid line 127 and a waste treatment fluid line 125. The net flow of fluid into or out of a patient or priming source/sink, at any given time, is determined by a current difference between the volume of treatment fluid pumped from a treatment device 114 (labeled F for filter) to the volume pumped into the treatment device 114 plus the volume pumped into the blood lines. Fluid (blood or priming fluid) is pumped from a source (e.g., patient 122 or priming fluid source—see later embodiments 3B et seq) into the treatment device 114 by an arterial blood pump 110 and flows from the treatment device 114 back to the patient 122 or priming fluid sink, drain, collection container, or recirculating container. As discussed elsewhere, for synchronization, the patient may be a priming fluid source/sink. For example, it may be a container of priming fluid to which priming fluid is returned thereby allowing endless recirculation and functioning as both source and sink of fluid. The illustrated configuration is common for dialysis systems, and may include all the typical incidents thereof, but differs specifically in that there are two treatment fluid pumps: a fresh treatment fluid pump 153, which pumps fresh treatment fluid 124 into the treatment device 114, and a waste treatment fluid pump 154, which pumps waste (spent) treatment fluid from the treatment device 114 to a drain 126. As above, control and sensing are provided by a controller 240 which may be of any form and again, typically, a programmable digital controller; an embedded computer. Treatment fluid 124 is pumped from a source through an air detector 118 through the treatment device 114, to the drain 126 (indicated by W for waste).

A replacement fluid 120 may be pumped into the arterial blood line 139 or the venous blood line 137 through a replacement fluid line 135 or 138, respectively (or both) for predilution, post-dilution. In alternative embodiments, the dilution may occur at a midpoint of the treatment device 114 as discussed above. The treatment device 114 may be adapted for any type of blood treatment including, but not limited to, dialysis, hemofiltration, hemodiafiltration, apheresis, adsorption, and hemoperfusion. Further supplemental fluids indicated by supplemental fluid 134 and supplemental fluid 132 may be pumped into the arterial blood line 139 by respective pumps, namely, supplemental fluid pump 142 and supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the arterial blood line 139 upstream of the arterial blood pump 110. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 110 and downstream of the treatment device 114. A venous blood pressure sensor 102 may detect pressure in the venous blood line 137 downstream of the venous blood pump 104 and upstream of the patient access 122. A fresh treatment fluid pressure sensor 166 indicates the pressure of treatment fluid downstream of the fresh treatment fluid pump 153 and a waste treatment fluid pressure sensor 168 indicates the pressure of waste treatment fluid upstream of the waste treatment fluid pump 154. The controller 240 receives signals from each of the arterial pressure sensor 112, blood inlet pressure sensor 108, blood outlet pressure sensor 106, and venous blood pressure sensor 102, the fresh treatment fluid pump 153, the waste treatment fluid pump 154, as well as an air detector 118 that is positioned to detect air in the fresh treatment fluid line 127. The controller 240 is also connected to control each of the arterial blood pump 110, replacement fluid pump 116, the supplemental fluid pump 142, the supplemental fluid pump 144, the fresh treatment fluid pump 153, and the waste treatment fluid pump 154. In embodiments, each pump contributing to flow balance may have a pressure sensor upstream of it to ensure that pressure compensated control of its speed can be provided. For example, an additional treatment fluid pump pressure sensor 119 shown in FIGS. 1A-1C may be provided here and in any embodiments as well. In embodiments, pressure sensors used for pressure compensated speed control are positioned such that they provide a reliable and consistent indication of pressure upstream of the respective pump or pumps. Thus, they may be positioned close or at least such that there are no intervening possible interferences such as tube lengths that could become kinked.

The blood treatment system 200 may also differ from a conventional system in having a controllable flow restrictor 161 that is controlled by the controller to regulate flow resistance in the venous blood line 137. The controllable flow restrictor 161 may be of any description. For example, it may be a progressive valve controlled by a servo or stepper motor. It may be a variable pinch clamp operatively engaged with a tubing length. It may be multiple fixed flow restrictors interconnected by a manifold that has valves to select a particular of the multiple flow restrictors.

In a treatment operation of blood treatment system 200, fresh treatment fluid pump 153 and waste treatment fluid pump 154 pump in the directions indicated by the respective arrowhead of each pump symbol, pump at rates controlled to balance the flow of blood in the arterial against the flow in the venous such that a net take-off of fluid (ultrafiltration) or a net infusion or ultrafiltration of fluid takes place as calculated by the controller 240 or per a command received by the controller 240. The instantaneous rate of ultrafiltration or infusion may vary during the course of a treatment. The controller 240 may be programmed to ensure that the net level of ultrafiltrate or infused fluid meets a prescribed target which may be stored by the controller 240. The pumping speeds required to achieve commanded flow rates may be determined by the controller 240 using data stored by the controller such as look up tables or formulas. The ratio of flow rate to pump speed (equivalently, the commanded flow rate) may be presented by this stored data to indicate target pump speeds in a relationship between pressure difference across the pump as well as flow rate; the pump curves. For example, in any of the embodiments, a look up table may have cells with pump speeds where columns and rows correspond to the independent variables of pressure at the pump inlet (or pressure differential across the pump for non-peristaltic pumps) and flow rate. Operating points may be interpolated or extrapolated for operating conditions that lie between or outside those corresponding to the cells or the formula or look-up table may provide interpolated or extrapolated values.

Note that in this or any of the embodiments, including those defined by the claims, the ratio of commanded pump speed to estimated flow may be given by a pump curve that is based on inlet pressure rather than outlet-inlet pressure difference depending on suitability for the type of pump used.

Treatment fluid 124 is pumped by fresh treatment fluid pump 128 at a predefined rate stored in the controller, which rate may be selected responsively to the blood flow rate or according to prescription. The replacement fluid 120 may be pumped at a rate controlled by the controller 240 by controlling the rate of replacement fluid pump 116. The supplemental fluid 134 may be pumped at a rate controlled by the controller 240 by controlling the pumping rate of supplemental fluid pump 142. The supplemental fluid 132 may be pumped at a rate controlled by the controller 240 by controlling the rate of supplemental fluid pump 144. Any combination of the replacement fluid 120, supplemental fluid 134, or supplemental fluid 132 may be included, or none of these. Each may be included or not along with the respective lines and pumps, in alternative embodiments. Flow control valves may be of any type as indicated above. As before, line 136 is present to indicate that in alternative embodiments, the supplemental fluids may enter the arterial blood line 139 upstream or downstream of the arterial blood pump 110.

Figure 4A:
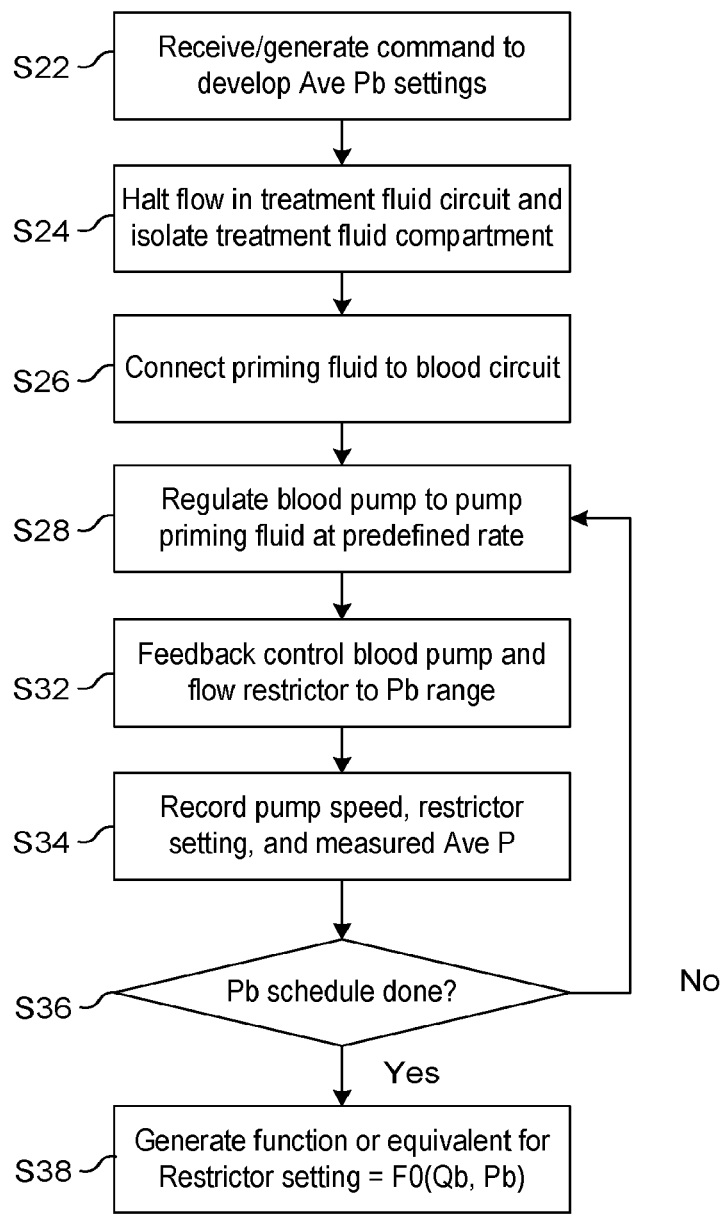
FIGS. 4A through 4D are flow charts for discussion of synchronization operations discussed with reference to FIGS. 3B through 3E according to various embodiments of the disclosed subject matter
Figure 4B:
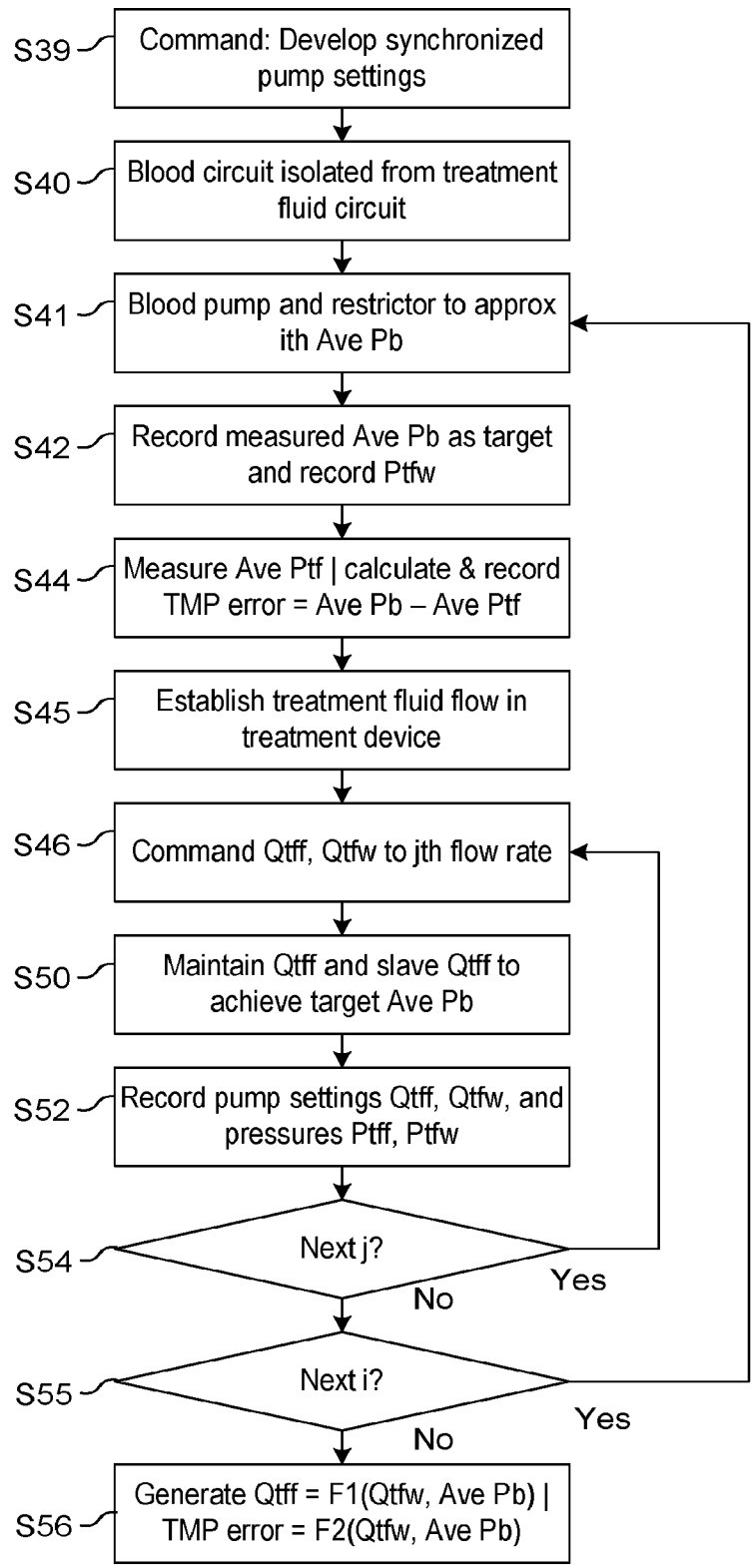
Figure 4C:
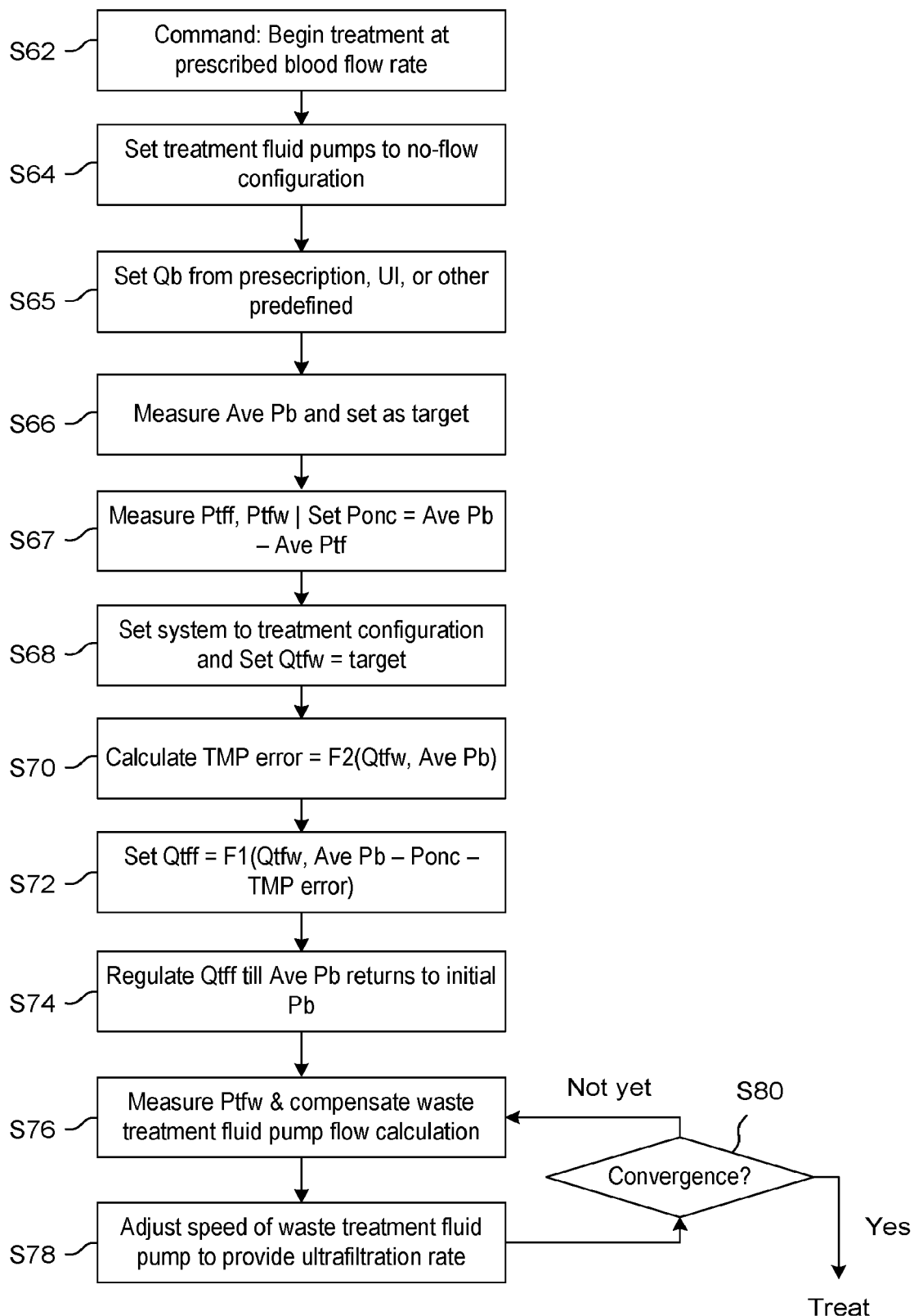
Figure 4D:
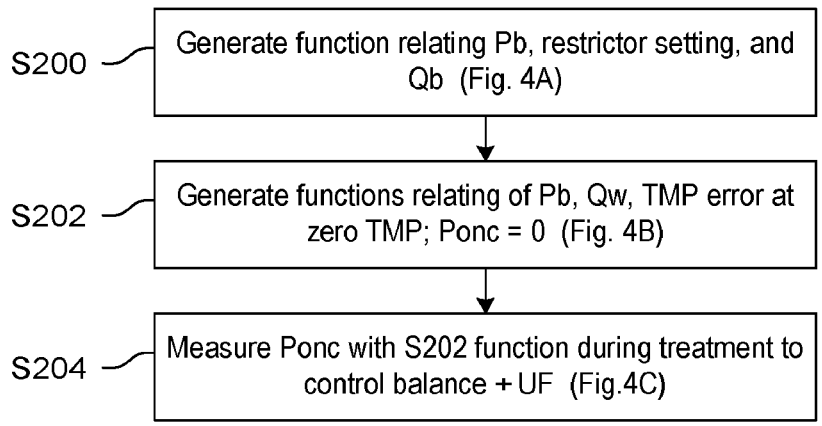

Referring now to FIG. 4D, which shows an overview of a method to be described below with reference to FIGS. 4A through 4C, for establishing and maintaining a condition of fluid balance by fresh treatment fluid pump 153 and waste treatment fluid pump 154 during a treatment based on the measurement of pressures on the treatment device 114 during a treatment. In a first stage S2, the controller determines flow rates and settings of controllable flow restrictor 161 and arterial blood pump 110 that establish a given average blood side pressure in treatment device 114. The process loops through a schedule of predefined blood side pressures each indicated by an average of readings from blood outlet pressure sensor 106 and blood inlet pressure sensor 108 Ave Pb and flow rates of waste treatment fluid pump 154 Qb commanded by the controller 240. For each combination and flow Qb and pressure Ave Pb, the controller 240 determines, through error control, a position of controllable flow restrictor 161 (restrictor setting) that establishes the given blood side pressure. A function or equivalent is finally generated to provide the restrictor setting as a function of Qb and Ave Pb. This function is then used in a following step S202 to generate functions that indicate a command flow rate for fresh treatment fluid pump 153 given a command flow rate of waste treatment fluid pump 154 and a blood side pressure Ave Pb.

At S202, the controller 240 loops through combinations of command flow rates of waste treatment fluid pump 154 and blood side pressures Ave Pb and determines a command flow rate of fresh treatment fluid pump 153 at which the treatment device 114 blood compartment pressure Ave Pb is maintained. This condition corresponds to zero convection between the blood and treatment fluid compartments. Any difference between average blood compartment pressure and average treatment fluid compartment pressure may be taken as a systematic error in pressure difference. A function or equivalent may be fitted to estimate the fresh treatment fluid pump 153 and error from a given commanded (prescribed, during treatment) flow rate of the waste treatment fluid pump 154 (taken as a desired or prescribed treatment fluid flow rate) and measured blood compartment pressure Ave Pb for a prescribed blood flow rate during a treatment. This fresh treatment fluid pump 153 rate will then correspond to zero flow in the absence of any oncotic pressure as existed during the procedure of S202 using fluids having the same osmotic potential such as the treatment fluid and priming fluid, for example. Note that both fluids can be the same fluid for the procedures of S200 and S202.

At S204, a treatment is performed in which the treatment device 114 blood compartment is filled with blood. In this case, the pressure difference between the blood and treatment fluid compartments Ave Pb and Ave Ptf are measured and stored to represent a difference caused by oncotic pressure due to the composition of blood. The oncotic pressure and error calculated from the function generated at S202 are used to determine a balanced flow rate Qtff of the fresh treatment fluid pump 153 given prescribed blood and treatment fluid flow rates during treatment. The process of flow chart of FIG. 4D summarizes the processes of flow charts 4A through 4C as indicated in each operation S200-S204 of FIG. 4D.

As shown further below, the of FIG. 4D is used for determining the fresh treatment fluid pump 153 and waste treatment fluid pump 154 flow rates for achieving a desired target fluid balance of the patient (net removal or infusion of a volume of fluid) through the maintenance of a target ratio and total displacement of these pumps. The method may be extended to account for the contribution of other sources of fluid, such as replacement fluid pump 116.

Figure 3B:
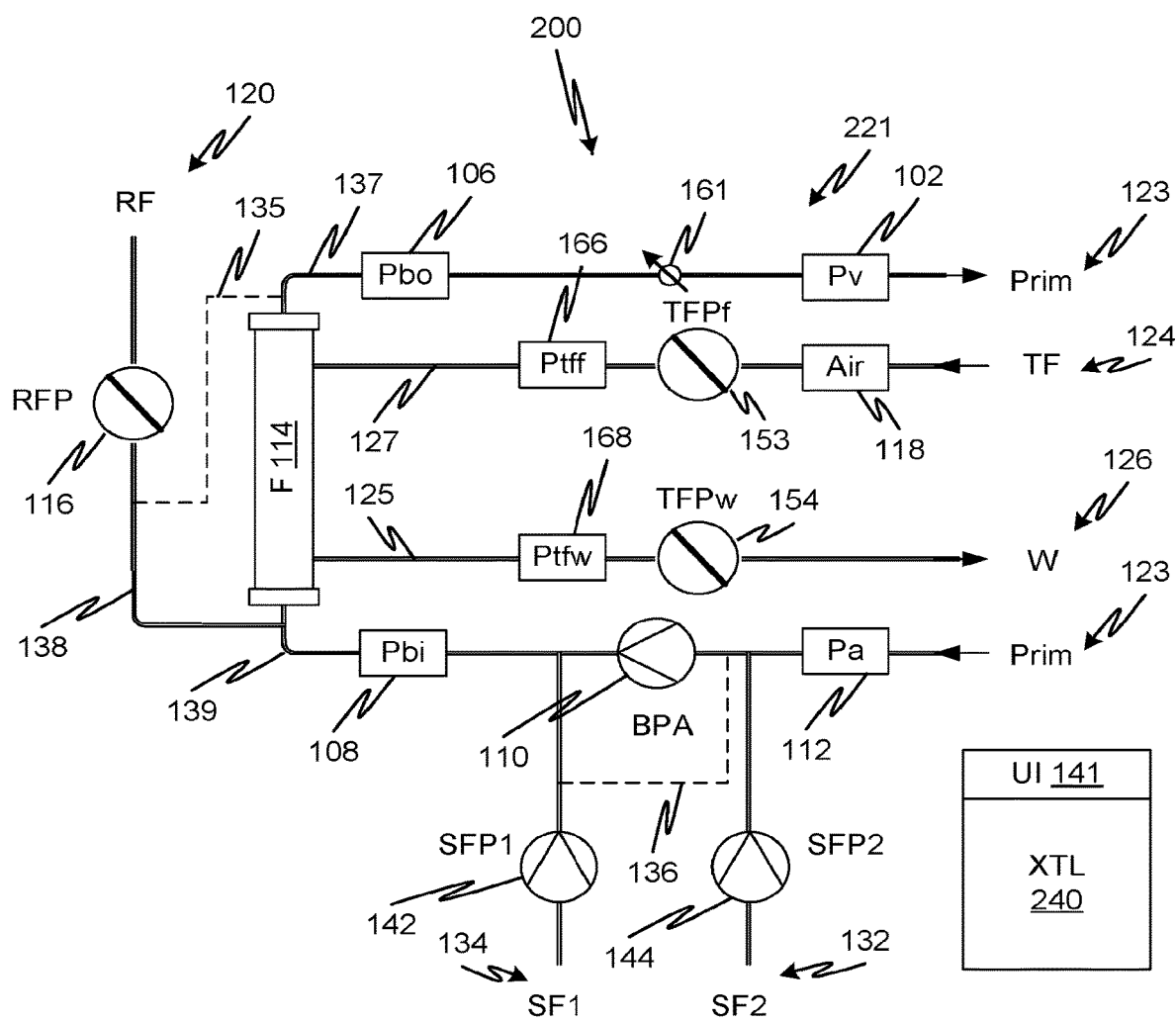
FIGS. 3B through 3E illustrate configurations of the blood treatment system of FIG. 3A at various phases of a synchronization sequence according to embodiments of the disclosed subject matter.

FIGS. 3B and 4A illustrate a configuration and operation of the blood treatment system 200 for determining conditions for the establishment of target fluid pressure Pb, typically priming fluid, on the blood side of the treatment device 114. Initially, before the establishment of the treatment fluid no-flow condition illustrated in FIG. 3B, the treatment fluid compartment of treatment device 114 would be filled in a priming operation. This may be done in a variety of ways including initially pumping treatment fluid or priming fluid through the waste treatment fluid line 125 and fresh treatment fluid line 127 and thereby through the treatment device 114. Then the configuration of FIG. 3B is established and the procedure of FIG. 4A is performed.

At S22 a command is received, or generated, by the controller 240 to begin a process for determining combinations of blood pump speed settings and/or flow restrictor settings selected to produce a predefined schedule of average blood pressure in the treatment device 114 during treatment operations which setting permit the establishment of a desired ultrafiltration rate.

See Table 1 infra. At S24, fresh treatment fluid pump 153 and waste treatment fluid pump 154 are halted. In further embodiments, the treatment fluid compartment of the treatment device 114 may be isolated, or further isolated, by closing control valves (not shown) such as pinch clamps, rather than shutting off pumps. In embodiments, the pumps are peristaltic pumps that occlude the line such that they prevent flow when halted. The halting of the fresh treatment fluid pump 153 and waste treatment fluid pump 154 is effective to block flow through, or from, the treatment fluid compartment of the treatment device 114 thereby isolating it except for a membrane of the treatment device. A source of priming fluid is connected S26 and the blood pump operated to establish a priming fluid flow in the blood compartment (blood side) of the treatment fluid device. Preferably priming fluid is provided in a container so that a recirculating flow can be established. During the priming operation, normally incident to the set-up of a blood treatment, a table of treatment fluid flow rates vs pressures is filled out as described below. An example is shown in Table 1. During the priming, the venous blood line 137 and arterial blood line 139 may be connected to priming fluid source/sink 123 recirculating through a container (not shown separately). The priming fluid can come from an inline source or a container for single-pass to a drain. Other arrangements for achieving flowing or recirculating priming fluid in the blood circuit of a blood treatment device are known and any of these may be implemented in the present embodiment.

TABLE 1

Schedule of flow rates and pressures for estimating restrictor setting

| Command Qb (ml/min) | Command Ave Pb (mmHg) | Measured Ave Pb (mmHg) | Measured Restrictor setting |
|---|---|---|---|
| 50 | 100 | 100.14 | AU |
| 50 | 250 | 250.59 | AU |
| 50 | 400 | 400.08 | AU |
| 200 | 100 | 100.89 | AU |
| 200 | 250 | 251.54 | AU |
| 200 | 400 | 398.71 | AU |
| 400 | 100 | 98.72 | AU |
| 400 | 250 | 248.46 | AU |
| 400 | 400 | 398.15 | AU |

At S28, after the controller 240 has implemented the above conditions it controls the arterial blood pump 110 to a predefined speed (working through each row in the table) and then at S32, modulates the speed of the blood pump and the adjustment of controllable flow restrictor 161 to achieve predefined pressure (second column of Table 1) of the priming fluid in the treatment device 114 as indicated by an average of the pressures in the venous blood line 137 and arterial blood line 139: Pba and Pbv, the average being denoted as Ave Pb. This is done in accord with a first pressure value in a schedule as illustrated by example in Table 1 (column 2). The regulation proceeds in a feedback control operation until the target Ave Pb is at least approximately established. The arterial blood pump 110 rate and setting of the controllable flow restrictor 161 that provides approximates the target predefined pressure on the treatment device 114 blood side (Ave Pb) may be recorded at S34. Also recorded is the actual measured value of the blood side pressure Ave Pb and the pumping rate Qb required to achieve that blood side pressure Ave Pb. The combination of blood pump rate and controllable flow restrictor setting are later used to establish an Ave Pb for the treatment filter represented in Table 1. The restrictor settings depend on the type of flow restrictor and may be, for example, steps or resistance of an encoder, force, or other unit. After The third through fifth column is generated, the data may be fit to a function or function-equivalent that relates the Ave Pb to the restrictor setting and blood pump flow rate. This process may be done at the beginning of a treatment or it may be performed for each configuration of the treatment apparatus and provided to the controller for use over multiple treatments.

The targeted set of Ave Pb may be selected to cover a realistic range of variability during a treatment when blood is flowing simultaneously with the treatment fluid. Table 1 shows as an example of such targets (100, 250, and 400 mmHg) that is suitable for a dialysis system but not generally limiting of the disclosed subject matter. The treatment device 114 blood side pressure may be taken by the controller 240 as an average of the pressures indicated by blood outlet pressure sensor 106 and blood inlet pressure sensor 108 which the controller 240 may calculate. The blood side pressure may also be taken as one or the other or some weighted average of the indications of the blood outlet pressure sensor 106 and blood inlet pressure sensor 108 which corresponds to a type of filter being used. The controller 240 may predict the arterial blood pump 110 speed corresponding to fixed target flow rate, vary the resistance or fix the resistance and vary the arterial blood pump 110, or vary both. The procedure repeats at S36 until all the target Pb values are established and the pump and restrictor settings determined and recorded. In the table, three Ave Pb values are generated and the settings required to achieve them recorded. At S38, a look-up table or formula is generated from the Ave Pb and the pump speed and flow restrictor settings so that they can be reestablished from the settings during a further synchronization operation and during treatment.

Figure 3C:
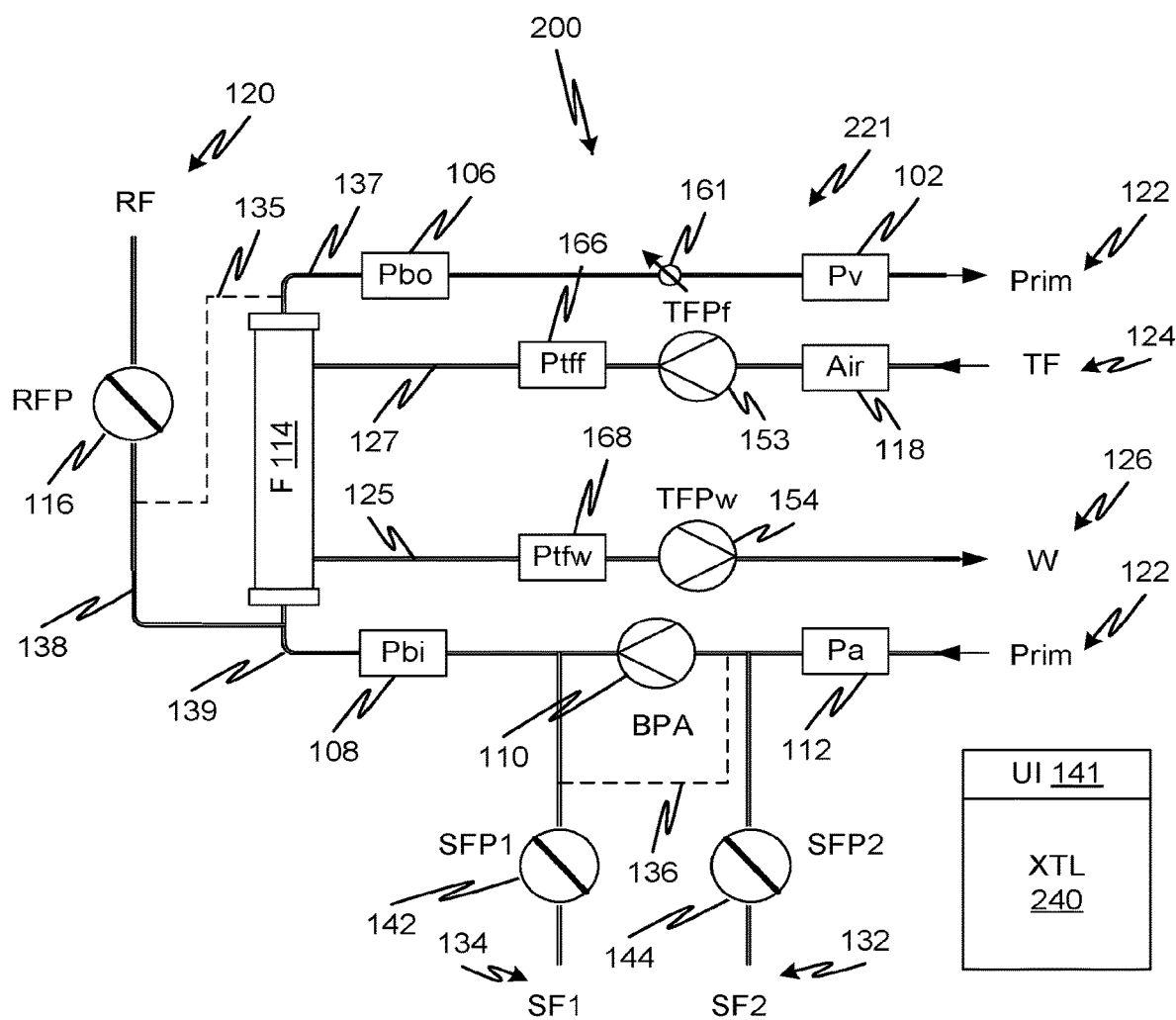

Referring now to FIGS. 3C and 4B, at S39 a command is received by the controller 240, or generated by it, to develop data that provides functions allowing blood treatment system 200 controller 240 to estimate pump settings for treatment. The command initiates the present procedure. See Table 2. The blood flow rate Qb and Ave Pb are the same as the schedule from the first two columns of Table 1. These represent target blood side flow rate Qb and pressure Ave Pb. The restrictor setting for each target blood side flow rate Qb and pressure Ave Pb is calculated from the function calculated at S38. However, the input for the Ave Pb is the measured input rather than the target. Since the function provides a restrictor setting that will provide a given flow rate and blood side pressure, there is no need at this point to feedback-regulate the restrictor setting to obtain the predefined Ave Pb. However, in other embodiments, this may be done and the derivation of the function for restrictor setting can be skipped.

Note that although the pressures of the dialysate and blood compartment are taken to be a combination (such as an average) of the values indicated by the pressures at the inlet and outlet pressure sensors for the respective compartment, it is possible to provide a pressure sensor on the blood treatment device, at least in some embodiments thereof, to measure a midpoint pressure directly. In a microtubular fiber-type dialyzer, for example, this could be done for the dialysate side by fitting a pressure measurement pod or tap on the dialyzer housing to measure dialyzer compartment pressure, but would be difficult for the blood compartment which is divided among multiple small channels. It is also possible to employ models of the pressure drop over the length of the blood treatment device to obtain a curve of pressure vs. displacement so that the average is a weighted average. Blood pressure may be taken from the treatment fluid compartment if the oncotic pressure is known. As disclosed herein, at any time, the oncotic pressure may be determined directly so that the controller can store the oncotic pressure and calculate the blood compartment pressure from the treatment fluid compartment pressure based on the oncotic pressure. A model can similarly be used if the convective flow exists between the blood and treatment fluid compartments (e.g., transmembrane flow) to allow the controller to numerically compensate for pressure difference caused by flow between the blood and treatment fluid compartments. Additionally, in embodiments, the pressure of the blood or treatment fluid compartment may be taken as one of the respective inlet and outlet pressures. This estimate can be refined based on a predefined hydraulic model that accounts for the pressure drop within the blood treatment device.

The parameters generated in the method of FIG. 4A and fitting of the function at S38 can be done once for multiple treatment cycles as when the configurations are the same and therefore the parameters are applicable to a current treatment cycle. This saves time during the priming operation at each treatment for the operation of FIG. 4B. At a point in the priming operation, a treatment apparatus, in priming mode, with the blood circuit filled with priming fluid and connected to recirculate (or otherwise permit the passage of priming fluid through it), a command is generated at S39 to perform a synchronization operation as now described. In S40, the blood circuit is isolated from the treatment fluid circuit.

TABLE 2

Schedule of flow rates and pressures for estimating Qtff and TMP error

| Cmd Qb (ml/min) | Target Ave Pb (mmHg) | Calc Restrictor setting | Measured Ave Pb (mmHg) | Measured Ave Ptf (mmHg) | Calc TMP error (mmHg) | Pump setting Qtff (ml/min) | Pump setting Qtfw (ml/min) |
|---|---|---|---|---|---|---|---|
| 50 | 100 | AU | 100.00 | 100.00 | 1.48 | 101.48 | 100 |
| 50 | 250 | AU | 249.00 | 249.00 | 0.06 | 249.06 | 250 |
| 50 | 400 | AU | 401.00 | 401.00 | 0.16 | 401.16 | 400 |
| 200 | 100 | AU | 101.00 | 101.00 | 1.97 | 102.97 | 100 |
| 200 | 250 | AU | 249.00 | 249.00 | −2.39 | 246.61 | 250 |
| 200 | 400 | AU | 401.00 | 401.00 | 1.52 | 402.52 | 400 |
| 400 | 100 | AU | 100.00 | 100.00 | 2.26 | 102.26 | 100 |
| 400 | 250 | AU | 251.00 | 251.00 | −2.36 | 248.64 | 250 |
| 400 | 400 | AU | 399.00 | 399.00 | −0.74 | 398.26 | 400 |

At S41, the blood pump and restrictor are controlled to establish an ith Ave Pb in the schedule of multiple Ave Pb values. The restrictor 161 setting can be established quickly using the function calculated at S38 or it can be determined for the current Qb and target (ith) Ave Pb by feedback control. The latter may take longer which is the advantage of fitting the function at S38 at a time prior to treatment and only once for multiple treatments. Note also that although the present procedure of FIG. 4B may be done immediately prior to treatment, during a priming stage thereof, it can also be done at other times such that the function generated thereby (See S56 infra) is still valid for use during a treatment. For example, fluid circuit itself may be the same. However, it is advantageous that it be done immediately prior to treatment because wetting the fluid circuits and letting them stand, especially if portions are compressed by control valves and pumping actuators, may make the conditions during treatment different from those during the synchronization process and thereby reduce the applicability of the function fit at step S56 during treatment.

The regulating to achieve an actual ith value in the schedule of Ave Pb values does not require high precision and an approximation sufficient to ensure that a variety of conditions are obtained and used to fit an estimation function at S56 may be used. A value that is close may be determined by comparison of a current measured Ave Pb (indicated by the average of blood outlet pressure sensor 106 and blood inlet pressure sensor 108) with a stored range of errors may be used by the controller 240 to indicate that the current actual measured Ave Pb is close enough to the ith value of Ave Pb stored in the schedule. At that point, at S42, the actual Ave Pb determined from the average of (Pbv) blood outlet pressure sensor 106 and (Pba) blood inlet pressure sensor 108 may be stored in the data table subsequently to be used for the fitting of a predictive function or function-equivalent. Note that in further embodiments, values of the blood inlet and outlet pressures themselves may be stored. Also, the average may represent a weighted average rather than a simple average that is indicated for the particular type of treatment device. The sparse data may be fitted to a smooth function to allow estimation of commanded flow rates for conditions during treatment. The table of conditions may be stored after reduction to a function or function-equivalent such as a dense lookup table. They may also be stored in unreduced form as) as raw sparse data and extrapolation and/or interpolation for instant conditions interpolation computed according to treatment conditions. The table may be sparse matrix, that is, not every cell necessarily has a value.

At S44, an average Ptf (Ave Ptf) is calculated and the difference between Ave Pb and Ave Ptf recorded. This difference provides an estimate of systematic error in the TMP that can be used for determining TMP at other conditions including those during treatment. Now for each of the original target Ave Pb values the controller has stored a measured Ave Pb and a measured Ave Ptf as well as an error indicating the difference. In embodiments, the error is stored but not the Ave Ptf and in other embodiments, all raw data may be stored including Pba, Pbv, Ptff, Ptfw.

At S45, the fresh treatment fluid pump 153 and waste treatment fluid pump 154 and control valves (again, if present) are set to pump fluid through the treatment device 114 as in a treatment. At S46, a jth target flow rate is established for the waste treatment fluid pump 154 and fresh treatment fluid pump 153 by operating at speeds calculated from a standard conversion (i.e. a predefined ratio of pump speed to expected flow rate, rather than measured, pressure condition for applying a pump curve) to for the jth target flow rate as indicated by example in Table 1 (Qtfw flow). At S50, the controller 240 regulates the speed of the fresh treatment fluid pump 153 to bring the current measured Ave Pb toward the target Ave Pb, recorded at S41, by adjusting the speed of the fresh treatment fluid pump 153. This brings about the synchronization of the fresh treatment fluid pump 153 and waste treatment fluid pump 154. In embodiments, a flow through fresh treatment fluid pump 153 is adjusted until synchronization is established, but either pump could be controlled as the master and the other as the slave. Another alternative is a combination approach, where both pumps take turns being adjusted to achieve synchronization. The pressure and pump settings identified in Table 1 are recorded at S52. This is repeated by looping through j and i at S54 and S55 until all conditions have been generated and the corresponding values in Table 1 recorded. Thus, a matrix of combinations of Ave Pb and Qtfw plus attending data for each combination including the Qtff speed, and pressures indicated by fresh treatment fluid pressure sensor 166 (Ptff) and waste treatment fluid pressure sensor 168 (Ptfw) are recorded in a data store of the controller 240.

At S56, the data recorded at S44 and S52 may be fitted to a look up table or fitted to a function to be used for control which maps a given combination of Ave Pb and Qtfw to an output Qtff and TMP error. By fitting to a look up table it is meant that values may be interpolated between cells of the table by a fitted curve or surface and a table many more cells generated to allow rapid use of the fitted data for looking combinations of Ave Pb and Qtfw that were not used for the procedure of FIG. 4B. Calculated values of Ptff and Ptfw may also be yielded by a function or look up table to provide a validity check on the estimate. That is, the controller 240 may also, or alternatively, generate an error signal if one or both of the Ptff and Ptfw is beyond a predefined range from the output Qtff.

The values of Ptff and Ptfw may provide a mechanism for compensating the input value of Qtfw and the commanded speed for fresh treatment fluid pump 153, Qtff. The flow rates commanded during treatment based on the function derived from Table 2 may adjust for differences between the pressure at the respective inlets of the waste and fresh treatment fluid pumps corresponding to the function and those existing at the time of treatment when balanced flow is implemented.

During a treatment, given an average blood pressure Ave Pb indicated by the average of blood outlet pressure sensor 106 and blood inlet pressure sensor 108, for a commanded blood flow rate Qb, and a commanded treatment fluid flow rate of waste treatment fluid pump 154 Qtfw, a speed of the fresh treatment fluid pump 153 Qtff is automatically generated which is assured to provide the precise 1:1 flow synchronization of the fresh treatment fluid pump 153 and waste treatment fluid pump 154 at those operating conditions. The controller 240 then operates the fresh treatment fluid pump 153 at the output speed. This speed may be further refined to compensate for differences between the pump inlet pressure conditions when the map of conditions was created versus the conditions when the function is called upon to estimate the speed of the fresh treatment fluid pump 153. FIG. 4C provides the implementation details that further refine this process in order to provide precise balancing of the Qtff and Qtfw and further permit the implantation of a prescribed ultrafiltration rate.

Figure 3D:
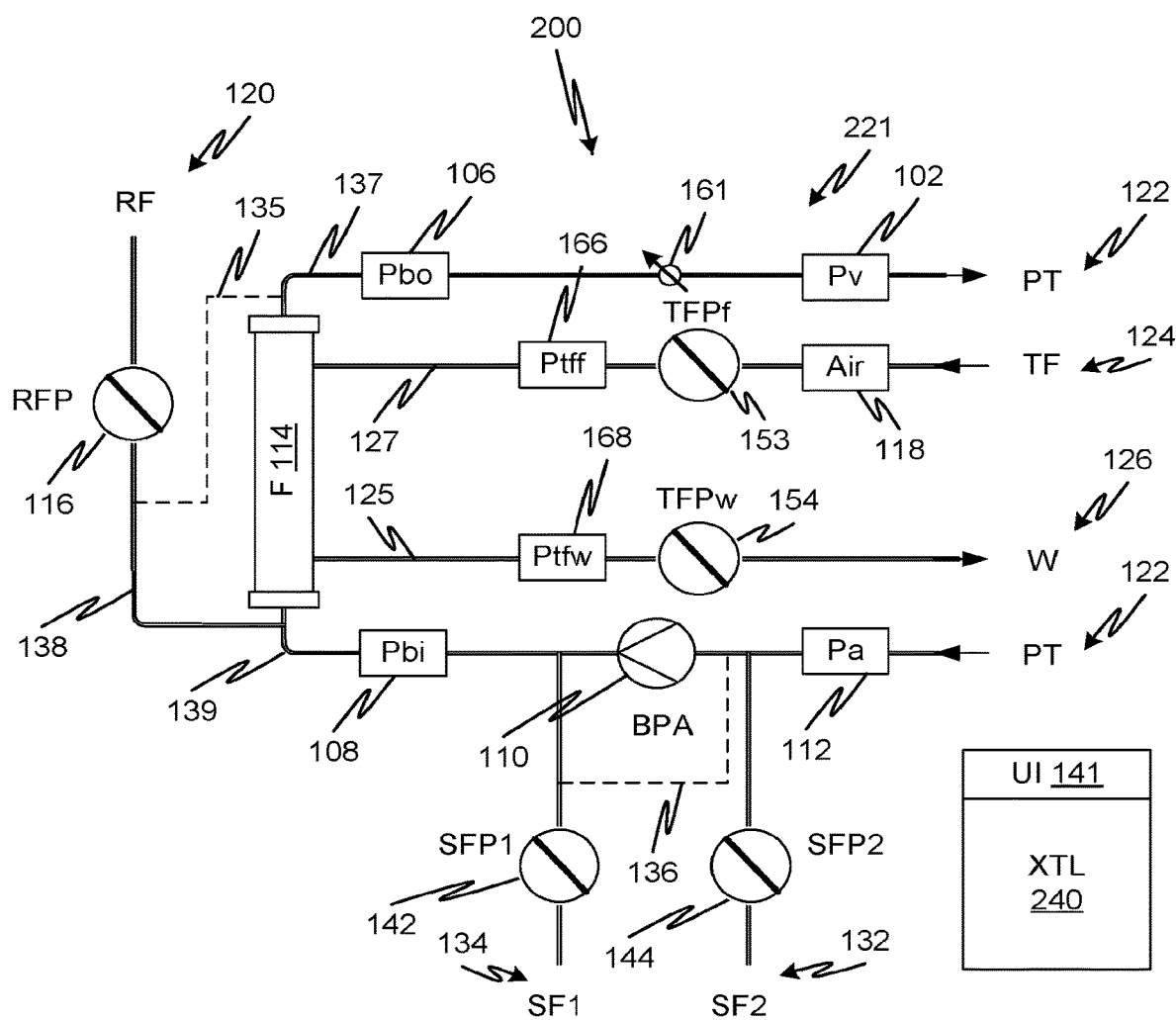

Referring now to FIGS. 3D and 4C, at S62, a command is received by, or generated by, the controller 240 to perform a treatment. During a treatment, blood is pumped by arterial blood pump 110 with fresh treatment fluid pump 153 and waste treatment fluid pump 154 turned off. The treatment fluid circuit may be filled with priming fluid or treatment fluid at this point which is presumed to be at the beginning of a treatment, however it can be repeated at other times during a treatment in order to reestablish balanced operating conditions for the treatment fluid pumps.

Figure 3E:
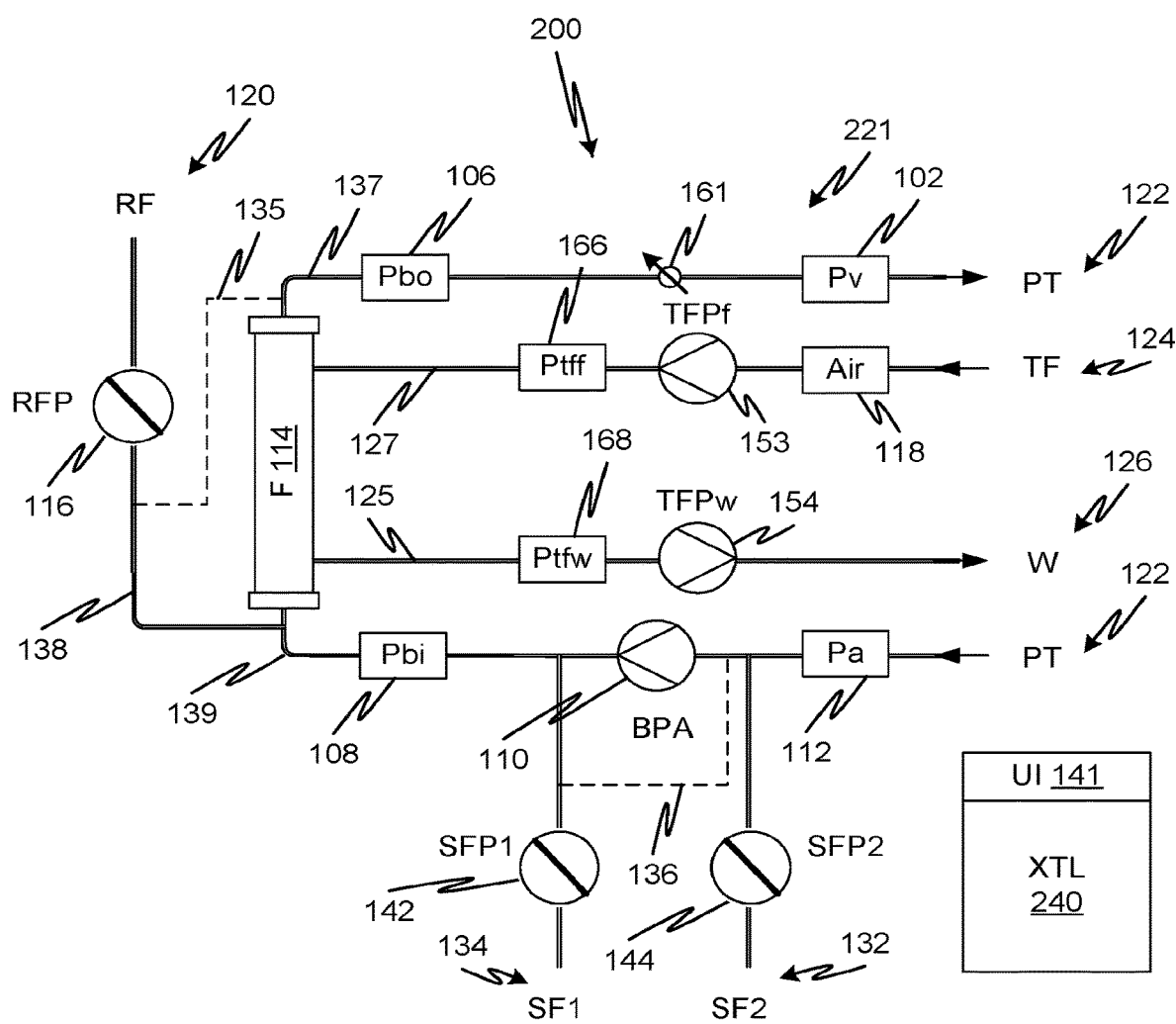

The treatment fluid no-flow configuration is established at S64. The prescribed blood flow rate Qb is established by controlling the arterial blood pump 110 at S65. At S66, the Ave Pb is calculated from blood outlet pressure sensor 106 and blood inlet pressure sensor 108 and stored. This measured Ave Pb is stored as a target Ave Pb. Next, at S67, the difference between the target Ave Pb and Ave Ptf may be calculated from the blood outlet pressure sensor 106, blood inlet pressure sensor 108, fresh treatment fluid pressure sensor 166, and waste treatment fluid pressure sensor 168 readings. This may be recorded as a measure of the oncotic pressure Ponc which biases the transmembrane pressure TMP relative to the condition where blood and treatment fluid compartments contain fluids with the same osmotic potential. As indicated elsewhere herein, the oncotic pressure may be used for a number of functions. Referring now also to FIG. 3E, at S68 the controller 240 selects a speed of the waste treatment fluid pump 154, for example based on a stored prescription entered by an operator or retrieved from an external source, such as a patient treatment profile database. At S70, the TMP error is calculated from the function fitted at S56 of FIG. 4B based on Qtfw and target Ave Pb. At S72, the fresh treatment fluid pump 153 speed Qtff is calculated based on the function fitted at S56 based on Qtfw and target Ave Pb reduced by the TMP error calculated at S70 and the oncotic pressure Ponc calculated at S67. This corrects the estimate of Qtff for the TMP error and the oncotic pressure caused by the blood. The fresh treatment fluid pump 153 is commanded to the calculated speed Qtff and the controller 240 at S74 adjusts the speed of fresh treatment fluid pump 153 Qtff such that current measured Ave Pb is restored to the initial target Ave Pb. Once the fresh treatment fluid pump 153 and of treatment fluid pump 154 are thus synchronized, the pressure indicated by waste treatment fluid pressure sensor 168 may then be used at S76 to determine the flow rate, with compensation based on inlet pressure, and the speed of the of treatment fluid pump 154 adjusted to provide a desired ultrafiltration rate or infusion rate at S78, as prescribed. Since the speed adjustment may affect the inlet pressure of the of waste treatment fluid pump 154, the pump compensation may be recalculated, the pump speed adjusted again until it stops changing by looping through S80. The fresh treatment fluid pump, at any time, may be adjusted in response to a measured inlet pressure, for example using a pressure sensor such as 119.

The synchronization process of FIGS. 4B and 4C can run again based on any of a variety of different criteria, automatically, under control of the controller. For example, if the blood or treatment fluid flow rates is/are changed, the ultrafiltration or infusion rate is changed, a period of time has elapsed, a component is changed such as a treatment device swap, a change in pressure at any point, access patency change, patient position change, and others.

The measured oncotic pressure may be stored by the controller and used to provide multiple functions. In embodiments, the oncotic pressure can be used to estimate a patient's fluid level in order to permit a more accurate determination of the required ultrafiltration. The oncotic pressure may be combined with other data to improve the estimate of the patient's fluid level, for example hematocrit can be measured directly. In embodiments, the controller may be programmed to calculate oncotic pressure at multiple times during a treatment and to combine the oncotic pressure with other data such as hematocrit to generate adjustments to a prescribed ultrafiltration rate that was previously stored in the controller. In addition, a predicted and currently estimated—estimated from measured data such as oncotic pressure and hematocrit—fluid level may be generated as well. The predicted level may be calculated from the implemented ultrafiltration rate over time which yields a predicted total fluid removed. The controller may alternatively or further be programmed to generate a signal indicating a mismatch between a prescribed ultrafiltration rate and a current fluid level of the patient with accounting for the remaining time left in a treatment. Here, we use the term oncotic pressure to refer to the pressure difference due to all the differences in the compositions of the blood and treatment fluid including proteins, middle molecules, electrolytes, and any other components that may contribute to diffusion potential.

In any of the embodiments where blood side pressure of the blood treatment device is used as a target to bring the fresh treatment fluid pump to represent a state of zero ultrafiltration (equivalently, zero transmembrane flow or zero transmembrane pressure), in further embodiments, the non-blood side pressure of the treatment device may instead be stored and used in the same manner. That is Ave Pb may be replaced with Ave Ptf may for purposes of characterizing the zero ultrafiltration condition. This does not include the measurement of oncotic pressure or TMP error. It has been determined that feedback controlling to achieve a target Ave Ptf to achieve synchronization converges more rapidly, under certain conditions and in certain types of systems, than feedback controlling on Ave Pb.

Figure 5:
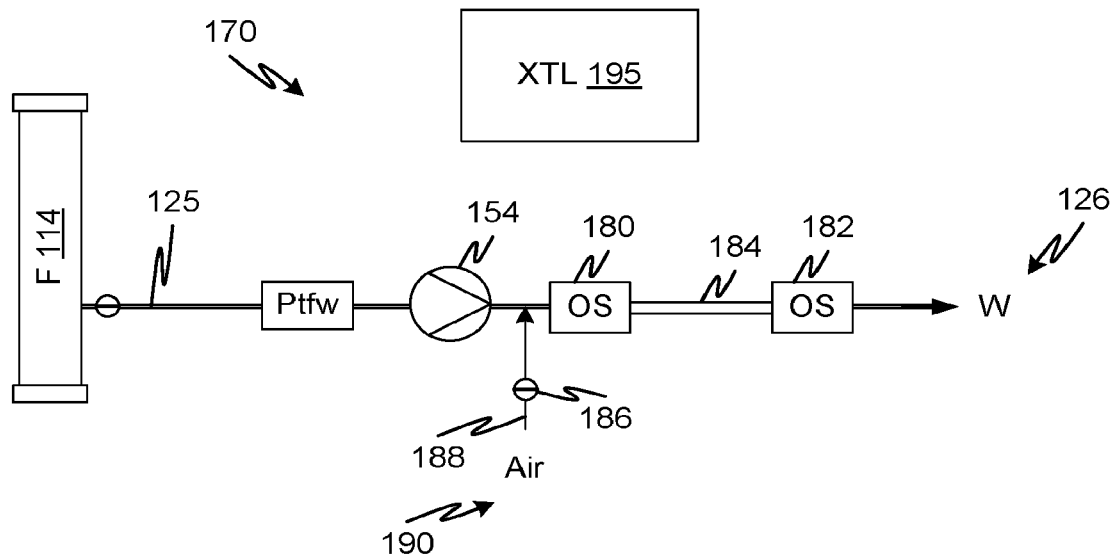
FIG. 5 shows a flow meter adapted for use in blood treatment systems according to embodiments of the disclosed subject matter.
Figure 6A:
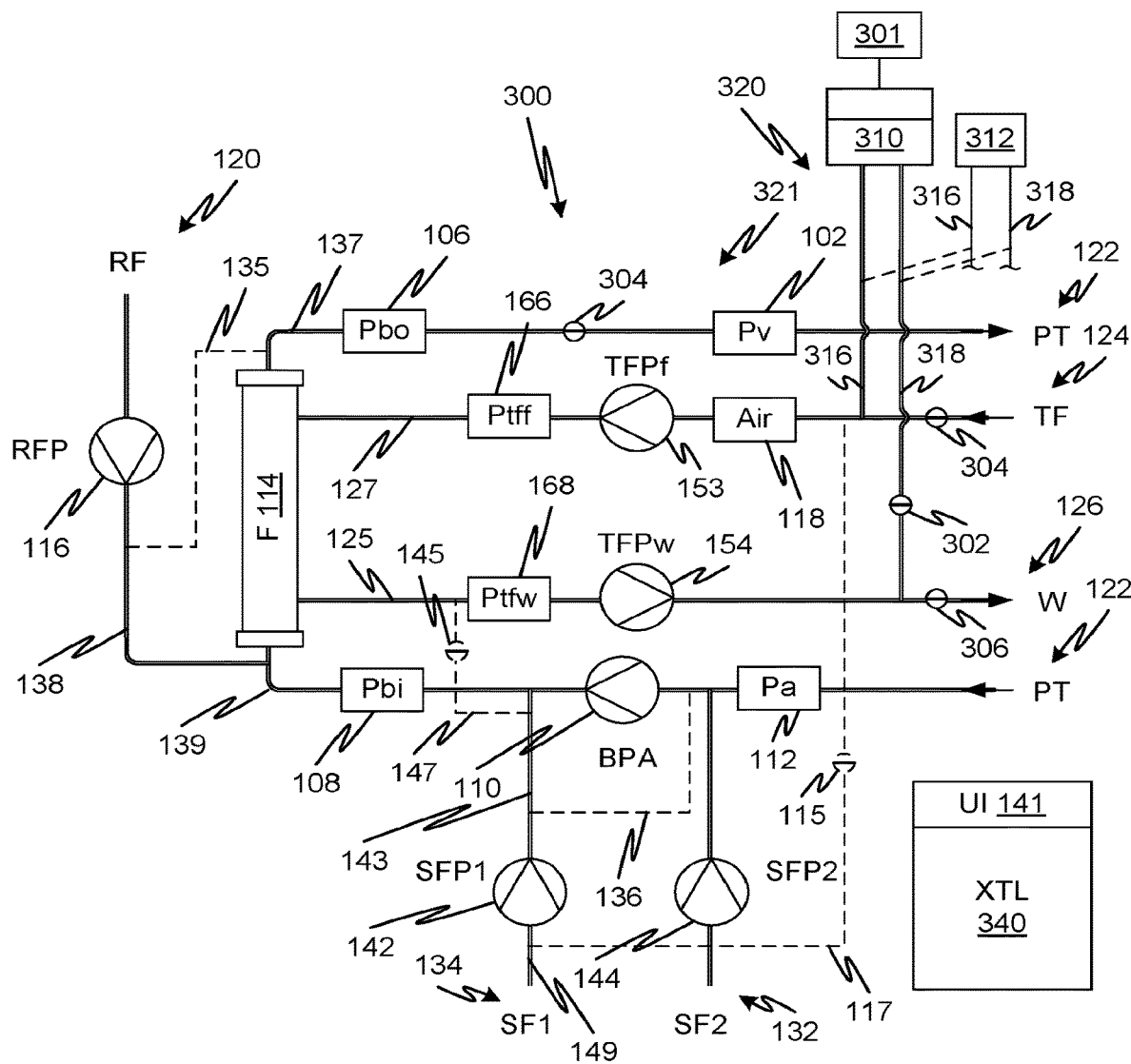
FIGS. 6A and 6B show a blood treatment system that regulates the flow of treatment fluid to generate a cumulative target ratio of fluid drawn or infused into a patient over the course of a treatment in a treatment mode and a synchronization mode, respectively, according to further embodiments of the disclosed subject matter.
Figure 6B:
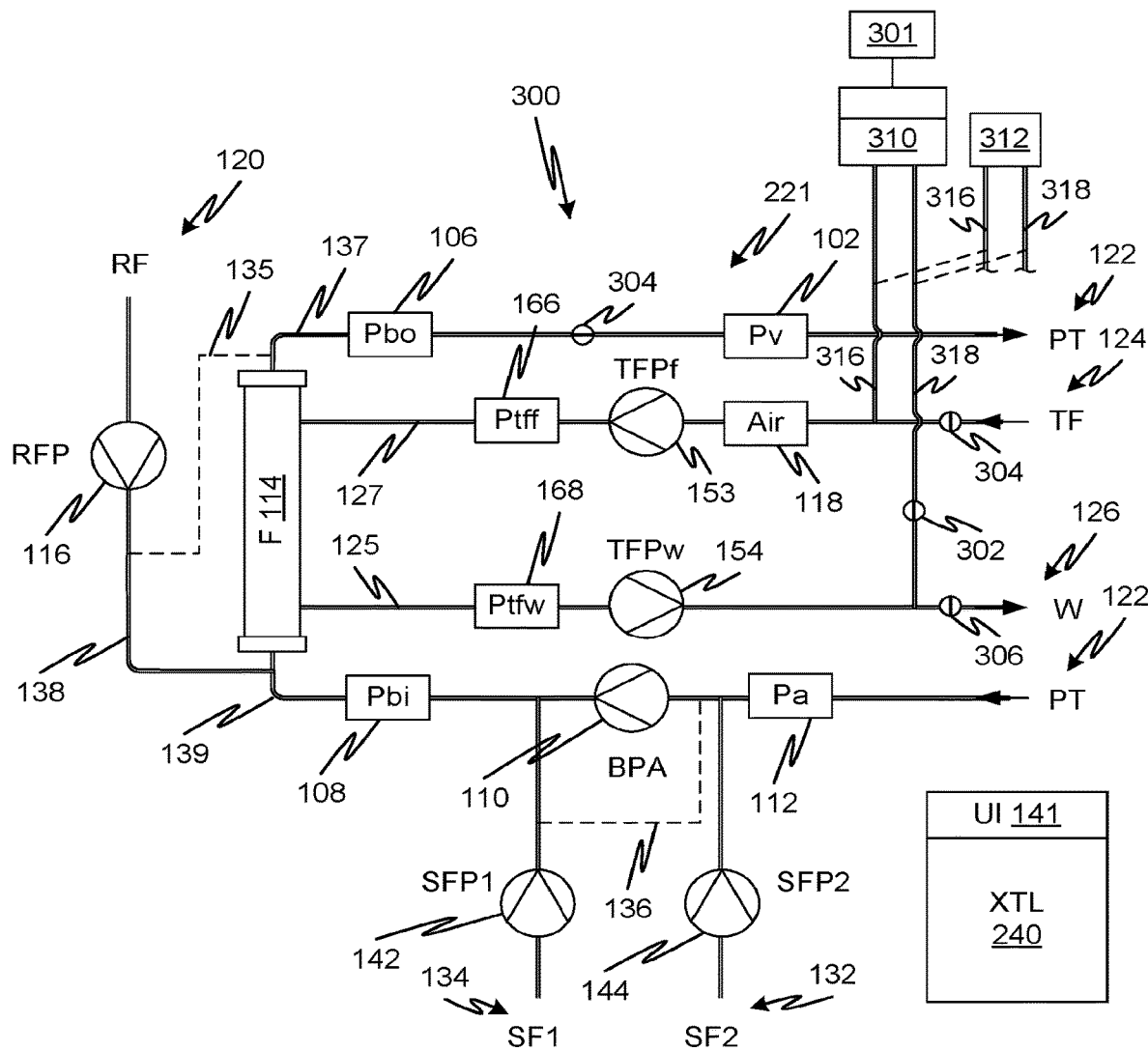

FIG. 5 shows a flow meter 170 that can be used as a reference for synchronizing pumps to a common flow rate standard. A tube segment 184 that is manufactured to precise tolerances and has a known volume and length is positioned in the waste treatment fluid line 125. An air line 188 is connected to a source of pressurized air 190 and further connected to the waste treatment fluid line 125 through a control valve 186 connected to be controlled by a controller 195. The controller 195 injects a predefined bolus or air into the waste treatment fluid line 125 which is carried past two optical sensors 180 and 182 arranged in series. The optical sensors detect the bolus of air and convey the signals to the controller 195 which calculates a time difference—a time-of-flight. With the predefined length and diameter of the tube segment 184, plus the known characteristics of fully developed flow for the fluid therein, the controller 195 can calculate a volume flow rate. Since the fluid carried by waste treatment fluid line 125 is disposed of to a drain 126, there is no detriment injecting air into the waste treatment fluid line 125. Such a flow measurement device, or some other, may be employed advantageously to provide a further estimate of the flow rates on which the pump pressure compensations are based. In addition, an indication of absolute flow rate of a pump may be used by the controller to detect an anomalous state of the system and therefore a potential source of error in the flow synchronization mechanisms employed to achieve balance. The flow rate of a single pump, for instance the waste treatment fluid pump, may be sufficient since the synchronization process accurately FIGS. 6A and 6B show a blood treatment system 300 in which fresh treatment fluid pump 153 and treatment fluid pump 154 are synchronized, to provide a control parameter that can be used as a basis for fluid flow balance. To do so, a synchronization operation is performed as in other embodiments, but in this case, it is done without establishing a fixed volume flow through the treatment device 114 as in the embodiments discussed above, for example as described with reference to FIGS. 1A-1E. As will be observed, a series flow of treatment fluid is established in the treatment fluid circuit without a need to block flow in the blood circuit. In the blood treatment system 100, the flow of treatment fluid was blocked to form a fixed volume channel between the blood pumps through the blood treatment device 114. Here, instead, a direct connection between the treatment fluid pumps is established by closing the circuit on the source/sink side of the treatment fluid circuit. In first embodiments, the volume of the direction connection channel is fixed and pressure is measured to indicate a mismatch in the pumping rates. In second embodiments, a level of treatment fluid volume in an accumulator provides in indication of flow mismatch. The approach of closing the fluid circuit on the source/sink side of the treatment fluid circuit may be advantageous for a variety of reasons not least of which is that it avoids halting flow in the blood circuit which reduce the risk of blood clotting. During priming or during treatment, to implement a synchronization operation, a closed loop is temporarily formed to circulate treatment fluid and the net uptake or loss of fluid into the closed loop, which represents fluid passing through the treatment device 114 into the closed loop, is detected and the pumps regulated to bring the net rate of uptake or loss to zero, thereby synchronizing the fresh treatment fluid pump 153 and of treatment fluid pump 154. The detection of net uptake or loss may be accomplished by measuring pressure in the closed loop with a pressure measurement device or pressure sensor (such as a pressure transducer) 312 or by measuring the weight gain of a fluid accumulator 310 (also referred to as an accumulator) in the loop using a scale 301. Instead of a scale, a level indicator in a fixed volume chamber may be used as will be evident from the further description below.

FIG. 6A shows a flow a blood treatment system 300 that regulates the flow of treatment fluid to generate a cumulative target ratio of fluid drawn or infused into a patient over the course of a treatment. A blood treatment system 300 regulates the flow of fluid in a fluid circuit 321 that includes an arterial blood line 139, a venous blood line 137, a fresh treatment fluid line 127 and a waste treatment fluid line 125. The net flow of fluid into or out of a patient, at any given time, is determined by a then-instant difference between the volume of treatment fluid pumped from a treatment device 114 to the combined volume pumped into the both the treatment device 114 and the blood lines. Blood is pumped from a patient 122 (conventionally, via a patient access) into the treatment device 114 by an arterial blood pump 110 and flows from the treatment device 114 back to the patient 122. The illustrated configuration is common for dialysis systems, and may include all the typical incidents thereof, but differs specifically in that there are two treatment fluid pumps: a fresh treatment fluid pump 153, which pumps fresh treatment fluid 124 into the treatment device 114, and a waste treatment fluid pump 154, which pumps waste (spent) treatment fluid from the treatment device 114 to a drain 126. Control and sensing are provided by a controller 340 which may be of any form but typically a programmable digital controller; an embedded computer. Treatment fluid 124 is pumped from a source through an air detector 118 through the treatment device 114, to the drain 126 (indicated by W for waste).

A replacement fluid 120 may be pumped into the arterial blood line 139 or the venous blood line 137 through a replacement fluid line 135 or 138, respectively (or both) for predilution, post-dilution. In alternative embodiments, the dilution may occur at a midpoint of the treatment device 114, for example by splitting the treatment device 114 into two parts and providing a junction between them. The treatment device 114 may be adapted for any type of blood treatment including, but not limited to, dialysis, hemofiltration, hemodiafiltration, apheresis, adsorption, hemoperfusion, and blood oxygenation. Further supplemental fluids indicated by supplemental fluid 134 and supplemental fluid 132 may be pumped into the arterial blood line 139 by respective pumps, namely, supplemental fluid pump 142 and supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the arterial blood line 139 upstream of the arterial blood pump 110. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 104 and downstream of the treatment device 114. A venous blood pressure sensor 102 may detect pressure in the venous blood line 137 downstream of the venous blood pump 104 and upstream of the patient access 122. An inlet treatment fluid pressure sensor 166 indicates the pressure of treatment fluid downstream of the fresh treatment fluid pump 153 and a waste treatment fluid pressure sensor 168. The controller 340 receives signals from each of the arterial pressure sensor 112, blood inlet pressure sensor 108, blood outlet pressure sensor 106, and venous blood pressure sensor 102, the fresh treatment fluid pump 153, the waste treatment fluid pump 154, as well as an air detector 118 that is positioned to detect air in the fresh treatment fluid line 127. The controller 340 is also connected to control each of the arterial blood pump 110, replacement fluid pump 116, the supplemental fluid pump 142, the supplemental fluid pump 144, the fresh treatment fluid pump 153, and the waste treatment fluid pump 154.

The blood treatment system 200 also differs from a conventional system in having a treatment fluid branch loop closer 320 that includes an outgoing loop line 316 and an incoming loop line 318, either an accumulator 310 weighed by the scale 301, or a pressure measurement device 312, as well as a loop control valve 302, a fresh treatment fluid control valve 304 and a waste treatment fluid control valve 306. In FIG. 6A, the loop control valve 302, the fresh treatment fluid control valve 304 and the waste treatment fluid control valve 306 are set in a treatment mode to allow fresh treatment fluid to circulate through the treatment device 114 and to permit waste treatment fluid to pass to the drain 126. The treatment fluid branch loop closer 320 is not in the loop as determined by the closed position of the waste treatment fluid control valve 306. Thus, fluid passes directly from the treatment fluid 124 to the drain 126 by way of the treatment device 114 and the fresh treatment fluid pump 153 and waste treatment fluid pump 154. Instead of a scale 301 a fluid level detector may be used to indicate changes in fluid volume of the accumulator 310.

In a synchronization mode shown in FIG. 6A, the treatment fluid source 124 and the drain 126 are cut off by the closed positions of fresh treatment fluid control valve 304 and waste treatment fluid control valve 306. The open position of 6A, the loop control valve 302 causes a closed loop to be formed by the venous blood line 137, arterial blood line 139, outgoing loop line 316, accumulator 310, and the incoming loop line 318. In the alternative embodiment, the loop includes the pressure measurement device 312 instead of the accumulator 310. When the fresh treatment fluid pump 153 and waste treatment fluid pump 154 are out of synch, the scale 301 or the pressure sensor 312 will indicate a rise or fall in weight or pressure over time and the controller 340 changes one of the fresh treatment fluid pump 153 and waste treatment fluid pump 154 into synch. The data converting pump flow to pump speed can thereby be adjusted so that fluid balance is better maintained during treatment.

In a treatment operation of blood treatment system 300, fresh treatment fluid pump 153 and waste treatment fluid pump 154 pump in the directions indicated by the respective arrowhead of each pump symbol, pump at rates controlled to balance the flow of treatment fluid in the fresh treatment fluid line 127 against the flow of blood in the venous blood line waste treatment fluid line 125 such that a net take-off of fluid (ultrafiltration) or a net infusion of fluid takes place as calculated by the controller 340 or per a command received by the controller 240. The instantaneous rate of ultrafiltration or infusion may vary during the course of a treatment.

The controller 340 may be programmed to ensure that the net level of ultrafiltrate or infused fluid meets a prescribed target which may be stored by the controller 340. The pumping speeds required to achieve balanced flow rates may be determined by the controller 340 using data stored by the controller such as look up tables or formulas. These data are generated using the synchronization procedures of the various embodiments and optionally by using pump curve data as well. The ratio of flow rate to pump speed may be presented by this stored data to indicate target pump speeds (or, equivalently, commanded flow rates) in a relationship between pressure difference as well as flow rate. For example, in any of the embodiments, a look up table may have cells with pump speeds where columns and rows correspond to the independent variables of pressure at the pump inlet (or pressure differential across the pump for non-peristaltic pumps) and flow rate.

At the same time treatment fluid 124 is pumped by fresh treatment fluid pump 128 at a predefined rate stored in the controller, which rate may be selected to correspond to the blood flow rate. The replacement fluid 120 may be controlled by the controller 340 which determines the rate of replacement fluid pump 116. The supplemental fluid 134 may be pumped at a rate regulated by the controller 340 by controlling the pumping rate of supplemental fluid pump 142. The supplemental fluid 132 may be pumped at a rate controlled by the controller 340 by controlling the rate of supplemental fluid pump 144. Any of the replacement fluid 120, supplemental fluid 134, or supplemental fluid 132 may or may not be included, along with the respective lines and pumps, in alternative embodiments. Flow control valves may be of any type as indicated above. As before, line 136 is present to indicate that in alternative embodiments, the supplemental fluids may enter the arterial blood line 139 upstream or downstream of the arterial blood pump 110.

Referring to FIG. 6B, in additional embodiments, a bridge line 147 that can be opened or closed selectively by the controller 340, connects the replacement fluid line 143 and the waste treatment fluid line 125. This may be controlled by means of a control valve 145. Another bridge line 117 that can be opened or closed selectively by the controller 340, connects the replacement fluid inlet line 149 and the waste treatment fluid line 125. This may be controlled by means of a control valve 115. Thus waste treatment fluid pump 154 and supplemental fluid pump 142 may be connected in series through treatment fluid branch loop closer 320. This allows the supplemental fluid pump 142 to be synchronized against the waste treatment fluid pump 154 by selected actuation of the control valves, e.g., 115, 145, 304, as will be evident from inspection. In alternative embodiments, any of the non-blood pumps may be synchronized with any other non-blood pump in the same manner using the same or similar devices.

Figure 7:
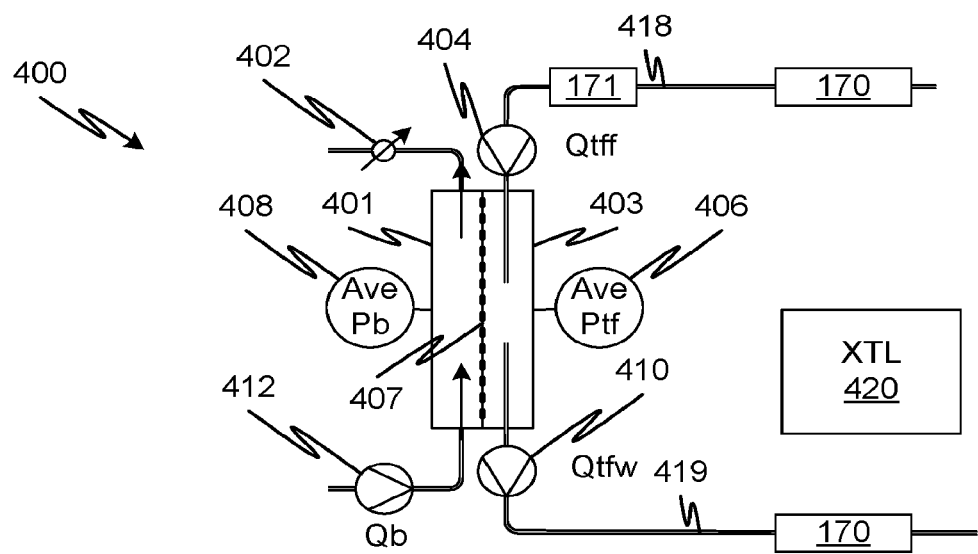
FIG. 7 is for describing certain principles of operation of the controller and blood treatment apparatus, according to embodiments of the disclosed subject matter.

Referring to FIG. 7, a blood treatment system 400 is illustrated schematically with some key elements of certain embodiments of the disclosed subject matter. A treatment device has a membrane 407 that divides blood 401 and non-blood 403 compartments. The blood compartment 401 may include the composite volume of the internal lumens of a microfiber bundle and the non-blood compartment 403 may be net space outside of such a microfiber bundle confined by a housing. A blood pump 412 pumps priming fluid or blood into the blood compartment 401 and a variable restrictor 402 restricts the flow of priming fluid to permit the pressure in the blood compartment 401 to be adjusted selectively by a controller 420. In treatment mode, the variable restrictor is not used. The controller 420 controls the speeds of pumps and detects the pressures of the blood 401 and non-blood 403 compartments by means of pressure sensors 406 and 408, which are shown schematically but may represent inlet and outlet pressure sensors for each compartment as in the foregoing embodiments. Net fluid transfer to/from the non-blood compartment is controlled by regulating the relative speeds of fresh 404 and waste 410 treatment fluid pumps. Flow meters 170 as described with reference to FIG. 5 may be provided on one or both of the fresh 418 and waste 419 treatment fluid lines. Since in the embodiment of FIG. 5, air is injected in the fluid traversing the flow meter 170, an air removal filter 171 may be provided in the fresh treatment fluid line 418 downstream of the flow meter 170. The flow meter 170 may be used as a confirmation of the synchronization procedure of the embodiments. If a controller 420 detects a disagreement between the flow rates when synchronization is established (e.g., S74, S108), then the controller 420 may generate a signal indicating the disagreement. The signal may be used to generate an alert or alarm condition.

Figure 8:
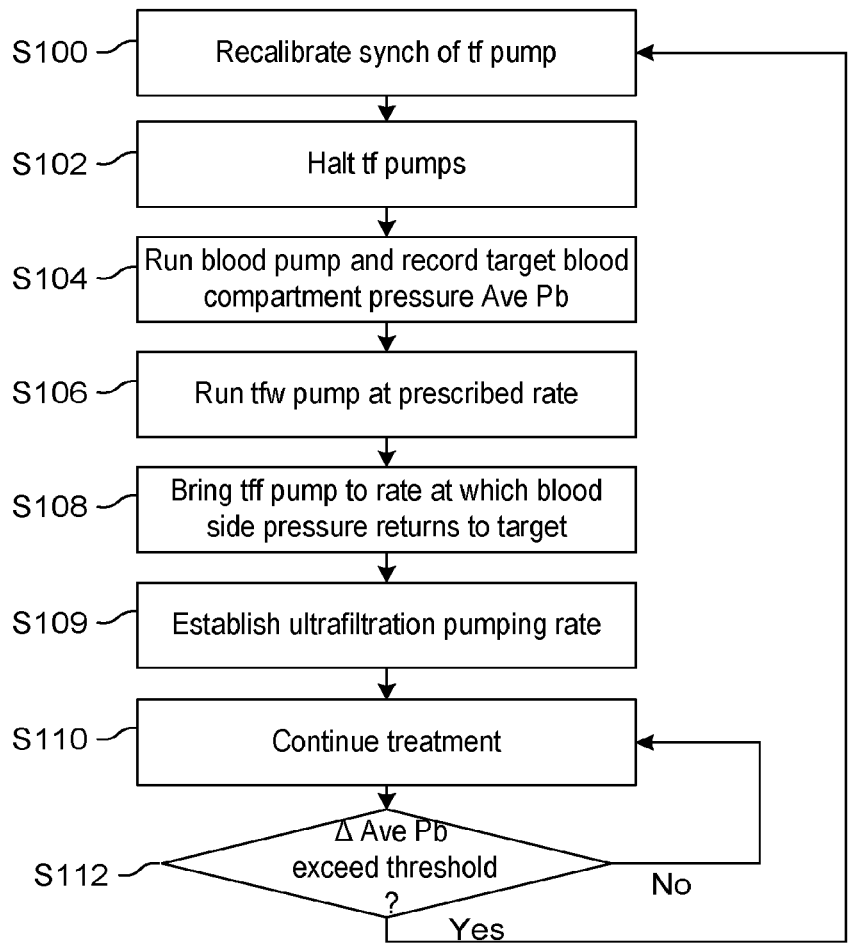
FIG. 8 shows a method for synchronizing fresh and waste treatment fluid pumps during a treatment, according to embodiments of the disclosed subject matter.

FIG. 8 shows a spot method for synchronizing fresh and waste treatment fluid pumps during a treatment, according to embodiments of the disclosed subject matter. In this method the treatment fluid pumps are synchronized for the then-current set of conditions in a treatment phase. This is similar to the procedures of FIGS. 4B and 4C except that instead of mapping a number of conditions of Ave Pb and Qtfw to estimate Qtff, a single Ave Pb (or as discussed above, a single Ave Ptf may apply) is measured, with no treatment fluid flow, from the current operating conditions and stored as a target and used with the current—prescribed—Qtf to determine a synchronous speed for the fresh treatment fluid pump. This is then offset to achieve ultrafiltration and refined by regulating the waste treatment fluid pump to achieve inlet pressure compensation. This has the benefit of determining the synchronous speed of the fresh treatment fluid pump for the precise conditions for treatment.

In the procedure of FIG. 8, a procedure for spot synchronization is now disclosed in further detail. instead of deriving a function to estimate fresh treatment fluid pumping rate from waste treatment fluid pumping rate and average blood compartment pressure, the fresh treatment fluid pumping rate is determined for a current, or predefined combination of waste treatment fluid flow rate and blood compartment average pressure. This can also be done as a complement to the derivation of an estimation function. For example, an operator may command the system to perform a single operating-point synchronization. At S100, during or before a treatment, a command is received or generated by the controller to resynchronize the treatment fluid pumps. At S102, the treatment fluid pumps are halted establishing a zero transmembrane pressure while the blood pump keeps running (or is started). At S104, with the blood pump running at a prescribed rate, the blood compartment average pressure Ave Pb (or Ave Ptf) is measured and stored as a target. Then the prescribed treatment fluid flow rate is established by commanding the waste treatment fluid pump at S106. The fresh treatment fluid pump is then controlled until the target blood compartment average pressure is restored at S108. At S109, the ultrafiltration is established by stepping the waste treatment fluid pumping rate up and iteratively compensating based on the measured inlet pressure to the waste treatment fluid pump. At S110, the treatment fluid pumping rates having been precisely established for the current blood flow rate, the treatment resumes at S110. At S112, if, during treatment, there is a change in average blood compartment pressure, the controller may command that the foregoing operation be repeated otherwise treatment continues at S110.

It will be observed that FIG. 8 illustrates a method for controlling flow in a fluid circuit. In the method, a controller regulates the flow of fluid across a blood treatment device membrane contacting a blood flow path responsively to a pressure signal indicating pressure in the blood treatment device. The regulating includes controlling speeds of inflow and outflow pumps, the inflow pump pumping treatment fluid into the blood treatment device and the outflow pump pumping treatment fluid out of the blood treatment device responsively to a target pressure indicating a blood and/or treatment fluid side of the membrane. At a synchronization time prior to the regulating, the target pressure is obtained and stored in a data store of the controller. The target pressure is calculated from a detected pressure on the blood and/or treatment fluid side of the membrane at a time when the inflow and outflow pumps are halted. The controller, at the synchronization time, halts the inflow and outflow pumps.

The regulating operation may be followed by, or include, advancing the downstream synchronized pump speed to provide a prescribed or calculated ultrafiltration rate such that a target net ultrafiltered volume is removed from a patient by the end of the treatment. The advancing may be accomplished simply by increasing the flow rate of the downstream pump by an amount equal to the targeted ultrafiltration rate. So if the commanded flow rate of the effluent pump is 100 ml/min and the ultrafiltration rate is 5 ml/min, then the advanced effluent pump rate will be changed from the value 100 ml/min, at which the synchronization was performed, to 105 ml/min.

The target pressure may be obtained from the blood side of the treatment device or from the treatment fluid side of the treatment device, respectively, by averaging inlet and outlet pressures on the respective side. Alternatively, the pressure may be obtained from the treatment fluid (non-blood) side outlet only. The foregoing method embodiment may be performed during priming and repeated during treatment.

In any embodiments, the pressure sensor may be located on the downstream non-blood side of the treatment device and the pressure sensor may be used alone for synchronization. Alternatively, pressure sensors on non-blood inlet and outlet may be averaged for purposes of synchronization. In yet additional embodiments, a pressure sensor may form part of the blood treatment device and indicate a temperature at a middle point, the inlet, or the outlet of the non-blood compartment of the blood treatment device. In any embodiments, the pressure sensor may be located on the downstream blood side of the treatment device and the pressure sensor may be used alone for synchronization. Alternatively, pressure sensors on blood inlet and outlet may be averaged for purposes of synchronization. In yet additional embodiments, a pressure sensor may form part of the blood treatment device and indicate a temperature at a middle point, the inlet, or the outlet of the blood compartment of the blood treatment device.

Figure 9:
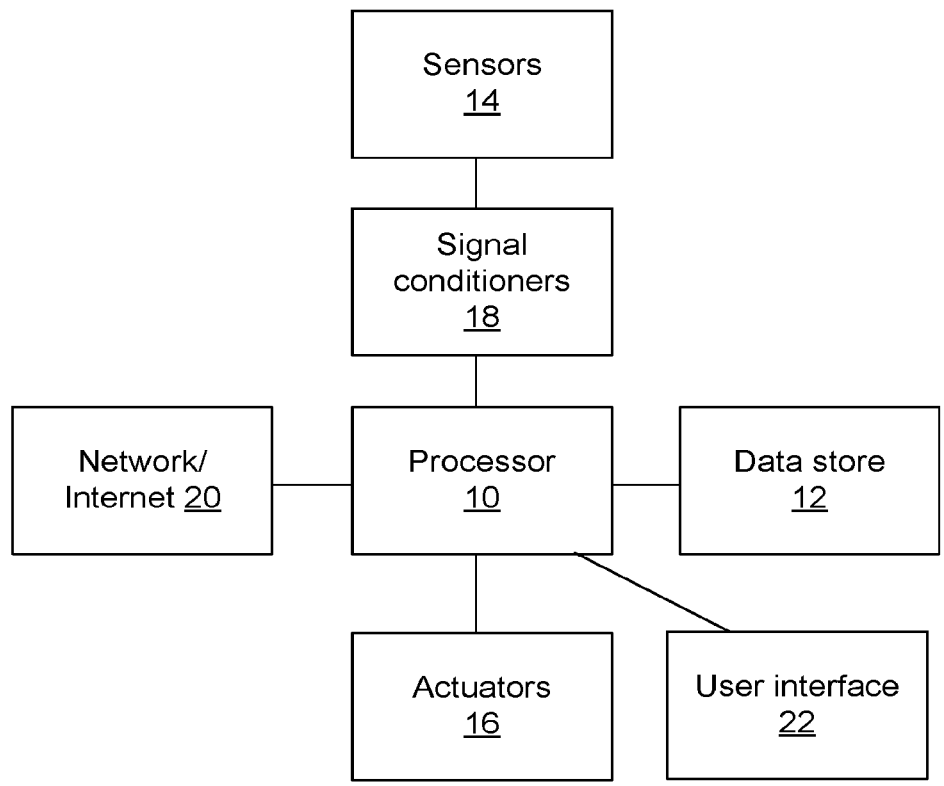
FIG. 9 shows a programmable control system with details that may be inherent in any of the controller embodiments disclosed herein and according to various embodiments of the disclosed subject matter.

FIG. 9 shows a programmable control system with details that may be inherent in any of the controller embodiments disclosed herein. A processor 10 receives signals from sensors 14, optionally by way of one or more signal conditioners represented collectively at 18. Examples of signal conditioners will be evident from the embodiments, but may include analog filters to more complex devices such as machine learning processors that classify diffuse signal combinations. The processor may store and receive data to and from a data store 12 or a network/Internet 20. Actuators 16 represent the various actuators described herein. The processor may connected for interaction with users via one or more user interface 22 elements such as buttons, screens, keyboard, pointing devices, alarm annunciators, speakers, lights, etc.

Figure 10A:
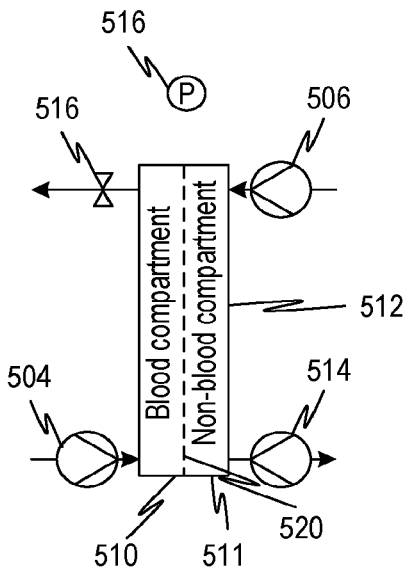
FIGS. 10A and 10B illustrate the generalization of the flow balancing scheme in which blood side or non-blood side inflow and outflow pumps may be used to regulate the fluid balance according to embodiments of the disclosed subject matter.
Figure 10B:
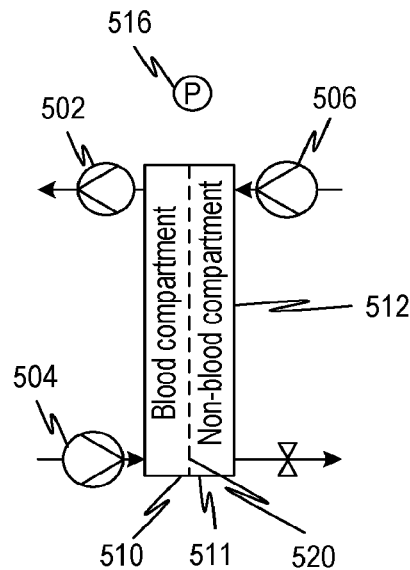

FIGS. 10A and 10B show a figurative representation of a blood treatment device 512 with blood compartment 510 and non-blood compartment 511 separated by a membrane 520. In FIG. 10A, the fluid balance of a patient is controlled by a controller (not shown) by regulating the relative speeds of treatment fluid pumps 506 and 514. In FIG. 10B, the fluid balance of a patient is controlled by a controller (not shown) by regulating the relative speeds of blood pumps 502 and 504. The synchronization procedure of FIG. 8 may be used to obtain a speed of the treatment fluid pump 506 that is synchronized to the speed of the pump 514 by determining a target pressure of the non-blood compartment 511 at which there is no flow through the membrane and synchronizing finding the speed of the pump 506 that achieves that target pressure for the desired pumping rate of the pump 514. However, a similar procedure can also be used when blood flow is balanced instead of treatment fluid as in the embodiment of FIG. 10B by determining the speed of the blood pump 504 that is synchronized with the blood pump 502 based on a target pressure obtained by establishing the no-transmembrane flow condition during priming. The target pressure may be obtained by halting flow of priming fluid or blood by halting both blood pumps 502 and 504. Then, the pressure while there is treatment fluid flowing through the non-blood compartment may be measured. The pressure may be any of the disclosed embodiments including the average of the blood inlet and outlet pressures. Then the blood pump 502 can set to a predetermined flow rate and the pump 504 operated to determine a synchronized speed of the blood pump 504 for a selected speed of the blood pump 502. Note that 516 indicates one or more pressures sensors which may be any of those listed as alternatives including average of inlet and outlet pressure.

Figure 11:
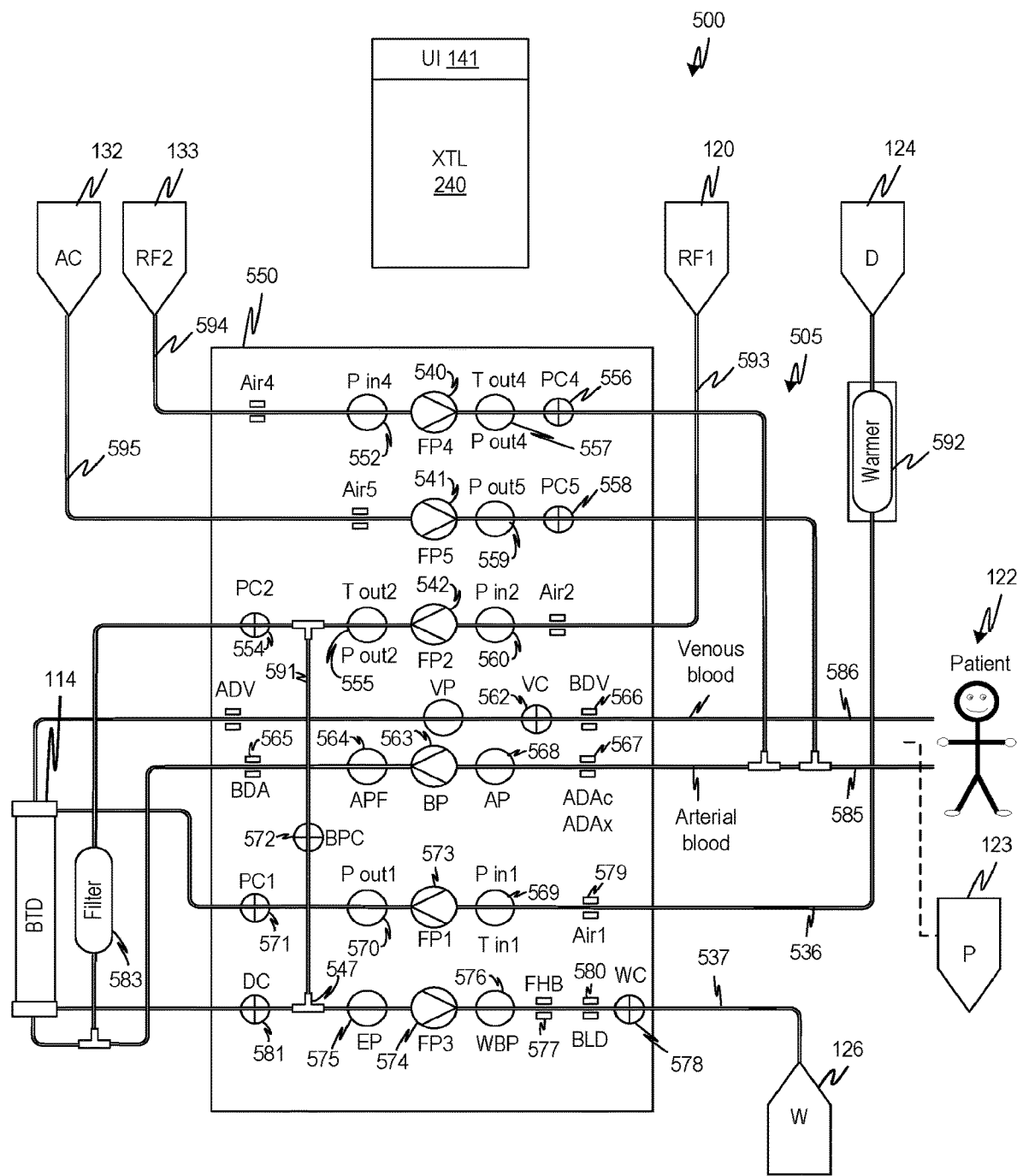
FIG. 11 shows a blood treatment machine figuratively with various actuators and sensors and an attached fluid circuit according to embodiments of the disclosed subject matter.

Referring to FIG. 11, a multiple fluid blood treatment system 500 includes a fluid circuit 505 and a machine 550. The system 500 is capable of hemofiltration, hemodialysis, and hemodiafiltration. The machine 550 regulates the flow of treatment fluid to generate a cumulative target ratio of fluid drawn or infused into a patient 122 over the course of a treatment. The blood treatment system 500 regulates the flow of fluid in a fluid circuit 505 that includes an arterial blood line 585, a venous blood line 586, a fresh treatment fluid line 536 and a waste treatment fluid line 537. The net flow of fluid into or out of a patient or priming source/sink, at any given time, is determined by a current difference between the volume of treatment fluid pumped from a treatment device 114 to the combined volume pumped into the treatment device 114 and pumped into the arterial blood line 585, a venous blood line 586. Fluid (blood or priming fluid) is pumped from a source (e.g., patient 122 or priming fluid source/sink 123) into the treatment device 114 by a blood pump 563 and flows from the treatment device 114 back to the patient 122 or priming fluid source/sink 123, which may be a drain, collection container, or recirculating container. The illustrated configuration may include typical incidents of dialysis machines such as detachable fluid circuits, peristaltic pumps, sensors, etc. In this case, flow balance to achieve the desired ultrafiltration is provided by regulating the rates of fluid pumps including two treatment fluid pumps: a fresh treatment fluid pump (also referred to as a dialysate pump) 573, which pumps fresh treatment fluid 124 into the treatment device 114, a waste treatment fluid pump (also referred to as an effluent pump) 574, which pumps waste (spent) treatment fluid from the treatment device 114 to a drain 126, a supplemental fluid pump 541, which pumps a supplement, such as an anticoagulant, from a supplemental fluid source 132 into the arterial blood line 585, and replacement fluid pumps 540 and 542, which pump a first replacement fluid 120 and a second replacement fluid 133, respectively, into the arterial blood line 585 at the locations therealong indicated in the drawing. Note that other fluids can be added or substituted according to the requirements of different treatment modalities and the illustrated examples are not intended to be limiting.

As above, control and sensing are provided by a controller 240 which may be of any form and again, typically, a programmable digital controller such as an embedded computer. Treatment fluid is pumped from a treatment fluid source 124, such as a bag or fluid proportioning system, by a fresh treatment fluid pump 573. The treatment fluid passes through a warmer 592, an air detector 579, through or past temperature and pressure measurement devices P in1, T in1 569, through or past pressure measurement devices P out1 570 and into the treatment device 114. Before entering the treatment device 114 the fresh treatment fluid line 536 passes a clamp PC1 571 (though a fluid control valve may also be used) that is controlled by the controller 240. The treatment fluid flows through the treatment device 114 pumped by an effluent pump (FP3) 574. The treatment fluid flowing from the treatment device 114 and passes to a drain (or collection chamber) 126. The waste line 537 from the treatment device 114 engages with a clamp DC that is controlled by the controller 240. The waste line 537 also passes an effluent pressure sensor EP 575 upstream of the effluent pump (FP3) 574. The waste line 537 also passes a waste pressure sensor WBP 576 downstream of the effluent pump (FP3) 574. The waste line 537 also passes a blood detector 580 and a free hemoglobin sensor 577. Flow in the waste line 537 is controlled by a clamp DC 581 (though a fluid control valve may also be used) between a junction 547 and the treatment device 114 and a waste clamp WC 578 between the waste outlet and the effluent pump (FP3) 574.

A replacement fluid RF1 120 may be pumped into the arterial blood line 585 (or alternatively or in addition into the venous blood line venous blood line 586) through a replacement fluid line 593. In alternative embodiments, the dilution by a replacement fluid may occur at a midpoint of the treatment device 114 as discussed above. The replacement fluid RF1 120 is pumped by a pump 542 through a line 593 which passes through an air sensor Air2, an upstream pressure sensor P in2 560, a downstream pressure sensor P out2 and temperature sensor T out2 555, and a pinch clamp PC2 554. The replacement fluid passes through a sterile filter 583 before it flows into the arterial blood line 585.

A replacement fluid RF2 133 may be pumped into the arterial blood line 585 (or alternatively or in addition into the venous blood line venous blood line 586) through a replacement fluid line 594. In alternative embodiments, the dilution by the replacement fluid may occur at a midpoint of the treatment device 114 as discussed above. The replacement fluid RF2 133 is pumped by a pump 540 through line 594 which passes through an air sensor Air4, an upstream pressure sensor P in4 552, a downstream pressure sensor P out4 and temperature sensor T out4 557, and a pinch clamp PC4 556.

A supplemental fluid (such as an anticoagulant) 132 may be pumped into the arterial blood line 585 (or alternatively or in addition into the venous blood line venous blood line 586) through an anticoagulant line 595. The supplemental fluid 132 is pumped by a pump 541 through line 595 which passes through an air sensor Air5, a pressure sensor P out5 559 and a pinch clamp PC5 558.

Blood is pumped by a blood pump BP 563 through air sensors ADAc and ADAx 567 which are a sensitive air bubble detectors connected to independent alarm systems for safety. The arterial blood also passes an inlet pressure sensor AP 568 and an outlet pressure sensor APF 564 multiple contaminant detector (air or non-blood fluid) BDA 565. Venous blood returns from the treatment device 114 via venous blood line 586. A venous line clamp 562 blocks returning blood if a safety hazard is detected, such as air in the blood lines. A an air detector BDV 566 is a sensitive air detector for indicating the presence of bubbles in the venous line.

A bypass line 591 is used for synchronizing the flow of replacement fluid pump FP2 542 with the effluent pump FP3 574. The bypass line 591 is opened and closed by means of a clamp BPC 572 (though a fluid control valve may also be used). The bypass line 591 connects the replacement fluid RF1 line 593 with the waste line 537.

The treatment device 114 may be adapted for any type of blood treatment including, but not limited to, dialysis, hemofiltration, hemodiafiltration, apheresis, adsorption, and hemoperfusion. Further the fluids 132, 133, 120, 124 may be any type of fluid and the types described are examples not intended to limit the disclosed subject matter. Examples of fluids are medicaments, drugs, and anticoagulant (e.g., citrate, heparin).

The controller 240 is also connected to control each of the blood pump 563, replacement fluid pump 542, replacement fluid pump 540, the supplemental fluid pump 541, the fresh treatment fluid pump 573, and the waste treatment fluid pump 574. In embodiments, each pump contributing to flow balance may have a pressure sensor upstream of it to ensure that pressure compensated control of its speed can be provided. This is the case in the illustrated example. In embodiments, pressure sensors are used for pressure-compensated speed control. They may be positioned such that they provide a reliable and consistent indication of pressure upstream of the respective pump or pumps.

In a treatment operation of blood treatment system 500, the pumps pump fluids in the directions indicated by the arrowheads of each pump symbol. The controller regulates the speeds to effect a flow balance of fluid to/from the patient that meets a target ultrafiltration required over the course of the treatment. The system can also control the rate of ultrafiltration within a target range as well. the flow of treatment fluid in the fresh treatment fluid line 127 against the flow of blood in the venous blood line waste treatment fluid line 125 such that a net take-off of fluid (ultrafiltration) or a net infusion of fluid takes place as calculated by the controller 240 or per a command received by the controller 240. The instantaneous rate of ultrafiltration or infusion may vary during the course of a treatment. The controller 240 may be programmed to ensure that the net level of ultrafiltrate or infused fluid meets a prescribed target which may be stored by the controller 240. The pumping speeds required to achieve commanded flow rates may be determined by the controller 240 using data stored by the controller such as look up tables or formulas. The ratio of flow rate to pump speed (equivalently, the commanded flow rate) may be presented by this stored data to indicate target pump speeds in a relationship between pressure difference across the pump as well as flow rate; the pump curves. For example, in any of the embodiments, a look up table may have cells with pump speeds where columns and rows correspond to the independent variables of pressure at the pump inlet (or pressure differential across the pump for non-peristaltic pumps) and flow rate. Operating points may be interpolated or extrapolated for operating conditions that lie between or outside those corresponding to the cells or the formula or look-up table may provide interpolated or extrapolated values.

Figure 12A:
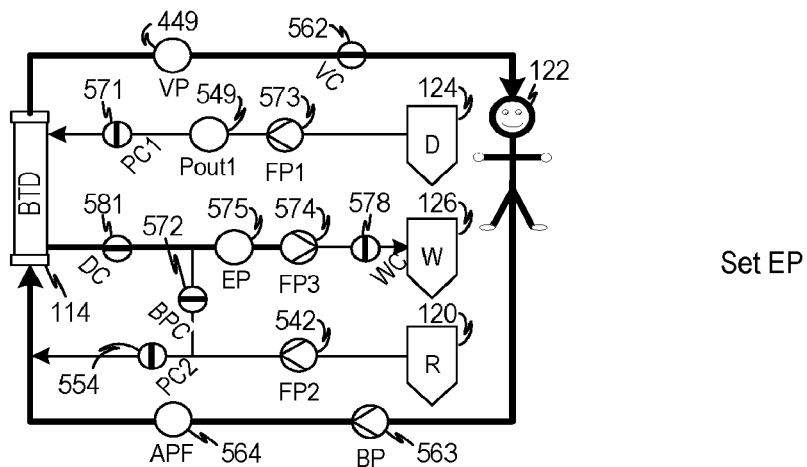
FIG. 12A-12C show elements of a hemofiltration system or a hemodiafiltration system, the elements being common to, but not limited to, the multiple stream system of FIG. 11, for purposes of describing a synchronization procedure for balancing flow for a hemofiltration treatment according to various embodiments of the disclosed subject matter.

A procedure in which the embodiment of FIG. 11 is used for performing hemofiltration is now described. In FIGS. 12A-12G, the thicker lines indicate lines where a flow is established and the thin lines indicate no-flow. Also, closed clamps are indicated by circles with a line perpendicular the controlled line when closed parallel to it when opened. Referring now to FIG. 12A, a simplified version of the drawing of FIG. 11 is shown in an operating mode in which blood is pumped, at a desired blood flow rate, through the treatment device 114 by the blood pump 563. The other pumps are halted. The clamp DC 581 is open and other clamps 571, 572, and 554. Clamp WC 578 may have no effect because the effluent pump 574 is halted preventing any flow through the waste line. Since there is a flow passage between the non-blood compartment of the treatment device 114 and the effluent pressure sensor EP 575, and since there is no flow in the non-blood compartment of the treatment device 114 and no flow through the membrane to the blood compartment owing to the fact that the clamps 571, 572, and 554 are closed and effluent pump 574 is halted, the effluent pressure sensor EP 575 indicates the pressure of the non-blood compartment of the treatment device 114 which also reflects the average pressure in the blood compartment. The effluent pressure is recorded as a target (EP-target) by the controller in the operating mode shown in FIG. 12A and then the controller implements the configuration of FIG. 12B.

Figure 12B:
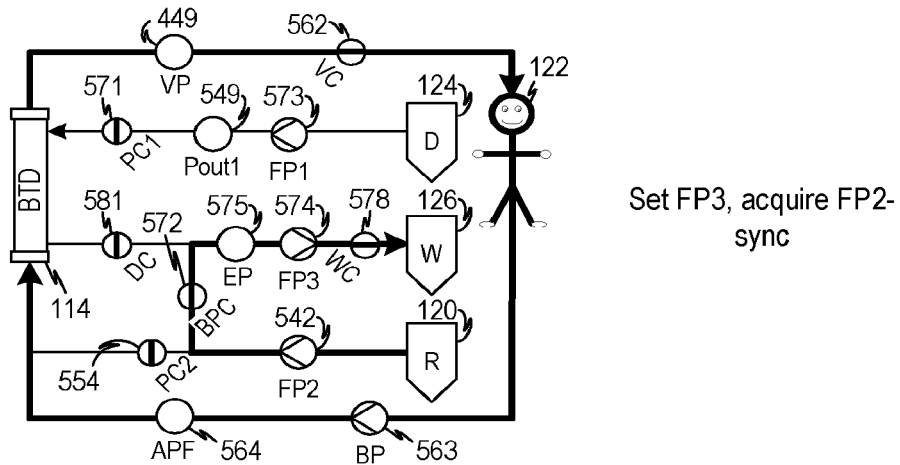

In FIG. 12B, the bypass branch clamp 572 and the waste clamp 578 are opened and the clamp 581 is closed. This connects the replacement fluid pump 542 and the and effluent pump 574 in series. The effluent pump 574 and the replacement fluid pump 542 are commanded to run at a predefined replacement fluid pump rate according to a hemofiltration prescription. That is, the rate of both pumps is set to the rate at which replacement fluid is planned to be infused into the patient blood line. The replacement fluid pump 542 is then adjusted while monitoring the effluent pressure from effluent pressure sensor EP 575 so that the pressure indicated by the pressure sensor EP 575 is equal to the target (EP-target). The commanded rate of the replacement fluid pump 542 that provides this target pressure is recorded as a target (Q-sync) commanded flow rate of the replacement fluid pump 542. Next the controller configures the system as shown in FIG. 12C.

Figure 12C:
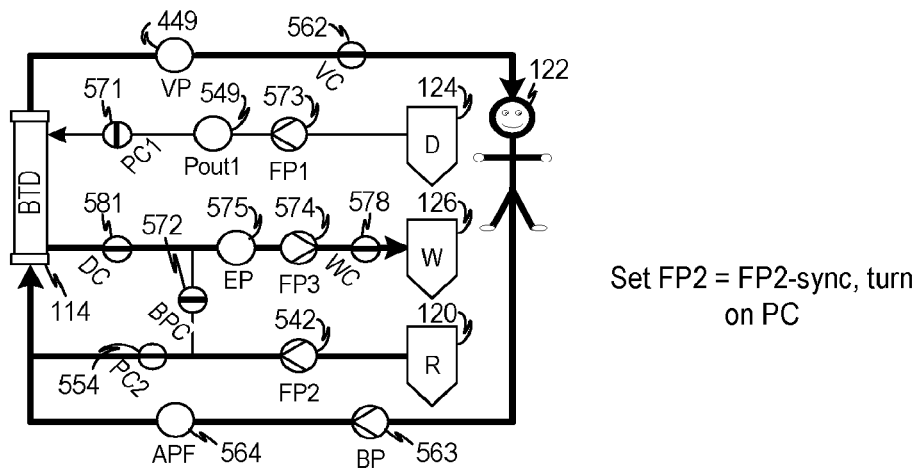

Referring to FIG. 12C, in a hemofiltration treatment, the replacement fluid pump 542 is set to the target Q-sync. The effluent pump is operated at the predefined replacement pump speed used for synchronizing in the procedures discussed with regard to FIG. 12B. Immediately thereafter, the pressure compensation is used to maintain the speed of the effluent pump. As a result, if the pressure indicated by the pressure sensor EP 575 falls, the speed of the effluent pump 574 is increased and vice versa.

Note that the configuration of FIGS. 12A-12C was identified as a simplified view of the system of FIG. 11. However, it should be clear that the configuration of FIGS. 12A-12C is consistent with other embodiments that include other elements or a bare minimum or equivalent of those shown in alternative embodiments.

Figure 12D:
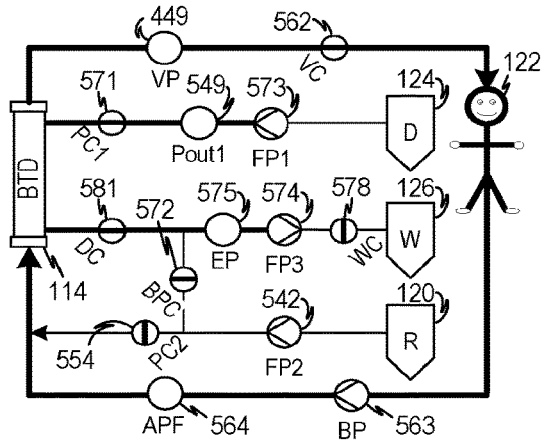
FIG. 12D-12G show elements of a hemodiafiltration system, the elements being common to, but not limited to, the multiple stream system of FIG. 11, for purposes of describing a synchronization procedure for balancing flow for a hemodiafiltration treatment according to various embodiments of the disclosed subject matter.

A procedure in which the embodiment of FIG. 11 is used for performing hemodiafiltration is now described. Referring to FIG. 12D, the same procedure as discussed above for obtaining record the effluent pressure as a target (EP-target) is performed except that both EP and an average of Pout1 549 and WP (the latter average equal to an average pressure of the non-blood compartment, HD avg) are recorded as respective target pressures. The same configuration is established by the controller as in FIG. 12A except that the clamp 571 (PC1) is opened to permit the sensor Pout1 549 to detect the non-blood compartment pressure. Next, after the EP-target is recorded, the controller implements the configuration of FIG. 12E.

Figure 12E:
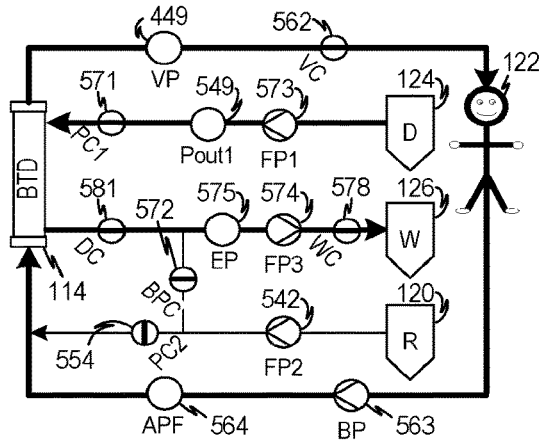

In FIG. 12E, the dialysate clamp 571 is opened and the dialysate pump 573 and the effluent pump 574 are commanded to a speed equal to a prescribed dialysate flow rate for the treatment to be performed. The dialysate pump 573 is commanded by the controller to vary its speed while sampling the effluent pressure 575 to determine the commanded flow rate of the dialysate pump 573 that coincides with a measured HD-avg equal to the HD-avg-target as indicated by the effluent pressure EP sensor 575 and the Pout1 549 pressure sensor. As should be clear from the present disclosure, the commanded flow rate may be generated from a dynamic model such as a curve fit of the pressure data or it may be obtained from the pump rate after the synchronization feedback (PID) control has reached equilibrium or synchronous flow lock of the dialysate pump 573 and the effluent pump 574. In embodiments, the dialysate pump 573 is feedback-controlled based on the error, (effluent pressure HD-Avg)—(HD-Avg-target) so that the dialysate pump 573 runs at a speed that maintains the effluent pressure indicated by the measured HD-avg. This establishes a command speed of dialysate pump 573 Q-Dialysate-sync that is flow-synchronized with the command speed of the effluent pump 574. The command speed of the dialysate pump is recorded.

Figure 12F:
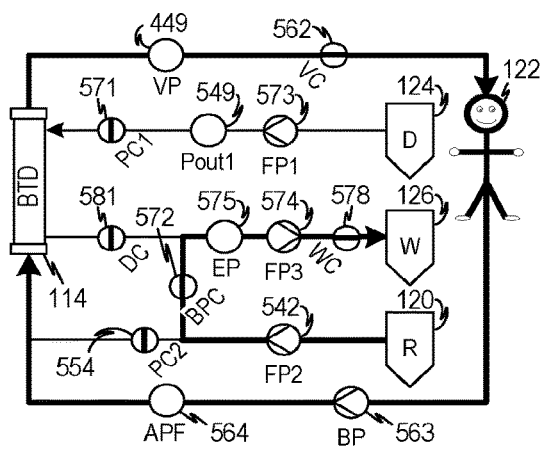

In FIG. 12F, the bypass branch clamp 572 is opened and the clamp 581 is closed. The dialysate pump 573 is halted and PC1 clamp 571 closed. The illustrated configuration connects the replacement fluid pump 542 and the effluent pump 574 in series as in FIG. 12B. The same procedure is performed as described with reference to FIG. 12B to obtain the commanded rate of the replacement fluid pump 542 that provides the target pressure. This commanded rate at synchronization is recorded as a target (RF-Q-sync). This is a commanded flow rate of the replacement fluid pump 542 that will be used during treatment. Next the controller configures the system as shown in FIG. 12G.

Figure 12G:
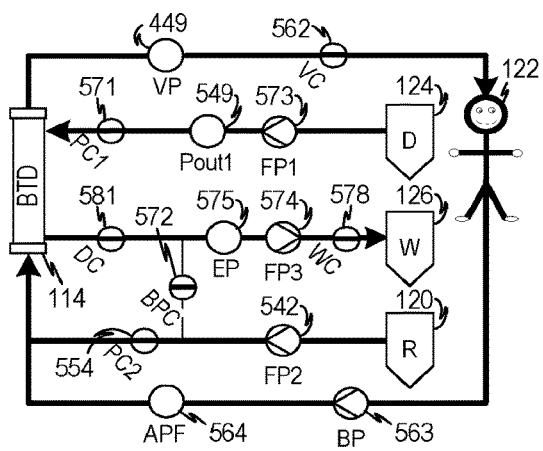

Referring to FIG. 12G, the dialysate line clamp 571 is next opened and the dialysate pump operated at the speed Q-dialysate-sync. The effluent pump 574 is commanded to a rate equal to the commanded dialysate flow rate used during synchronization procedure of FIG. 12F plus the hemofiltration rate. Then the replacement fluid pump 542 is commanded to run at RF-Q-sync. The controller then implements pressure compensation of the effluent pump 574. The controller may also implement pressure compensation control of all the pumps as inlet pressure conditions (and/or other conditions) depart from the conditions at the time of synchronization. In this mode, hemodiafiltration treatment is performed.

Note that in a variation of the embodiments of FIGS. 12D-12F, the replacement fluid is not used and only the synchronization operation of FIG. 12E takes place. In that case, the flow of replacement fluid in the operation of FIG. 12G is zero.

Note that to establish the effluent pump 574 speed, the controller may simply calculate the shaft speed of a peristaltic pump equal to the sum of the shaft speeds corresponding to the command speeds used to establish the dialysate and replacement fluid flow rates at the time of the respective synchronizations. Note that in all of the embodiments, the effluent pump may be increased above the synchronized rate to provide a prescribed ultrafiltration rate as described herein and particularly as described with reference to FIGS. 13A to 13C.

Note in a further variation of FIG. 12E, instead of synchronizing by tracking a pressure of the effluent pressure sensor 575.

Note that in this or any of the embodiments, including those defined by the claims, the ratio of commanded pump speed to estimated flow may be given by a pump curve that is based on inlet pressure, outlet-inlet pressure difference, or a combination thereof, depending on suitability for the type of pump used. Other factors may also be used for pump flow compensation such as temperature and duration of use.

Figure 13A:
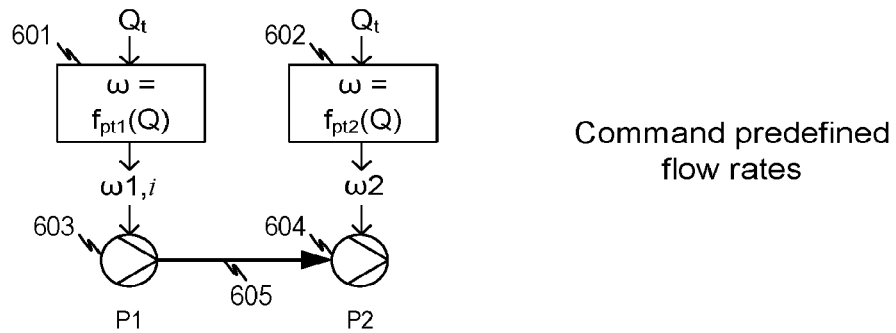
FIGS. 13A-13C show the abstract elements and processes for pump balancing according to various embodiments of the disclosed subject matter.
Figure 13B:
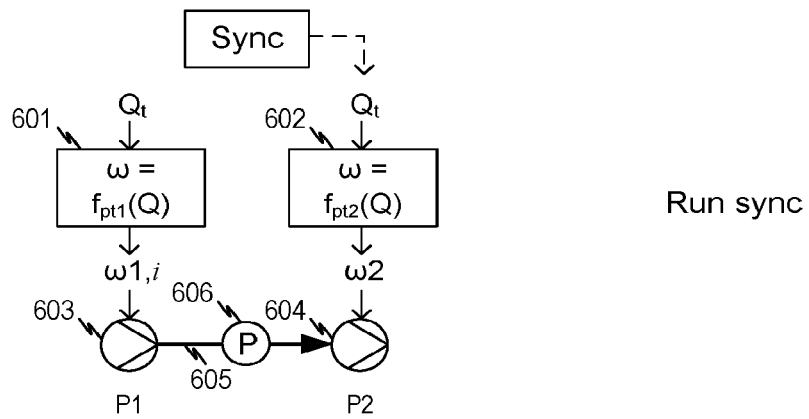

Referring to FIGS. 13A-13B, a summary of how synchronization is combined with pump inlet pressure compensation is described. Referring now to FIG. 13A Illustrated are two pumps 603 and 604 connected in series by a flow channel 605. The flow channel 605 may be a constant volume channel such as a bypass connection or a blood treatment device where one of the compartments is sealed or it may be a "leaky" membrane channel such as in a blood treatment device where a pressure that establishes zero transmembrane pressure condition will be established during synchronization. First, a controller generates a desired flow rate $Q_t$ and converts that using a standard conversion 601 (e.g., formula, lookup table) to a rotational frequency for each pump ($\omega 1,i$ and $\omega 2$, respectively) where the first pump rotational frequency is an initial speed for the desired flow rate $Q_t$ which is updated during synchronization. Note that Qt and $\omega 1,i$ and $\omega 2$ are ultimately commanded speeds and a controller may bypass the conversion 601 and simply command pump speed directly but typically inputs originate as desired flow rates so the conversion between a physician's prescription in fluid volume flow rate units would generally be converted into the same units in an application level control scheme until ultimately converted to a rotational frequency (otherwise identified herein as pump speed). This is all merely to note that it will be understood in the discussion that discussion of a commanded pump flow rate or pump speed relate to the same thing. However it is recognized that the conversion 601 and 602 is not exact which is why a synchronization is performed. The conversions 601 and 602 may depend on the type of pump so different functions $f_{pt1}$ and $f_{pt2}$ are shown but it should be understood that the pumps could be of the same type in which case the functions would then be the same.

Referring now to FIG. 13B, once flow is initially established between the pumps 603 and 604, a synchronization procedure is performed according to any of the embodiments described above. As the synchronization procedure progresses, the commanded flow rate (or equivalently, the pump speed or rotational frequency) of the pump 603 is varied until sufficient data are obtained to estimate the commanded flow rate that matches the actual flow rate of the pump 604. As will be understood from the disclosure herein, the data the error variable and the commanded pump speed of pump P correlated with the error variable where the error variable may be weight, volume (e.g., FIGS. 6A, 6B) or pressure (e.g., FIGS. 1A-1C including the treatment fluid-balancing alternative), pressure (e.g., FIGS. 3A-3E), or pressure drop (e.g., FIG. 5). The commanded rate of the pump 603 is adjusted by a controller to find a synchronized speed which is then recorded along with the inlet pressure of the pump 604 that corresponds to it. Note that the pressure 606 at the inlet of the second pump 604 may be known in advance if the zero-transmembrane flow condition is provided through pressure management as in the example of FIGS. 3A-3E. Once the synchronized speed of the first pump 603 is established the pump 604 can be operated thereafter at the commanded rate Qt and the upstream pump 603 at the synchronized speed to achieve a flow balance as long as conditions remain the same, for example, the pressure upstream of the pump 604 remains the same.

Figure 13C:
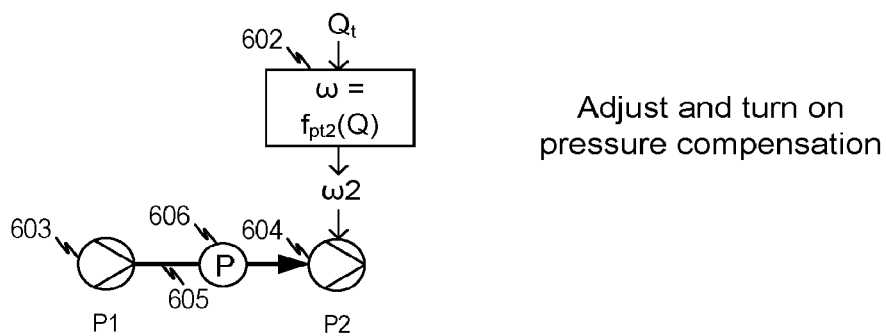

Referring to FIG. 13C, after the synchronized speed of the pump 603 is established, the speed of pump 604 may thereafter be varied in response to the inlet pressure 606 which has been identified above as "pressure compensation." Pressure compensation specifies a change of volume flow rate to the change inlet pressure of the pump 604. This ratio may vary over different pump speeds so multiple compensation curves may be provided and used. Generally the compensation ratio or ratios are obtained by doing experiments with a specific pump and tubing configuration where peristaltic pumps are used.

Pressure compensation-based speed adjustment may be performed continuously or at predefined intervals during a treatment, for example. As noted above, the pressure 606 may change is if the treatment calls for the pump 604 to be operated at a higher flow rate than pump 603 in order to achieve a net flow out of the channel 605 (e.g., when the channel 605 is a treatment device that can draw fluid from a patient's blood through a membrane thereof), i.e., there is a net ultrafiltration. The speed of pump 604 can be lowered relative to the synchronized speed of pump 603 if a negative ultrafiltration rate is indicated by the controller or user.

To implement such predefined difference in the flows of the pumps, the speed of pump 604 may be adjusted proportionately to the higher volume rate sought. For example, if the target flow rate Qt is 200 ml./min and the ultrafiltration rate desired is 5 ml./min, then the pump 604 speed can be commanded to 2.5% higher than Qt. The higher speed of the pump 604 will result in a drop in pressure 606 which will produce a slightly lower rate of flow than the rate sought (2.5% higher than Qt). So the pump 604 speed must then be adjusted so that the rate of flow of pump 604 according to the compensation ratio matches the incrementally higher rate sought. This may need to be done iteratively until the flow rate of the pump 604 converges to the estimated target value. This may be done using feedback control based on an optimization algorithm that minimizes the error between the calculated Qt by varying the pump 604 rate. Alternatively, a function relating the rate of pressure drop to the flow difference (the flow difference being equal to the ultrafiltration rate) may allow for the adjusted flow rate of the pump 604 to be predicted in a feedforward fashion.

The compensation ratio relates actual flow rate with a reference flow rate (in the example, Qt) by the following formula.

$$Qact(t)=(1+\alpha*(Pinlet(t)-Pref))*Q(t)$$

where Qact(t) is the actual flow rate through the compensated pump, a is a pump efficiency correction factor (i.e., the pump pressure compensation coefficient), Pinlet(t) is the inlet pressure, and Pref is the pressure where the pump was calibrated or synchronized (the reference point where the pump efficiency was measured). The pump pressure compensation coefficient $\alpha$ is dependent on the characteristics of the pump and the pump tubing segment. In embodiments, the inlet pressure correction may be 1.8%/25 mmHg deviation from the previous sync pressure. This value was obtained for a particular pump type and a particular type of pumping tube segment after certain predefined operating conditions which include a break-in operating period and using a certain fluid type. Thus the value is by no means limiting.

It should be clear from the foregoing how the correct value of a pump pressure compensation correction formula or lookup table may be obtained for other operating conditions. Note also that the above formula is a particular relationship that can be expressed analytically quite simply. However, other types of pumps may have performance characteristics that depend on additional variables and on inlet pressure in other ways that make a different compensation function or lookup table desirable. For example, the flow may depend on other measurable variables such as interval of time that the pumping tube segment has been in use (e.g., number of roller strikes or shaft rotations of a peristaltic pump actuator) and fluid temperature in addition to inlet pressure. Pump outlet pressure may also be included as a factor. In general correction may be handled by means of an offset proportional correction as in $$Qact=[(1+\alpha_{Pin}(Pin-Pref))(1+\alpha_{life}(t))(1+\alpha_{temp}(T-Tref))]Qref$$

where Qact is the compensated flow rate, Qref is the commanded flow rate as synchronized. Pref and Tref are the reference conditions of pressure and temperature and t is the amount of time or number of pump cycles for pump tube segment usage. Pin and Tare the current measure inlet pressure and fluid temperature, respectively.

It should be clear from the above, that the compensated flow rate may still contain a systematic error relative to the actual flow rate and that compensation merely adjusts for a departure from synchronized flow rates. Effectively this provides ratiometric proportioning with ratios (compensation factors) governing the offsets required to achieve a desired ultrafiltration from a patient.

During synchronization, the pressure of the channel between the pumps undergoing synchronization may be unsteady and gradually, based on feedback control using a PID control function implemented by a controller, progress toward a synchronized state. There may be several parameters for example, two time intervals defined for purposes of controlling the synchronization procedure. A first time interval is defined between the start of the synchronization procedure, when the two pumps are commanded to an initial speed, and the point at which the feedback signal rate of change falls below a threshold. The latter may be obtained by a moving average of the signal. The moving average may be defined by an averaging window of a predefined shape and time width. The second time interval may be an averaging period over which, after the moving average has fallen below the threshold, the pressure signal is averaged. There is value in minimizing the lengths of these time intervals. There may also be defined a threshold standard deviation for high frequency variations in the error signal that indicate "bad" synchronization. Together these criteria may establish when the synchronization is completed and whether the data obtained from the synchronization is valid.

Positive displacement pumps such as peristaltic pumps generate pressure pulses at their inlet and at their outlets. This causes the error signal used to synchronize pumps to be pulsatile. It has been discovered that combinations of certain speeds of the first and second pumps arranged for synchronization, particularly at low flow rates, generate pressure variations that fail to converge in a short period of time producing "bad" or incomplete synchronizations according to reasonable time periods for the intervals discussed above. These undesirable speed combinations can be discovered in the laboratory and used by the controller to allow the identification of allowed and non-allowed conditions of the pumps undergoing synchronization. To avoid non-allowed conditions while still providing a full range of flow rate combinations, the controller can use flow restrictions to generate artificially low inlet pressures to one pump or the other in order to alter the pulse frequency of that pump for a given flow rate. Thus, the controller may contain a matrix correlating the first pump flow rate and the second flow rate and for each, establish allowed ranges of inlet pressures for the first pump that avoid the speed combinations that produce slow or bad synchronizations.

Figure 14A:
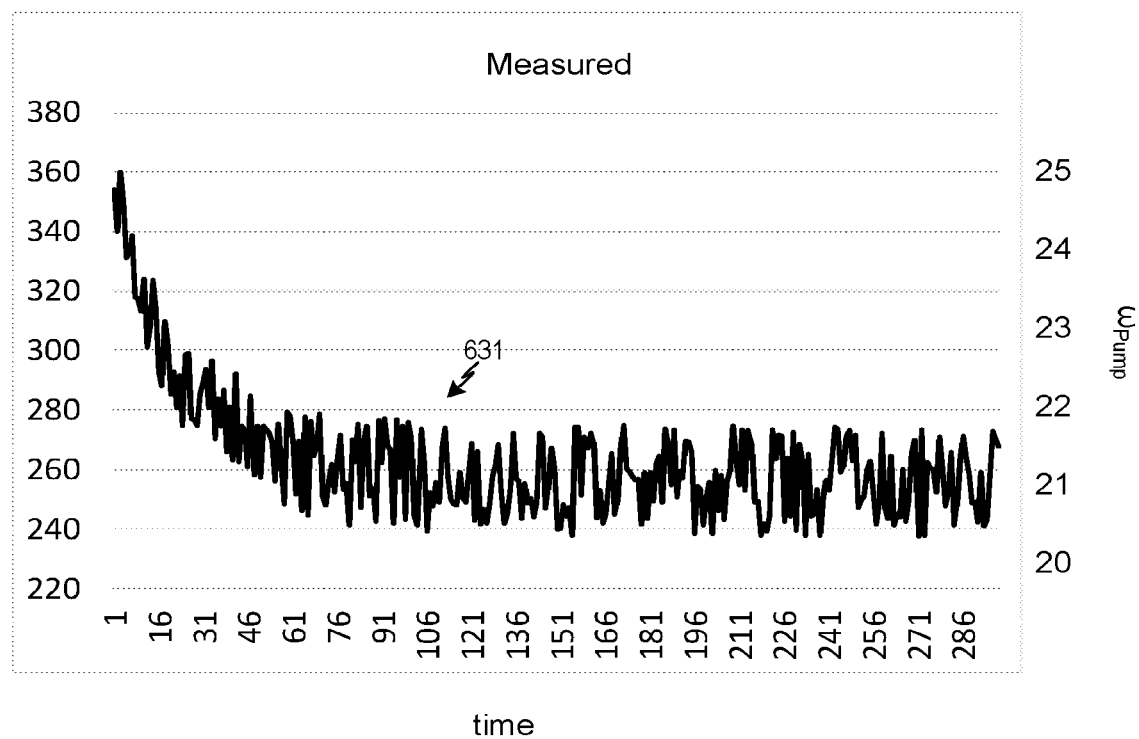
FIGS. 14A-14B illustrate synchronization dynamically by sampling and extrapolating from a synchronization signal in order to reduce the time of pump synchronization, according to various embodiments of the disclosed subject matter.
Figure 14B:
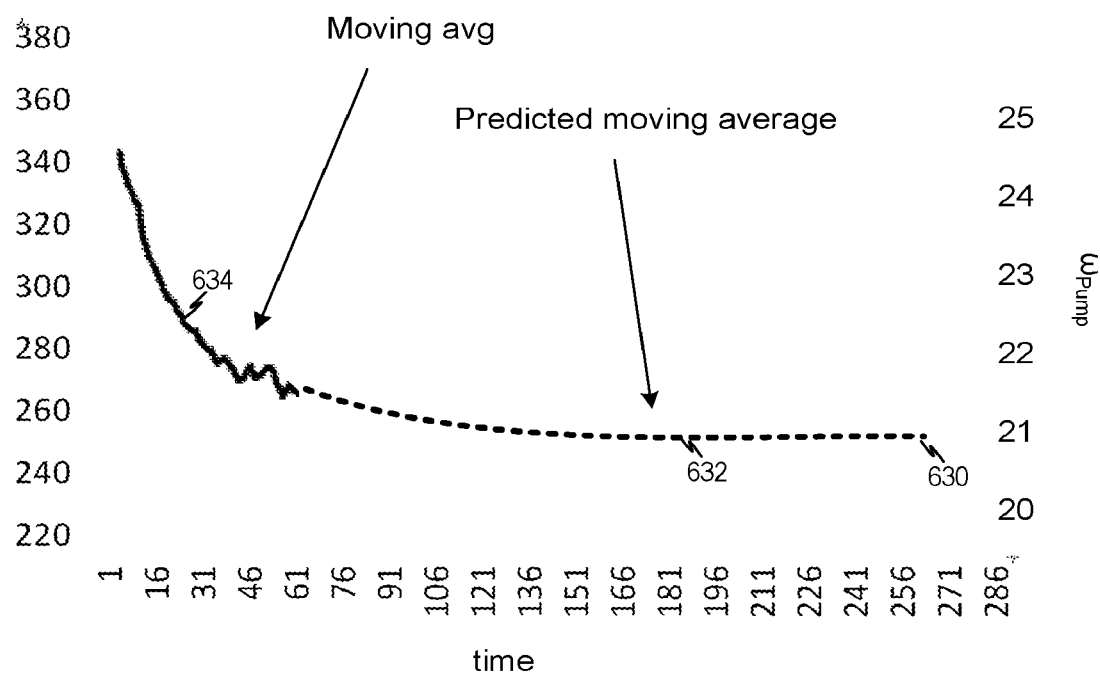

Referring now to FIG. 14A, a profile of instantaneous pressure signal from two synchronized pumps and a corresponding speed of the first pump are shown. The data are merely representative and not limiting of the disclosed embodiments. The variations 631 in the pressure signal are typical, but a general trend is visible. FIG. 14B shows the same data with a moving average calculated from the initial data indicated at 634. The remaining data are indicated at 632 and obtained from a model fitted to the moving average of data 634 to extrapolate a terminal average value indicated at 630 which closely approximates the terminal average obtained by averaging over a final period of the initial data 634. Thus, by fitting an exponential, gaussian, power series, or other function to the data it may be possible to estimate the terminal average after the acquisition of a smaller amount of data over a shorter period of time. The amount of data and the probability of error may vary depending on the conditions, for example, at low flow rates, a longer interval of data may be required. The best parameters to use will be best obtained through laboratory experiments with the specific pump types, materials, and operating conditions for the treatment being performed.

It will be observed that the foregoing shows an example of a way to dynamically determine a synchronized speed of the upstream pump without coming to a full synchronization equilibrium. Thus the embodiment illustrates one example of a method for controlling flow in a fluid circuit, the method being applicable to any blood treatment system that regulates the net ultrafiltration of a patient by balancing fluid withdrawn from a blood treatment device against fluid pumped into the blood treatment device by controlling the relative volume displaced during a treatment by independently-regulated inflow and outflow volumetric pumps. In the method, during a testing mode, the controller connects the inflow and outflow pumps directly while measuring a change in a flow property. The flow property may be flow rate, pressure, or mass. Next, the controller stores synchronized flow data representing the change measured by said measuring and then calculates, from the synchronized flow data, control parameters for regulating the inflow and outflow volumetric pumps. The method continues with performing a treatment including controlling a net flow of fluid to or from a patient by controlling said inflow and outflow volumetric pumps responsively to said control parameters. During the testing mode, the inflow and outflow pumps are not adjusted to be synchronized fully. In particular embodiments the operation of connecting the inflow and outflow pumps directly includes connecting the inflow and outflow pumps through a blood treatment device. In additional embodiments, the operation of connecting the inflow and outflow pumps directly includes defining a fixed-volume flow channel between the inflow and outflow pumps. The flow property may include pressure. The method may further include, during the testing mode, calculating a moving average of the flow property and fitting the same to a curve, wherein the calculating includes fitting the curve to a resulting fitted curve. The method may further include calculating, during the testing mode, a moving average of the flow property and fitting the same to a curve, wherein the calculating includes extrapolating the fitted curve to a corresponding point in pump-speed-to-time curve where the curve is calculated to be flat.

The above methods may be implemented by a controller of a treatment machine. For example, a system for controlling flow in a fluid circuit may have a blood treatment system with a reconfigurable fluid circuit and blood treatment device (for example a disposable fluid circuit and actuators controlled by the machine to define multiple flow paths through the fluid circuit). The system may have inflow and outflow volumetric pumps that are controlled by the controller to regulate the net ultrafiltration of a patient by balancing fluid withdrawn from a blood treatment device against fluid pumped into the blood treatment device by controlling the relative volume displaced during a treatment by independently regulating the speeds of the inflow and outflow volumetric pumps. The controller may receive signals from the flow a sensor indicating the flow property.

Figure 15A:
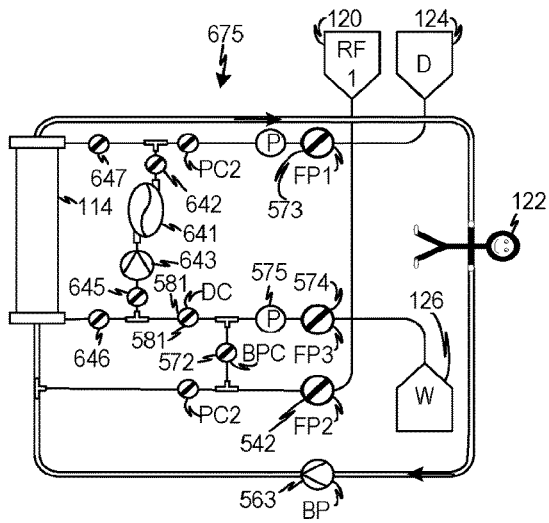
FIGS. 15A-15C show a system and method in which a zero transmembrane flow is established without halting the flow of treatment fluid according to various embodiments of the disclosed subject matter.

Referring now to FIG. 15A, an additional mechanism is described for providing a zero transmembrane flow condition to allow the measurement of treatment device pressure at this condition. The circuit 675 of FIG. 15A may correspond to that of FIG. 11 or a subset thereof with an additional set of components. The added components include the following. A multi-chamber element 641 has a rigid housing and a flexible diaphragm dividing the internal volume of the multi-chamber element 641 such that as one side of the diaphragm receives a fluid at one end of the multi-chamber element 641, the other side's volume is diminished by precisely the same amount forcing an equal volume of fluid out the other end. Thus, as a pump 643 forces fluid into the multi-chamber element 641, fluid from the other end is pushed out at the same rate as pumped in. Pinch clamps 647 and 646 as well as pinch clamps 645 and 642 serve to allow the controller to selectively isolate the multi-chamber element 641 and the treatment device 114 as will be observed from the following description.

Figure 15B:
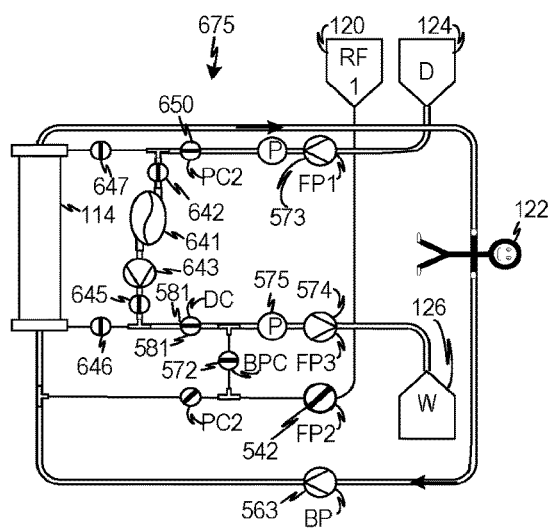
Figure 15C:
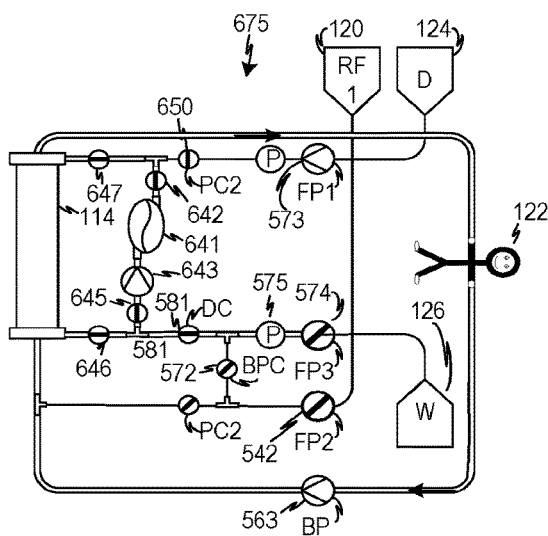

FIG. 15B shows the circuit 675 in a configuration for filling a fresh treatment fluid side of the multi-chamber element 641. Blood is pumped by a blood pump 563 as indicated. The fresh treatment fluid pump 573 and pump 643 are operated with clamps 650, 642, 645, and 581 in open positions to flow treatment fluid into one side of the multi-chamber element 641 while emptying the other side into the waste line. The pump 643 is operated in a reverse direction as indicated by the direction of arrowhead in the pump symbol. Effluent pump 574 may be operated to convey waste fluid to the drain (or waste collector) 126. This operation charges the multi-chamber element 641 with fresh treatment fluid from the treatment fluid source 124. FIG. 15C shows a closed loop being formed by operation of the indicated clamps with the pump 643 operated in the forward direction. The volume of the closed loop flow path is completely fixed as can be confirmed by inspection and the description of multi-chamber element 641. Thus, even as there is a flow in the non-blood compartment through the treatment device 114, the transmembrane flow is zero. The valve 581 is opened to allow the pressure in the closed loop to communicate with the effluent pressure sensor 575. Thus, the pressure of the non-blood compartment of the treatment device 114 may be measured under zero transmembrane flow conditions while fresh treatment fluid is circulated through the treatment device, thereby continuing dialytic cleansing of the blood during this initial step of pump synchronization. The remaining steps may completed as indicated and discussed relative to FIGS. 12D to 12F and other embodiments.

Note that in FIGS. 15A-15C, the double lines indicate flow paths in a flow is established and the single lines indicate a flow path in which no flow is present. Clamps are illustrated as in FIGS. 12A to 12F.

It should be evident from the discussion of FIGS. 12A through 12F and elsewhere that the disclosed subject matter provides a method and a system for controlling fluid flow in a fluid circuit, in embodiments, a fluid circuit that includes treatment fluid and blood portions. The method may include connecting first inflow and outflow lines to one of blood and non-blood compartments of a blood treatment device and connecting second inflow and outflow lines to the other of blood and non-blood compartments of the blood treatment device. Then using a controller, regulating a speed of a first inflow pump connected to the first inflow line to establish a flow into said one of blood and non-blood compartments of a blood treatment device. The method includes regulating a speed of a first outflow pump connected to the first outflow line to establish a flow out of said one of blood and non-blood compartments of a blood treatment device and detecting a pressure of at least one of the blood and non-blood compartments, said pressure indicating a magnitude of a difference between the rates of the flows into and out of said one of blood and non-blood compartments. The method includes calculating a flow control parameter responsively to said pressure and thereafter regulating a net transfer of fluid between the blood and non-blood compartments responsively to the control parameter. In variations, the method includes during the detecting, flowing fluid through the second inflow and outflow lines. In further variations, the method may include, during said detecting, blocking the flow of fluid through the second inflow and outflow lines such that the first inflow and outflow lines and said one of blood and non-blood compartments of a blood treatment device constitute a fixed volume fluid channel.

The pressure may indicate a magnitude of a transmembrane transport between the blood and non-blood compartments. This can be due to the fluid channel being a fixed volume channel or due to the regulation of a pump speed such that a zero-transmembrane flow is established. The pressure at which zero-transmembrane flow is established may be determined automatically by the controller using the methods and mechanisms described herein. The pressure may indicate a magnitude of a transmembrane transport between the blood and non-blood compartments and the calculating includes comparing the pressure to a predefined threshold pressure indicative of zero magnitude of a transmembrane transport between the blood and non-blood compartments.

Thus, it will be observed, that the synchronization method allows the pumps to be synchronized during a treatment mode (albeit, in embodiments, a briefly-interrupted treatment mode) or during a priming stage. It may also be done at other times such as a factory calibration. Advantageously, the synchronization may be done without removing blood from the blood compartment of the treatment device. Further, advantageously, the method may be applied to synchronize inflow and outflow pumps on the blood side or the treatment fluid side of the treatment device. That is, in the embodiment delineated immediately above, the first inflow and outflow lines may be blood lines or treatment fluid lines. Instead of pressure, one may substitute volume flow measurement technique described in connection with FIGS. 6A and 6B or the flow measurement device described with reference to FIG. 5. It should be clear that the pressure signal from which the flow control parameter is calculated may arise due to the blockage of any shift of fluid between the blood and non-blood compartments (e.g., flow through a membrane separating the compartments) or simply the resistance of the membrane. The pressure or the rate of change of pressure may indicate synchronization. In either case, the inflow and outflow pumps may be regulated such that the outflow pump's inlet pressure is at a desired operating pressure determined to be present during a treatment.

The pressure may indicate a magnitude of a transmembrane transport between the blood and non-blood compartments and the calculating may include comparing the pressure to a predefined threshold pressure indicative of zero magnitude of a transmembrane transport between the blood and non-blood compartments. In this case, the method may include determining the predefined threshold pressure by detecting a pressure of the at least one of the blood and non-blood compartments while blocking transport between the blood and non-blood compartments.

The pressure may indicate indicate a magnitude of a transmembrane transport between the blood and non-blood compartments, the calculating may includes comparing the pressure to a predefined threshold pressure indicative of zero magnitude of a transmembrane transport between the blood and non-blood compartments and the method may further include determining the predefined threshold pressure by detecting a pressure of the at least one of the blood and non-blood compartments while blocking transport between the blood and non-blood compartments and while establishing flow through the second inflow and outflow lines at a predefined flow rate.

Figure 16:
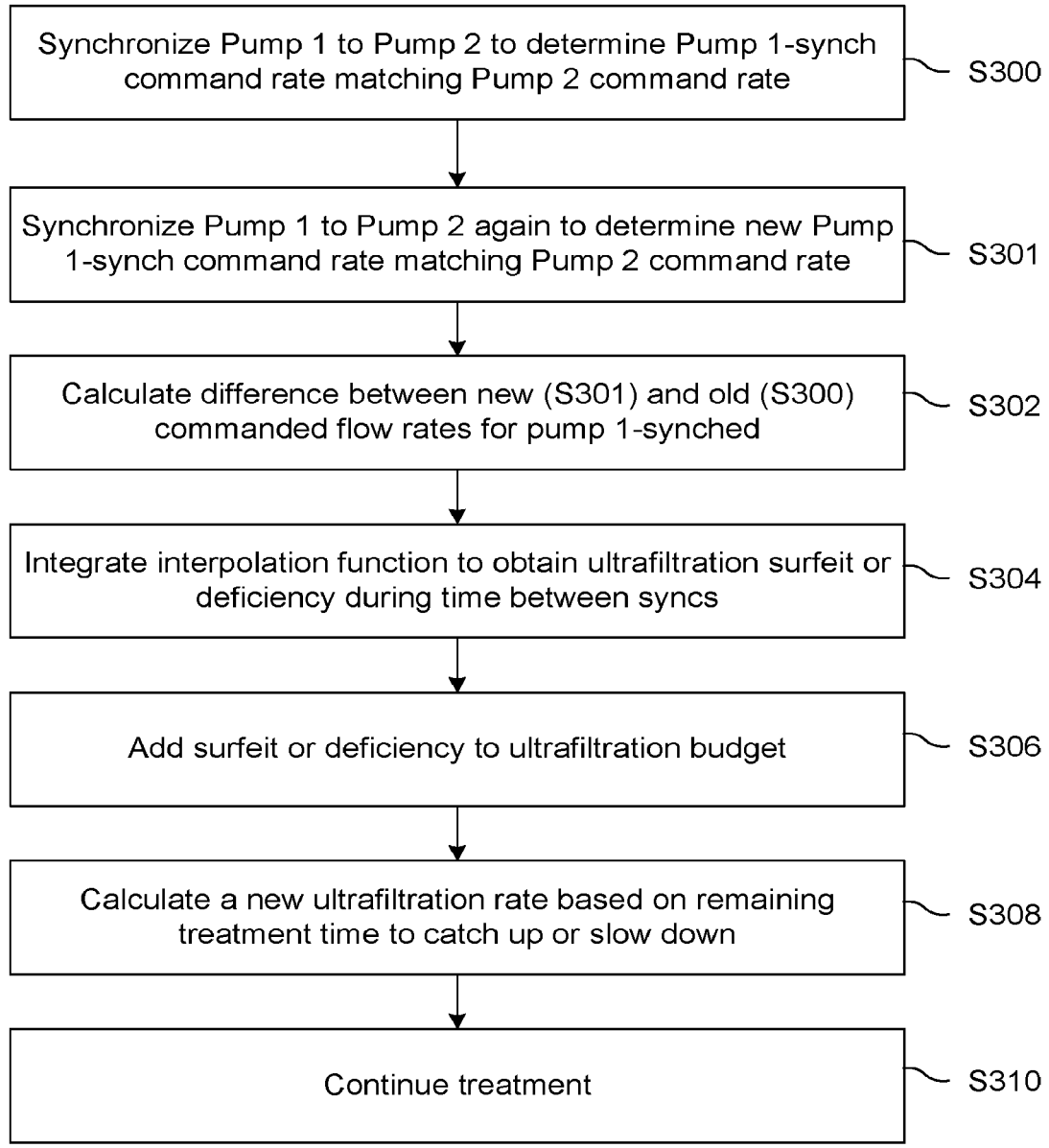
FIG. 16 shows a method of calculating to maintain an ultrafiltration budget over the course of multiple pump synchronization, according to various embodiments of the disclosed subject matter.
Figure 17A:
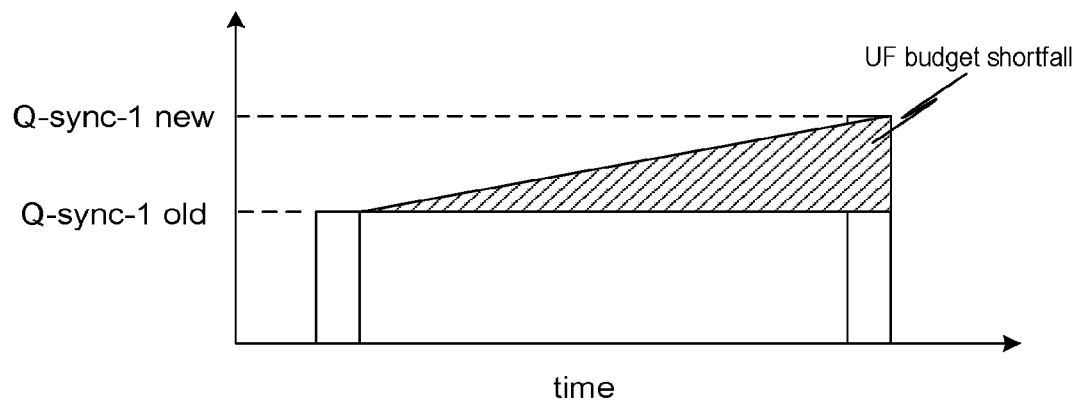
FIGS. 17A-17B illustrate command rate vs. time graphs for purposes of discussing a method of calculating to maintain an ultrafiltration budget over the course of multiple pump synchronization, according to various embodiments of the disclosed subject matter including the embodiments of FIG. 16.

Referring to FIG. 16, in any of the embodiments involving synchronization of two pumps, an error may be generated by a gradual change in the ratio of actual flowrate to commanded flowrate. Thus, at time to, during or before a treatment, a synchronization may be performed S300 in which the commanded rate of an upstream pump, Pump 1, that generates a flow equal to the commanded flow rate for the downstream pump, Pump 2. At a later time, during treatment, the synchronized rate may be updated S301 resulting a new commanded flow rate for Pump 1. At S302, the difference between the new and old commanded flow rates yields a flow rate difference, calculated at S302, which may may arise progressively during the time from the first synchronization to the later one. The flow rate difference may be interpolated between synchronizations and integrated over the assumed distribution of the change in the synchronized commanded rate over time. Assuming the difference accrued linearly over the time between the first synch and the second, a surfeit or deficiency may be calculated from the triangle function, i.e., multiplying the time between synchronizations by ½ the difference between the old and new Pump 1-synched commanded flow rates. If the later synchronized speed is higher, then this amount may be added to the ultrafiltration budget so that the required volume to be ultrafiltered during a remainder of the treatment will be increased. If the later synchronized speed is lower, then this amount may be subtracted from the ultrafiltration budget. S306. At S308, a new ultrafiltration rate may be calculated so that by the time the treatment is completed, the entire budget has been spent. Thereafter the budget may be applied to perform a remainder of the treatment S310 or the process may be repeated if additional synchronizations are to be performed. The parameters are illustrated graphically in FIG. 17A which shows two bar graphs for the two command rates for the first pump after synchronization with an exaggerated change. The shaded triangle superimposed on the bars indicates the cumulative UF shortfall when the new command rate of the first pump shows that a higher rate is required to keep up with the second pump. The symbol Q represents the commanded pump rate.

Figure 17B:
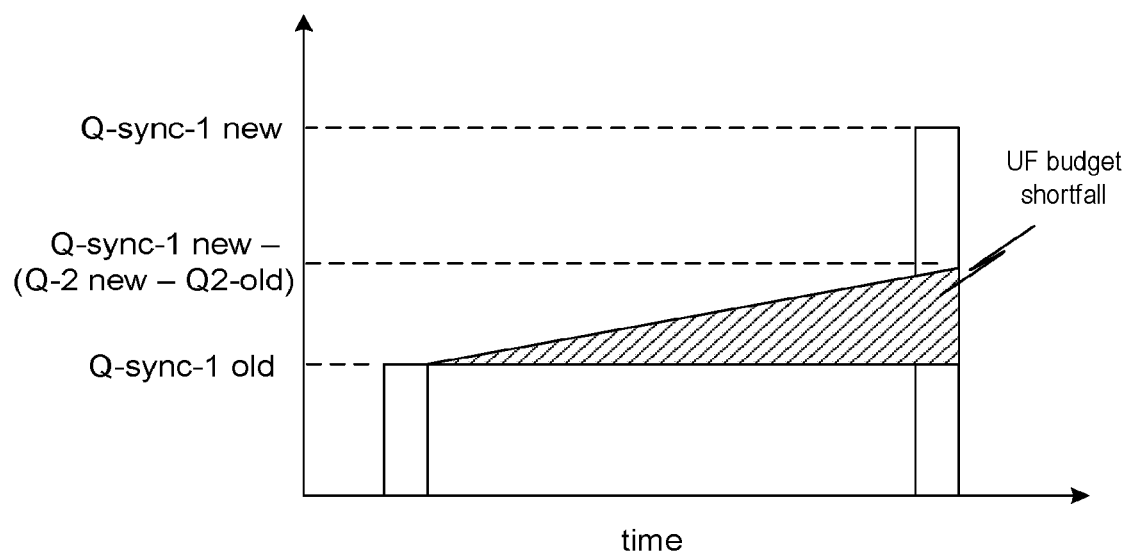

Note that if, in a procedure similar to FIG. 16, is performed, in which a subsequent synchronization is performed at a different Pump 2 commanded flow rate than the first synchronization, a budget surfeit or deficiency can still be calculated if the difference between the old Pump 2 commanded flow rate is removed from the calculation. Thus, subtracting Pump 2-commanded new from Pump 2-commanded old and then subtracting this difference from the old and new Pump 1-commanded-synched rates gives a Pump 1-commanded-synched that can be used to be used for the interpolation calculation. The parameters are illustrated in FIG. 17B. The new synchronized command rate for the first pump is reduced by the difference between the new and old second pump command rates and the ultrafiltration shortfall calculated from the reduced rate as before.

Figure 18A:
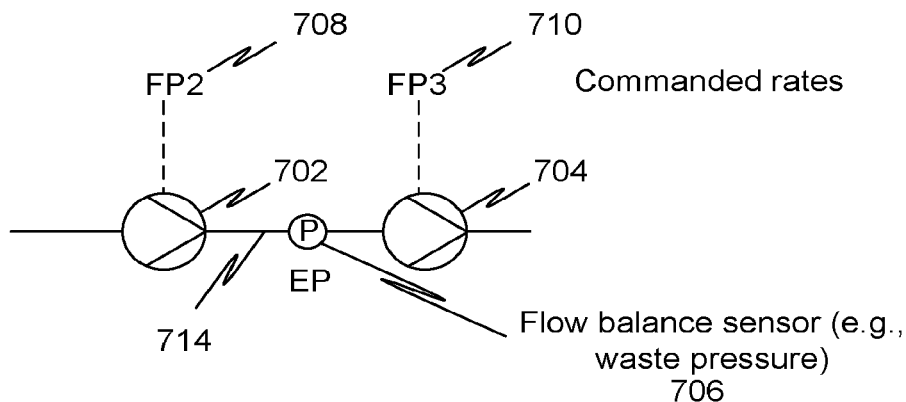
FIGS. 18A-18B illustrate the generation and use of a map of commanded flow and pressure conditions for determining the synchronized command speed of a slave pump according to various embodiments of the disclosed subject matter.
Figure 18B:
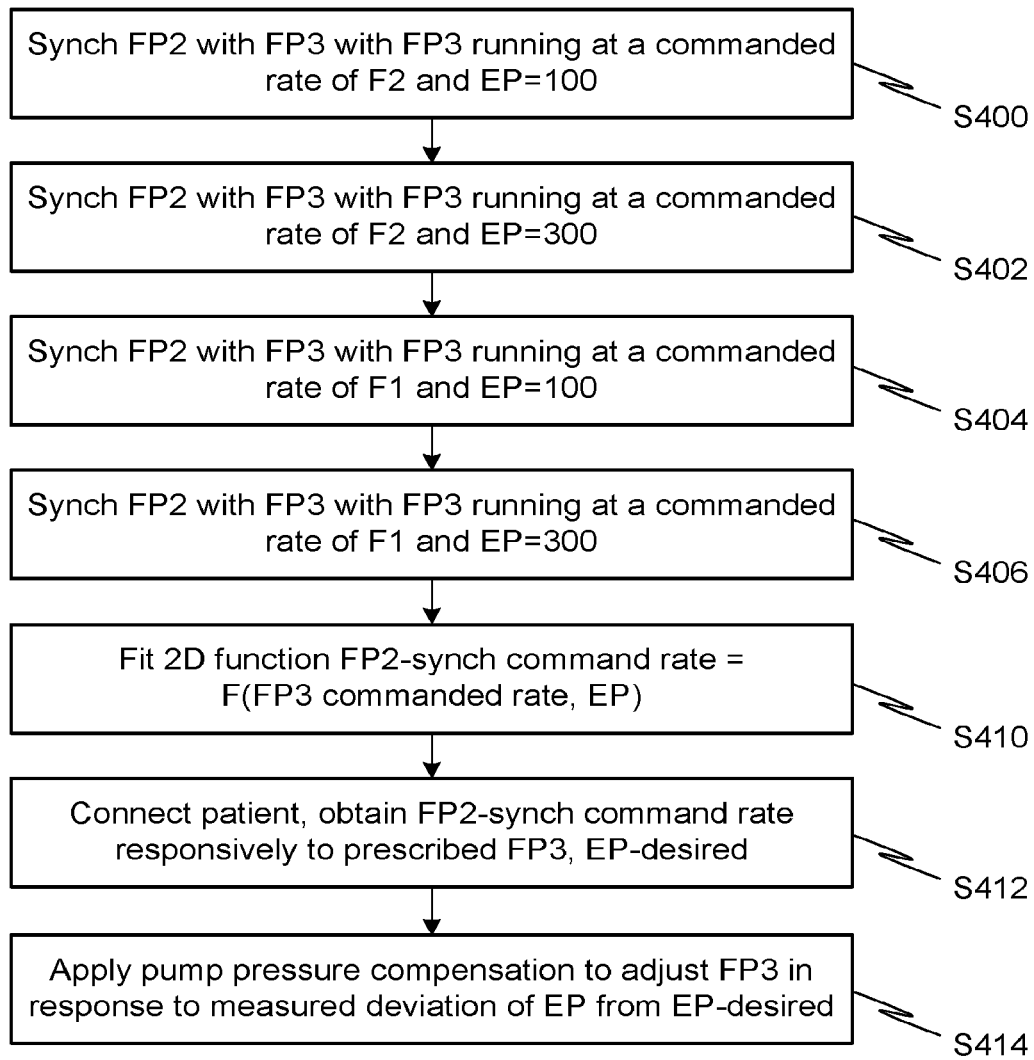

FIGS. 18A-18B illustrate the generation and use of a map of commanded flow and pressure conditions for determining the synchronized command speed of a slave pump 702 responsively to a command speed of a master pump 704 according to various embodiments of the disclosed subject matter. For example, the method may be used to obtain a formula or lookup table to calculated the rates of a replacement fluid pumped by FP2 (FIG. 11) for a given EP and target effluent pump speed (FP3). FIG. 18A shows a generic synchronization scheme with symbols used in FIG. 18B with a first pump 708 (FP2 refers to FIG. 11 dialysate pump as an example) and a second pump 710 (FP3 refers to FIG. 11 waste—or effluent—pump as an example). The two pumps 708 and 710 are linked by a flow channel 714 which may be any of any type including those of the variety of embodiments disclosed herein. The flow balance sensor 706 indicates a flow mismatch between the two pumps 708 and 710. EP indicates the waste line pressure (or effluent pressure) indicated in FIG. 11, for example.

Referring to FIG. 18B at S400, master pump FP3 is run at a commanded rate of F2 and slave pump FP2 is synchronized with it at a predefined pressure of the effluent pump EP, for example, 100 mmHg. The synchronized speed of FP2 and the measured value of EP are recorded. At S402, master pump FP3 is run at a commanded rate of F2 and slave pump FP2 is synchronized with it at a predefined pressure of the effluent pump EP, for example, 300 mmHg. The synchronized speed of FP2 and the measured value of EP are recorded. At S404, master pump FP3 is run at a commanded rate of F3 and slave pump FP2 is synchronized with it at a predefined pressure of the effluent pump EP, for example, 100 mmHg. The synchronized speed of FP2 and the measured value of EP are recorded. At S406, master pump FP3 is run at a commanded rate of F3 and slave pump FP2 is synchronized with it at a predefined pressure of the effluent pump EP, for example, 300 mmHg. The synchronized speed of FP2 and the measured value of EP are recorded. At S410, the recorded speeds and pressure values are fitted to a function to allow the calculation of the synchronized command slave pump rate responsively to the commanded master pump rate and pressure. At S414, the master pump is adjusted according to the pressure compensation coefficient and the difference between the desired EP and the measured magnitude.

At S412, the function is used to calculate a synchronized rate for the slave pump FP2 responsively to a commanded master pump rate and a current effluent pressure EP. The EP pressure used for obtaining the synchronized rates at steps S400-S406 are predefined values. The target independent variable used in S412 is the measured value of the effluent pressure when the blood is flowing through the hemofilter and there is no flow from the effluent pump. At S414, during a hemofiltration treatment, the replacement fluid pump RF2 may be set using the formula or lookup table and a current measured EP. With pressure compensation running, as the effluent pressure departs from the EP originally entered in the formula, the speed of the effluent pump is adjusted accordingly.

In any of the disclosed embodiments, the pressure used for synchronization, which corresponds to a condition of zero flow through the membrane of the treatment device, may be an average of the treatment fluid inlet and outlet pressures, the treatment fluid outlet pressure alone, the pressure of the non-blood compartment of a specially constructed blood treatment device that permits the pressure inside the treatment device to be measured with a single pressure transducer, an average of the blood inlet and outlet pressures, the blood outlet pressure alone, or the pressure of the blood compartment of a specially constructed blood treatment device that permits the pressure inside the treatment device to be measured with a single pressure transducer.

In all of the embodiments, pinch clamps can be replaced with other types of valves and circuit elements, for example, stopcocks, flow switchers, etc.

In any of the disclosed embodiments, the oncotic pressure of blood may be measured by halting a flow of treatment fluid and measuring the pressure difference between the blood and treatment fluid sides of the treatment device. This may be done each time the pumps are synchronized or it may be done independently for the purpose of sampling the blood oncotic pressure. The samples of oncotic pressure may be used to calculate a trend that may be compared to a predefined trend in oncotic pressure. The comparison may indicate that the pace of fluid withdrawal is drawing down the fluid in the blood compartment too fast relative to the patient's ability to replenish it from the upstream fluid compartments such as the interstitial and cellular compartments. The restoration of fluid to the blood compartment is known in the art as fluid rebound. Too high rate of ultrafiltration can cause a temporary hypovolemia which can be detrimental.

The controller may store a predefined rate of change in oncotic pressure that is permitted and slow the rate of ultrafiltration to fall under, or at that rate. The controller may compare the oncotic pressure to a predefined value and control a duration of the treatment so that the oncotic pressure is permitted to reach that value. Note that instead of storing actual values of oncotic pressure, data responsive to it may be stored, such as a derivative of oncotic pressure and or combinations with other variables. For example, oncotic pressure may be combined with a hematocrit sensor signal to produce a combined parameter indicating the patient's fluid load. In further embodiments, the controller may halt, or otherwise vary, the rate of ultrafiltration and combine data indicative of the varying rate of ultrafiltration with the oncotic pressure trend data in order to determine the fluid load or the rate of fluid rebound. A combined parameter such as a ratio of rate of oncotic pressure change to rate of ultrafiltration may be calculated and used to control the rate of ultrafiltration or the duration of ultrafiltration (or duration of treatment). The rate of ultrafiltration may be varied continuously during a treatment cycle responsively to the trend. The rate may be varied so as to decline progressively during a treatment according to predefined constraints on the oncotic pressure or rates of change thereof. As indicated, the oncotic pressure may indicate when the patient has reached a dry weight by measuring the magnitude of oncotic pressure relative to a predefined value (which may be custom for the patient) or the rate of fluid rebound, or the magnitude of the change in oncotic pressure over a test interval during which a predefined rate of ultrafiltration (for example zero rate of ultrafiltration) is maintained.

In all of the embodiments, pinch clamps can be replaced with other types of valves and circuit elements, for example, stopcocks, flow switchers, etc.

In any of the embodiments, a newly connected fluid circuit, connected to a treatment machine having sensors and actuators to engage it, may be subjected to a break-in interval during priming to condition the pumping tube segments before synchronization is performed, or at least relied upon for fluid balance. In an embodiment, in a treatment machine that controls the total volume of fluid flowing into or from a patient against the total volume of fluid drawn from the patient by regulating the relative speeds of peristaltic pumps that flow fluid in a fluid circuit connected to the patient, a special priming mode is implemented. In the priming mode, fluid is pumped through the fluid circuit to prime at least the treatment fluid portion of the attached fluid circuit. A predefined break-in period sufficient to subject the inflow and outflow treatment fluid pumps—the pumps relied upon for fluid balance and ultrafiltration—are subjected to a predefined number of roller strikes prior to performing a synchronization. The break-in interval, in embodiments, may last for greater than five minutes, before establishing a synchronization mode or a treatment in which the peristaltic pumps are relied upon to control a net flow of fluid into or from the patient. In embodiments, the treatment machine is a hemodialysis machine or a hemofiltration machine where the pumps regulate the flow of dialysate into and out of a dialyzer or hemofilter.

Note that as used herein, embodiments refer to the embodiments described in the specification as well as any independent claim and any combination of an independent claim with any combination or sub-combination of the claims depending from an independent claim.

In the foregoing embodiments, the fresh treatment fluid pump pumping rate was determined by the controller, during treatment, from a function, or equivalent, that depended on the rate of the waste treatment fluid pump and the blood compartment pressure (Ave Pb). In alternative embodiments, the fresh treatment fluid pump may be feedback controlled on a balanced pressure signal calculated as the difference between the non-blood compartment pressure, Ave Ptf, and Ave Pb offset by the error and oncotic pressure which are both stored by the controller. Then the determined fresh treatment fluid pumping rate can be changed to obtain the prescribed ultrafiltration rate. In the modified method, S72 is replaced by an operation in which the fresh treatment fluid pump is negative feedback controlled by the calculated error signal. This may be employed, for example instead of the feedforward technique of S72.

In the foregoing embodiments, the TMP is provided as a function of Ave Pb and Qtfw, however, the TMP error may not be a function of these independent variables in which case it may be stored as a fixed value in the controller.

Note that as the term is used herein, "balanced" flow may refer to equal flows or flows that differ by a predefined amount, for example to account for ultrafiltration. During synchronizations, balanced flows may have a zero differential, however, an arbitrary predefined offset from equal flows may still be accommodated using the techniques of synchronization, as should be clear to the skilled practitioner. As term is used herein, balanced may refer to flows that are balanced but offset by a predefined ultrafiltration rate.

In any of the embodiments, the fluid in the treatment fluid circuit and treatment device non-blood compartment may be a priming fluid as is used commonly during priming stage in preparation for a treatment.

In any of the embodiments, the ultrafiltrate or net transfer of fluid from a patient can be positive or negative. A negative ultrafiltrate refers to a net transfer of fluid to a patient while a positive ultrafiltrate refers to a net transfer from a patient. The term balanced in reference to flow may refer to zero net ultrafiltrate volume or rate or a target net ultrafiltrate volume or rate. It does not necessarily mean equal flows in and out of a priming fluid source/sink or patient.

In other embodiments, the oncotic pressure of blood may be measured as described above and used for real-time feedback control of the difference in the average pressure in the blood compartment minus the pressure in the treatment fluid compartment (the compartments being compartments of the blood treatment device) minus the oncotic pressure. The real time feedback control on the pressure difference may continue during a treatment to control the relative speeds of the treatment fluid pumps in a configuration such as that of FIG. 3A and FIG. 7. The oncotic pressure may be measured again at certain points during treatment and used to provide the other functions discussed above.

According to first embodiments, the disclosed subject matter includes an apparatus for controlling flow in a fluid circuit with a controller connected to a data store that stores parameters and procedural data. A treatment machine with arterial and venous blood pump actuators is connected to be controlled by the controller. The treatment machine has a medicament pump actuator and a valve actuator connected to be controlled by the controller. The treatment machine has at least one pressure sensor. The treatment machine has a receiving adapter shaped to receive a blood circuit has arterial and venous lines joined by a treatment device such that the arterial and venous pump actuators control flow to and from the treatment device and to permit the at least one pressure sensor to indicate pressure in the blood circuit, respectively. The treatment machine receiving adapter is further shaped to receive a medicament circuit has fresh and waste lines joined by the same treatment device such that medicament pump is able to pump medicament through one of the fresh and waste lines and the valve actuator is able to prevent flow in the other of the fresh and waste lines. The treatment component is of a type that permits a transfer of fluid between the predefined type of blood circuit and the predefined type of medicament circuit. The procedural data defines a method of regulating a ratio of arterial and venous blood flow rates by controlling speeds of the arterial and blood pump actuators over a treatment interval in order to generate a net fluid transfer in an attached instance of said blood circuit responsively to an ultrafiltrate parameter and a compensation parameter stored in the data store. The ultrafiltrate parameter indicates said net fluid transfer. The procedural data further defines a method of calculating the compensation parameter according to which the controller controls the medicament pump and the valve actuator to block flow into and out of the treatment device and controls the arterial and venous pump actuators to achieve an equal flow through the treatment device through error control responsively to the pressure indicated by the at least one pressure sensor. The calculating is responsive to a ratio of commanded speeds of said arterial and venous pump actuators.

Variations of the first embodiments include further first embodiments in which the treatment device is a dialyzer. Variations of the first embodiments include further first embodiments in which the treatment device separates the blood and medicament circuits by a membrane. Variations of the first embodiments include further first embodiments in which the ultrafiltrate parameter indicates a net ultrafiltrate volume for a single treatment cycle. Variations of the first embodiments include further first embodiments in which the valve actuator is a pinch clamp that is operated by a linear actuator. Variations of the first embodiments include further first embodiments in which the pinch clamp engages a tube portion of said medicament circuit. Variations of the first embodiments include further first embodiments that include a replacement fluid pump actuator, connected to be controlled by the controller, that is positioned such that the receiving adapter engages a replacement fluid line that connects a source of replacement fluid to said blood circuit for predilution or postdilution of blood. Variations of the first embodiments include further first embodiments in which according to the method defined by said procedural data, the controller controls the replacement fluid pump actuator to block flow into and out of the blood circuit, except by way of the arterial and venous lines, when said controller controls the arterial and venous pump actuators to achieve an equal flow through the treatment device. Variations of the first embodiments include further first embodiments that include a drug pump actuator, connected to be controlled by the controller, that is positioned such that the receiving adapter engages a replacement fluid line that connects a source of a drug to said blood circuit injection into blood flowing in said blood circuit. Variations of the first embodiments include further first embodiments in which according to the method defined by said procedural data, the controller controls the drug pump actuator to block flow into and out of the blood circuit, except by way of the arterial and venous lines, when said controller controls the arterial and venous pump actuators to achieve an equal flow through the treatment device.

According to second embodiments, the disclosed subject matter includes an apparatus for controlling flow in a fluid circuit. The apparatus has a treatment machine with pumping actuators, sensors, at least one flow regulator. The treatment machine has a controller connected to control the pumping actuators and at least one flow regulator, receive signals from the sensors in order to implement a therapeutic treatment in a treatment mode and perform a synchronization in a synchronization mode. The treatment machine is adapted to receive a predefined fluid circuit has a plurality of fluid lines includes first and second fluid lines and other fluid lines all interconnected by the fluid circuit, each of the fluid lines is used to transport a fluid during the treatment mode. The at least one flow regulator is arranged to selectively block flow in a respective one of said fluid lines. The plurality of pump actuators each is arranged to selectively pump fluid or block flow in a respective one of said fluid lines, first and second of the pump actuators is engaged with the first and second fluid lines. The controller is programmed to, during the synchronization mode:
command first and second pump actuators of the plurality of pump actuators to flow fluid between the first and second fluid lines;
block flow in the plurality of fluid lines other than the first and second fluid lines to define a fixed volume flow channel between the first and second fluid lines; and
regulate the relative speeds of the first and second pump actuators responsively to a pressure sensor of the sensors to estimate relative rates of said first and second pump actuators that achieve a constant pressure in the fixed volume flow channel.

The controller is further programmed to calculate a control parameter responsive to said relative rates, and, during the treatment mode, regulate a net flow through the other fluid lines by commanding the relative rates of said pump actuators responsively to said control parameter.

Variations of the second embodiments include further second embodiments in which some of the fluid lines are interconnected by a treatment device. Variations of the second embodiments include further second embodiments in which the first and second fluid lines are interconnected by a treatment device. Variations of the second embodiments include further second embodiments in which the treatment device is a dialyzer. Variations of the second embodiments include further second embodiments in which at least one of the fluid lines is connected to a container storing a drug. Variations of the second embodiments include further second embodiments in which at least one of the fluid lines is connected to a container storing a replacement fluid. Variations of the second embodiments include further second embodiments in which the treatment device is a dialyzer, said first fluid line is a fresh dialysate line and said second fluid line is a waste dialysate fluid line. Variations of the second embodiments include further second embodiments in which the first and second fluid lines are interconnected by a treatment device and at least two of the other fluid lines are blood lines connected to the treatment device, the blood lines are interconnected to the first and second fluid lines through a membrane. Variations of the second embodiments include further second embodiments in which the blood lines are engaged by respective pump actuators.

Variations of the second embodiments include further second embodiments in which the first and second fluid lines are engaged by a pump actuator and a valve actuator, respectively. Variations of the second embodiments include further second embodiments in which the first and second fluid lines are blood lines interconnected by a treatment device and at least two of the other fluid lines are medicament lines connected to the treatment device, the blood lines are interconnected to the medicament lines through a membrane. Variations of the second embodiments include further second embodiments in which the medicament lines are engaged by respective pump actuators. Variations of the second embodiments include further second embodiments in which the medicament lines are engaged by a pump actuator and a valve actuator, respectively. Variations of the second embodiments include further second embodiments in which the first and second fluid lines and at least one of the other fluid lines are interconnected by a treatment device. Variations of the second embodiments include further second embodiments in which the first and second fluid lines and at least two of the other fluid lines are interconnected by a treatment device. Variations of the second embodiments include further second embodiments in which the first and second fluid lines and at least two of the other fluid lines are interconnected by a treatment device, the at least two is connected to transport fresh medicament and waste medicament. Variations of the second embodiments include further second embodiments in which the control parameter defines an adjustment of the commanded relative rates of the first and second pump actuators. Variations of the second embodiments include further second embodiments in which the other fluid lines include at least one replacement fluid line connected to a blood line. Variations of the second embodiments include further second embodiments in which the other fluid lines include at least one drug fluid line connected to a blood line. Variations of the second embodiments include further second embodiments in which the first and second fluid lines form a continuous flow path of either blood from a patient that is returned to a patient or medicament that is supplied to a treatment device and drawn from a treatment device. Variations of the second embodiments include further second embodiments in which none of the first, second, or other fluid lines is used exclusively during the synchronization mode for flowing fluid therethrough. Variations of the second embodiments include further second embodiments in which all of the first, second, or other fluid lines carry at least one of blood, medicament, or a drug during the treatment mode, whereby no additional fluid lines are required for the synchronization mode.

According to third embodiments, the disclosed subject matter includes a blood treatment machine that has a controller connected to control fresh and waste treatment fluid pumps connected to flow treatment fluid to and from a blood treatment device has blood and treatment fluid compartments, respectively, a blood pump connected to flow fluid through the blood treatment device blood compartment, and inlet and outlet pressure sensors indicating pressures into and out of the treatment device blood compartment. The controller is programmed to implement a method. The method includes storing operating conditions in a data store, the operating conditions includes combinations of target average blood pressures in the treatment device and target flow rates of the treatment fluid pumps. The method further includes an outer control loop according to which, for each of the average blood pressures, the controller commands the blood pump, with the treatment fluid pumps off, to circulate priming fluid through the treatment device blood compartment at a respective target average blood pressure and records a measured actual average blood compartment pressure in the treatment device, the average is indicated by the inlet and outlet pressure sensors. According to an inner control loop, which may be embedded in the outer control loop, for each of the treatment fluid pump target flow rates that corresponds to a current target blood pressure in the stored operating conditions, the controller commands the treatment fluid pumps to circulate fluid through the treatment device treatment fluid compartment at a respective target treatment fluid flow rate and controlling the absolute and relative rates of fresh and waste treatment fluid pumps to achieve an equilibrium condition of equalized flow and an average pressure indicated by the inlet and outlet pressure sensors equal to said recorded measured actual average blood pressure and records synchronization data includes commanded rates of the treatment fluid pumps and indications by the inlet and outlet pressure sensors corresponding to the equilibrium condition. The method includes fitting a function, or an equivalent of a function (hereafter, operator), to the synchronization data that relates a slave rate of one of the commanded fresh and waste treatment fluid pumps to a combination of a master rate of the other of the commanded fresh and waste treatment fluid pumps and an average of the recorded indications of the inlet and outlet pressure sensors.

Variations of the third embodiments include further third embodiments in which the method further includes controlling a patient's fluid balance responsively to the operator. Variations of the third embodiments include further third embodiments in which the controlling to patient's fluid balance includes controlling a ratio of speeds of said fresh and waste treatment fluid pumps responsively to said operator. Variations of the third embodiments include further third embodiments in which the dimensions of said one of the commanded fresh and waste treatment fluid pump rate are revolutions per unit time. Variations of the third embodiments include further third embodiments in which the controlling a patient's fluid balance includes reading a fresh and waste treatment fluid pump rate or flow rate from a prescription, generating a command to said fresh and waste treatment fluid pumps responsive to said read rate, and controlling a ratio of speeds of said fresh and waste treatment fluid pumps responsively to said operator. Variations of the third embodiments include further third embodiments in which the controlling a patient's fluid balance includes reading a fresh and waste treatment fluid pump rate or flow rate from a prescription, generating a command to operate the other of the commanded fresh and waste treatment fluid pumps at a current commanded speed indicated by said read rate and applying the current commanded speed to said operator, calculating a current measured average blood compartment pressure indicated by the inlet and outlet pressure sensors and applying said current measured average to said operator, and controlling one of said fresh and waste treatment fluid pumps responsively to an output of said operator. Variations of the third embodiments include further third embodiments in which the controlling a patient's fluid balance further includes feedback-controlling the speed of the one of the commanded fresh and waste treatment fluid pumps until a newly calculated average blood compartment pressure indicated by the inlet and outlet pressure sensors is equal to the previously calculated current measured average blood compartment pressure. Variations of the third embodiments include further third embodiments in which the controlling a patient's fluid balance further includes reading ultrafiltration data responsive to an ultrafiltrate volume and changing a ratio of speeds of the fresh and waste treatment fluid pumps responsively to said ultrafiltration data.

According to fourth embodiments, the disclosed subject matter includes, an apparatus for controlling flow in a fluid circuit. A treatment machine has flow regulators and sensors, the flow regulators includes pumping actuators. The treatment machine has a controller connected to control the flow regulators and receive signals from the sensors to implement a therapeutic treatment by regulates the flow of blood and treatment fluid when a predefined fluid circuit is connected in operative engagement with the flow regulators and sensors. The predefined fluid circuit has a plurality of fluid lines includes first and second fluid lines and other fluid lines all interconnected by the fluid circuit, each of the fluid lines are used to transport a fluid during the treatment mode in order to implement the therapeutic treatment. The flow regulators are controlled by the controller, during a synchronization mode thereof, to selectively block flow in first ones of the fluid lines while selectively pumping fluid serially through second ones of the fluid lines such that first and second pumping actuators pump fluid in a fixed volume channel that interconnects the second ones of the fluid lines, the fixed volume channel are sealed in part by the first ones of the fluid lines. The controller, during the synchronization mode, regulates the relative speeds of the first and second pumping actuators responsively to at least one of the sensors to estimate commanded rates of the first and second pumping actuators corresponding to equal flows throughout the fixed volume channel and deriving one or more control parameters permitting the controller to implement a predefined ratio of flow rates by the first and second pumping actuators during a treatment mode of the controller. The flow regulators are controlled by the controller to, during the treatment mode, regulate a net flow through the second ones of the fluid lines by commanding the relative rates of the first pump actuator responsively to the one or more control parameters.

In additional embodiments thereof, the fourth embodiments include ones in which some of the first and second fluid lines are interconnected by a treatment device. In additional embodiments thereof, the fourth embodiments include ones in which the first fluid lines are blood lines and the first and second pumping actuators are arterial and venous blood pumping actuators. In additional embodiments thereof, the fourth embodiments include ones in which the treatment device is a dialyzer. In additional embodiments thereof, the fourth embodiments include ones in which at least one of the fluid lines is connected to a container storing a drug. In additional embodiments thereof, the fourth embodiments include ones in which at least one of the fluid lines is connected to a container storing a replacement fluid. In additional embodiments thereof, the fourth embodiments include ones in which the treatment device is a dialyzer and the second fluid lines are fresh dialysate line waste dialysate fluid lines, respectively. In additional embodiments thereof, the fourth embodiments include ones in which the first and second fluid lines are interconnected by a treatment device, the second fluid lines are blood lines and the first and second pumping actuators are fresh and waste treatment fluid blood pumping actuators. In additional embodiments thereof, the fourth embodiments include ones in which the first fluid lines are separated from the second fluid lines by a membrane of the treatment device. In additional embodiments thereof, the fourth embodiments include ones in which during the synchronization mode, the first and second pumping actuators are operated at multiple speeds to generate multiple one or more control parameters by regulates the relative speeds of the first and second pumping actuators to achieve equal flows of multiple magnitudes. In additional embodiments thereof, the fourth embodiments include ones in which the sensors include pressure sensors. In additional embodiments thereof, the fourth embodiments include ones in which pressure data corresponding to signals from the pressure sensors are recorded during the synchronization mode and included in the at least one control parameter, the pressure signals are used by the controller to generate a commanded speed of at least one of the first and second pumping actuators to account for differences between the pressure data and pressure signals during the synchronization mode and the treatment mode. In additional embodiments thereof, the fourth embodiments include ones in which the sensors include a weight sensor, the controller determining equal flows in the second fluid lines from the weight sensor. In additional embodiments thereof, the fourth embodiments include ones in which the controller determines equal flows in the second fluid lines from a state where weight indicated by the weight sensor is unchanging. In additional embodiments thereof, the fourth embodiments include ones in which the sensors include a pressure sensor, the controller determining equal flows in the second fluid lines from the pressure sensor. In additional embodiments thereof, the fourth embodiments include ones in which the controller determines equal flows in the second fluid lines from a state where pressure indicated by the weight sensor is unchanging. In additional embodiments thereof, the fourth embodiments include ones in which the flow regulators include at least one control valve that engages with one of the first fluid lines. In additional embodiments thereof, the fourth embodiments include ones in which the flow regulators include a third pumping actuator that engages with one of the first fluid lines, the third pumping actuator are halted during the synchronization mode to prevent flow in the one of the first fluid lines. In additional embodiments thereof, the fourth embodiments include ones in which the controller establishes the equal flows throughout the fixed volume channel for a predefined interval. In additional embodiments thereof, the fourth embodiments include ones in which the controller derives the at least one control parameter without establishing equal flows throughout the fixed volume channel by fitting a hydraulic model to dynamic data from at least one sensor of the sensors. In additional embodiments thereof, the fourth embodiments include ones in which during the synchronization mode, the controller directly measures a flow rate generated by at least one of the first and second pumping actuators to generate a flow rate parameter, the at least one control parameter includes data responsive to the flow rate parameter. In additional embodiments thereof, the fourth embodiments include ones in which the first fluid lines engage third and fourth pumping actuators, respectively, the third and fourth pumping actuators are halted during the synchronization mode to prevent flow in the one of the first fluid lines.

According to fifth embodiments, the disclosed subject matter includes, an apparatus for controlling flow in a fluid circuit. A treatment machine with flow regulators and sensors, the flow regulators includes pumping actuators includes first and second pumping actuators. The treatment machine has a controller connected to control the flow regulators and receive signals from the sensors to implement a therapeutic treatment by regulates the flow of blood and treatment fluid when a predefined fluid circuit is connected in operative engagement with the flow regulators and sensors. The predefined fluid circuit has a plurality of fluid lines includes first and second fluid lines all interconnected by a treatment device of the fluid circuit, each of the fluid lines are used to transport a fluid during the treatment mode in order to implement the therapeutic treatment. The treatment device has a first compartment connected to the first fluid lines and a second compartment connected to the second fluid lines, the first and second compartments are connected for flow therebetween. The flow regulators are controlled by the controller, at a first time during a synchronization mode thereof, to selectively block flow in the second fluid lines by halting the first and second pumping actuators while selectively pumping fluid through the first fluid lines at a first flow rate and storing first data responsive to a pressure signal from the sensors indicating a pressure of the first or second compartment. The flow regulators are controlled by the controller, at a second time, during the synchronization mode, to regulate the relative speeds of the first and second pumping actuators responsively to the pressure signal to estimate commanded rates of the first and second pumping actuators effective to bring about a predefined relationship between the first data and the pressure signal and to calculate and record at least one first control parameter indicating a relationship between the speeds of the first and second pumping actuators when the predefined relationship exists at the first flow rate. The controller controls the first and second pumping actuators responsively to the at least one first control parameter to implement a predefined ratio of flow rates during a treatment mode.

In additional embodiments thereof, the fifth embodiments include ones in which the predefined relationship is equality of pressures indicated by the pressure signal and the first data. In additional embodiments thereof, the fifth embodiments include ones in which the flow regulators are controlled by the controller, at a third time during the synchronization mode thereof, to selectively block flow in the second fluid lines by halting the first and second pumping actuators while selectively pumping fluid through the first fluid lines at a second flow rate and to store second data responsive to the pressure signal. The flow regulators are controlled by the controller, at a fourth time, during the synchronization mode, to regulate the relative speeds of the first and second pumping actuators responsively to the pressure signal to estimate commanded rates of the first and second pumping actuators effective to bring about the predefined relationship between the second data and the pressure signal and to calculate and record at least one second control parameter indicating a relationship between the speeds of the first and second pumping actuators when the predefined relationship exists at the second flow rate. The controller calculates at least one third control parameter responsive to the at least one first and at least one second control parameters and controlling the first and second pumping actuators responsively to the third control parameter to cause a predefined ratio of flow rates, during a treatment mode, in the second fluid lines.

In additional embodiments thereof, the fifth embodiments include ones in which the first or second compartment is the first compartment. In additional embodiments thereof, the fifth embodiments include ones in which the first or second compartment is the second compartment. In additional embodiments thereof, the fifth embodiments include ones in which some of the first and second fluid lines are interconnected by the treatment device. In additional embodiments thereof, the fifth embodiments include ones in which the first fluid lines are blood lines and the second lines are medicament lines. In additional embodiments thereof, the fifth embodiments include ones in which the second fluid lines are blood lines and the first fluid lines are medicament lines. In additional embodiments thereof, the fifth embodiments include ones in which at least one of the fluid lines is connected to a container storing a drug. In additional embodiments thereof, the fifth embodiments include ones in which at least one of the fluid lines is connected to a container storing a replacement fluid. In additional embodiments thereof, the fifth embodiments include ones in which the treatment device is a dialyzer and the second fluid lines are fresh dialysate line waste dialysate fluid lines, respectively. In additional embodiments thereof, the fifth embodiments include ones in which the first and second fluid lines are interconnected by a treatment device, the second fluid lines are blood lines and the first and second pumping actuators are fresh and waste treatment fluid blood pumping actuators. In additional embodiments thereof, the fifth embodiments include ones in which the first fluid lines are separated from the second fluid lines by a membrane of the treatment device which permits flow of at least water therethrough. In additional embodiments thereof, the fifth embodiments include ones in which pressure data corresponding to the pressure signals are recorded during the synchronization mode and included in the at least one first control parameter, the pressure signals are used by the controller to generate a commanded speed of at least one of the first and second pumping actuators to account for differences between the pressure data and pressure signals during the synchronization mode and the treatment mode. In additional embodiments thereof, the fifth embodiments include ones in which the first and second fluid lines are interconnected by a treatment device, the second fluid lines are blood lines and the first and second pumping actuators are fresh and waste treatment fluid blood pumping actuators. In additional embodiments thereof, the fifth embodiments include ones in which the first fluid lines are separated from the second fluid lines by a membrane of the treatment device which permits flow of at least water therethrough. In additional embodiments thereof, the fifth embodiments include ones in which pressure data corresponding to the pressure signal are recorded during the synchronization mode and included in the at least one third control parameter, the pressure signals are used by the controller to generate a commanded speed of at least one of the first and second pumping actuators to account for differences between the pressure data and pressure signals during the synchronization mode and the treatment mode. In additional embodiments thereof, the fifth embodiments include ones in which at least one of the fluid lines is connected to a container storing a drug. In additional embodiments thereof, the fifth embodiments include ones in which at least one of the fluid lines is connected to a container storing a replacement fluid. In additional embodiments thereof, the fifth embodiments include ones in which the treatment device is a dialyzer and the second fluid lines are fresh dialysate line waste dialysate fluid lines, respectively. In additional embodiments thereof, the fifth embodiments include ones in which the first and second fluid lines are interconnected by a treatment device, the second fluid lines are blood lines and the first and second pumping actuators are fresh and waste treatment fluid blood pumping actuators. In additional embodiments thereof, the fifth embodiments include ones in which the first fluid lines are separated from the second fluid lines by a membrane of the treatment device which permits flow of at least water therethrough. In additional embodiments thereof, the fifth embodiments include ones in which pressure data corresponding to the pressure signals are recorded during the synchronization mode and included in the at least one first control parameter, the pressure signals are used by the controller to generate a commanded speed of at least one of the first and second pumping actuators to account for differences between the pressure data and pressure signals during the synchronization mode and the treatment mode. In additional embodiments thereof, the fifth embodiments include ones in which the first and second fluid lines are interconnected by a treatment device, the second fluid lines are blood lines and the first and second pumping actuators are fresh and waste treatment fluid blood pumping actuators. In additional embodiments thereof, the fifth embodiments include ones in which the first fluid lines are separated from the second fluid lines by a membrane of the treatment device which permits flow of at least water therethrough. In additional embodiments thereof, the fifth embodiments include ones in which pressure data corresponding to the pressure signal are recorded during the synchronization mode and included in the at least one third control parameter, the pressure signals are used by the controller to generate a commanded speed of at least one of the first and second pumping actuators to account for differences between the pressure data and pressure signals during the synchronization mode and the treatment mode. In additional embodiments thereof, the fifth embodiments include ones in which the first and second flow rates are selected to be typical of flow rates during the treatment mode. In additional embodiments thereof, the fifth embodiments include ones in which the at least one third control parameter are parameters of a function or lookup table fitted to speed and pressure data. In additional embodiments thereof, the fifth embodiments include ones in which wherein: the controller is connected to a flow restrictor that permits the pressure in the first or second compartment to be controlled by the controller when a flow is established therethrough, and the controller generates additional control parameters responsively various combinations and pressures and flows in the first or second compartment which are used by the controller to calculate the third control parameter. In additional embodiments thereof, the fifth embodiments include ones in which the controller reestablishes the synchronization mode responsively to an event after first establishing the treatment mode, and then reestablishes the treatment mode with a new at least one first control parameter. In additional embodiments thereof, the fifth embodiments include ones in which the event includes a lapse of a predefined interval of time since an initial establishment of the treatment mode. In additional embodiments thereof, the fifth embodiments include ones in which the predefined ratio is responsive to a predefined ultrafiltration rate and the event includes a change in the predefined ultrafiltraton rate. In additional embodiments thereof, the fifth embodiments include ones in which wherein the first fluid lines are blood lines and the second lines are medicament lines or the second fluid lines are blood lines and the first lines are medicament lines, wherein the event includes a change pressure in at least one of the blood lines. In additional embodiments thereof, the fifth embodiments include ones in which the first fluid lines are blood lines and the second lines are medicament lines or the second fluid lines are blood lines and the first lines are medicament lines, wherein the event includes a change pressure in at least one of the medicament lines. In additional embodiments thereof, the fifth embodiments include ones in which the event includes the receipt by the controller of a command from a user interface to reestablish the synchronization mode. In additional embodiments thereof, the fifth embodiments include ones in which the event includes the completion of an alarm and recover mode during which the treatment mode was stopped for at least a predefined period of time. In additional embodiments thereof, the fifth embodiments include ones in which the event includes a change in absolute flow rate generated by at least one the first and second pumping actuators. In additional embodiments thereof, the fifth embodiments include ones in which the event includes the reestablishment of the treatment mode after a stoppage for the change of a component of the fluid circuit. In additional embodiments thereof, the fifth embodiments include ones in which the controller reestablishes the synchronization mode responsively to an event after first establishing the treatment mode, and then reestablishes the treatment mode with a new at least one first control parameter. In additional embodiments thereof, the fifth embodiments include ones in which the event includes a lapse of a predefined interval of time since an initial establishment of the treatment mode. In additional embodiments thereof, the fifth embodiments include ones in which the predefined ratio is responsive to a predefined ultrafiltration rate and the event includes a change in the predefined ultrafiltraton rate. In additional embodiments thereof, the fifth embodiments include ones in which the first fluid lines are blood lines and the second lines are medicament lines or the second fluid lines are blood lines and the first lines are medicament lines, wherein the event includes a change pressure in at least one of the blood lines. In additional embodiments thereof, the fifth embodiments include ones in which the first fluid lines are blood lines and the second lines are medicament lines or the second fluid lines are blood lines and the first lines are medicament lines wherein the event includes a change pressure in at least one of the medicament lines. In additional embodiments thereof, the fifth embodiments include ones in which the event includes the receipt by the controller of a command from a user interface to reestablish the synchronization mode. In additional embodiments thereof, the fifth embodiments include ones in which the event includes the completion of an alarm and recover mode during which the treatment mode was stopped for at least a predefined period of time. In additional embodiments thereof, the fifth embodiments include ones in which the event includes a change in absolute flow rate generated by at least one the first and second pumping actuators. In additional embodiments thereof, the fifth embodiments include ones in which the event includes the reestablishment of the treatment mode after a stoppage for the change of a component of the fluid circuit. In additional embodiments thereof, the fifth embodiments include ones in which the synchronization mode occurs during priming of a blood circuit in advance of the treatment mode. In additional embodiments thereof, the fifth embodiments include ones in which the first flow rate is equal to a rate prescribed for flow through the first fluid lines during the treatment mode. In additional embodiments thereof, the fifth embodiments include ones in which the speeds of the first and second pumping actuators are responsive to a treatment fluid flow rate prescribed for flow through second fluid lines during the treatment mode. In additional embodiments thereof, the fifth embodiments include ones in which the speeds of the first and second pumping actuators are responsive to a treatment fluid flow rate prescribed for flow through second fluid lines during the treatment mode. In additional embodiments thereof, the fifth embodiments include ones in which the first flow rate is equal to a rate prescribed for flow through the first fluid lines during the treatment mode. In additional embodiments thereof, the fifth embodiments include ones in which the speeds of the first and second pumping actuators are responsive to a treatment fluid flow rate prescribed for flow through second fluid lines during the treatment mode. In additional embodiments thereof, the fifth embodiments include ones in which the speeds of the first and second pumping actuators are responsive to a treatment fluid flow rate prescribed for flow through second fluid lines during the treatment mode. In additional embodiments thereof, the fifth embodiments include ones in which the controller stores a difference in pressure between the first and second compartments that exists at at least one of the first and second times and outputs the difference in pressure as an indication of oncotic pressure. In additional embodiments thereof, the fifth embodiments include ones in which controller stores a difference in pressure between the first and second compartments that exists at at least one of the first and second times, the controller calculating the first control parameter responsively top the difference in pressure. In additional embodiments thereof, the fifth embodiments include ones in which the controller stores a difference in pressure between the first and second compartments that exists at at least one of the first and second times, calculates a diagnostic parameter responsive to the difference in pressure and outputs the diagnostic parameter. In additional embodiments thereof, the fifth embodiments include ones in which the diagnostic parameter includes a patient's blood hematocrit. In additional embodiments thereof, the fifth embodiments include ones in which the diagnostic parameter includes a patient's water level.

According to sixth embodiments, the disclosed subject matter includes, a method for controlling fluid flow in a fluid circuit. The method includes connecting first inflow and outflow lines to one of blood and non-blood compartments of a blood treatment device. The method includes connecting second inflow and outflow lines to the other of blood and non-blood compartments of the blood treatment device. The method includes using a controller, regulating a speed of a first inflow pump, connected to the first inflow line, to establish a flow into the one of blood and non-blood compartments of a blood treatment device. The method includes regulating a speed of a first outflow pump connected to the first outflow line to establish a flow out of the one of blood and non-blood compartments of a blood treatment device and detecting a pressure of at least one of the blood and non-blood compartments, the pressure indicating a magnitude of a difference between the rates of the flows into and out of the one of blood and non-blood compartments. The method includes calculating a flow control parameter responsively to the pressure. The method includes thereafter regulating a net transfer of fluid between the blood and non-blood compartments responsively to the control parameter.

In additional embodiments thereof, the sixth embodiments include ones that further include, during the detecting, flowing fluid through the second inflow and outflow lines.

In additional embodiments thereof, the sixth embodiments include ones that further include, during the detecting, blocking the flow of fluid through the second inflow and outflow lines such that the first inflow and outflow lines and the one of blood and non-blood compartments of a blood treatment device constitute a fixed volume fluid channel.

In additional embodiments thereof, the sixth embodiments include ones in which the pressure indicates a magnitude of a transmembrane transport between the blood and non-blood compartments. In additional embodiments thereof, the sixth embodiments include ones in which, wherein the pressure indicates a magnitude of a transmembrane transport between the blood and non-blood compartments and the calculating includes comparing the pressure to a predefined threshold pressure indicative of zero magnitude of a transmembrane transport between the blood and non-blood compartments. In additional embodiments thereof, the sixth embodiments include ones in which the pressure indicates a magnitude of a transmembrane transport between the blood and non-blood compartments. The calculating includes comparing the pressure to a predefined threshold pressure indicative of zero magnitude of a transmembrane transport between the blood and non-blood compartments. The variation of the method further includes determining the predefined threshold pressure by detecting a pressure of the at least one of the blood and non-blood compartments while blocking transport between the blood and non-blood compartments.

In additional embodiments thereof, the sixth embodiments include ones in which the pressure indicates a magnitude of a transmembrane transport between the blood and non-blood compartments. The calculating includes comparing the pressure to a predefined threshold pressure indicative of zero magnitude of a transmembrane transport between the blood and non-blood compartments. The method further includes determining the predefined threshold pressure by detecting a pressure of the at least one of the blood and non-blood compartments while blocking transport between the blood and non-blood compartments and while establishing flow through the second inflow and outflow lines at a predefined flow rate. In additional embodiments thereof, the sixth embodiments include ones in which the controller includes an embedded computer with a data store has instructions readable thereby to regulate, detect, and calculate and to store data responsive thereto. In additional embodiments thereof, the sixth embodiments include ones in which the control parameter includes a constant of proportionality that relates a command speed of a slave pump to a command speed of a master pump coinciding with identical flow rates therethrough. In additional embodiments thereof, the sixth embodiments include ones in which the controller adjusts the first outflow pump in response to a predefined ultrafiltration flow rate and the control parameter such that the first outflow pump generates a flow rate that is higher than that of the first inflow pump. In additional embodiments thereof, the sixth embodiments include ones in which the controller continuously updates a speed of the first outflow pump in response to a signal from the pressure. In additional embodiments thereof, the sixth embodiments include ones in which the pressure of at least one of the blood and non-blood compartments is indicated by a pressure in the first inflow line and/or a pressure in the first outflow line. In additional embodiments thereof, the sixth embodiments include ones in which the pressure signal is an average of a pressure in the first inflow line and a pressure in the first outflow line.

According to seventh embodiments, the disclosed subject matter includes a system for controlling fluid flow in a fluid circuit. A blood treatment machine has a controller, the controller is programmable is connected to control a flow control device, a first inflow pump, a first outflow pump and a second inflow pump, and to receive pressure signals from at least one pressure sensor. The first inflow and outflow pumps are engaged with first inflow and outflow lines, respectively, to flow fluid into and out from one of blood and non-blood compartments of a blood treatment device. The second inflow pump is engaged with a second inflow line to flow fluid into the other of the blood and non-blood compartments and the flow control device are engaged with a second outflow line connected to flow fluid out of the other of the blood and non-blood compartments. The controller is connected to at least one pressure sensor that generates a pressure signal indicating a pressure inside at least one of the blood and non-blood compartments, the pressure indicating a magnitude of a difference between the rates of the flows into and out of the one of blood and non-blood compartments. The controller is programmed to, in a synchronization mode, (1) regulate a speed of a first outflow pump connected to the first outflow line to establish a flow out of the one of blood and non-blood compartments of a blood treatment device; and (2) use the pressure signal to calculate a flow control parameter of the first outflow pump responsively to the pressure. The controller is further programmed to, thereafter, in a treatment mode regulate a net transfer of fluid between the blood and non-blood compartments responsively to the control parameter.

In additional embodiments thereof, the seventh embodiments include ones that further include, during the detecting, flowing fluid through the second inflow and outflow lines.

In additional embodiments thereof, the seventh embodiments include ones that further include, during the detecting, blocking the flow of fluid through the second inflow and outflow lines such that the first inflow and outflow lines and the one of blood and non-blood compartments of a blood treatment device constitute a fixed volume fluid channel.

In additional embodiments thereof, the seventh embodiments include ones in which the pressure indicates a magnitude of a transmembrane transport between the blood and non-blood compartments. In additional embodiments thereof, the seventh embodiments include ones in which the pressure indicates a magnitude of a transmembrane transport between the blood and non-blood compartments and the calculating includes comparing the pressure to a predefined threshold pressure indicative of zero magnitude of a transmembrane transport between the blood and non-blood compartments. In additional embodiments thereof, the seventh embodiments include ones in which the pressure indicates a magnitude of a transmembrane transport between the blood and non-blood compartments. The calculating includes comparing the pressure to a predefined threshold pressure indicative of zero magnitude of a transmembrane transport between the blood and non-blood compartments. The system further includes determining the predefined threshold pressure by detecting a pressure of the at least one of the blood and non-blood compartments while blocking transport between the blood and non-blood compartments.

In additional embodiments thereof, the seventh embodiments include ones in which the pressure indicates a magnitude of a transmembrane transport between the blood and non-blood compartments. The calculating includes comparing the pressure to a predefined threshold pressure indicative of zero magnitude of a transmembrane transport between the blood and non-blood compartments. The system further includes determining the predefined threshold pressure by detecting a pressure of the at least one of the blood and non-blood compartments while blocking transport between the blood and non-blood compartments and while establishing flow through the second inflow and outflow lines at a predefined flow rate. In additional embodiments thereof, the seventh embodiments include ones in which the controller includes an embedded computer with a data store has instructions readable thereby to regulate, detect, and calculate and to store data responsive thereto. In additional embodiments thereof, the seventh embodiments include ones in which the control parameter includes a constant of proportionality that relates a command speed of a slave pump to a command speed of a master pump coinciding with identical flow rates therethrough. In additional embodiments thereof, the seventh embodiments include ones in which the controller is further programmed to, adjust the first outflow pump in response to a predefined ultrafiltration flow rate and the control parameter such that the first outflow pump generates a flow rate that is higher than that of the first inflow pump. In additional embodiments thereof, the seventh embodiments include ones in which the controller is further programmed to, in the treatment mode, continuously update a speed of the first outflow pump in response to a signal from the pressure. In additional embodiments thereof, the seventh embodiments include ones in which at least one pressure sensor is at least two, one of which indicates a pressure in the first inflow line and another of which indicates a pressure of the first outflow line. In additional embodiments thereof, the seventh embodiments include ones in which the pressure signal is an average of signals from the at least two.

According to eighth embodiments, the disclosed subject matter includes a method for controlling flow in a blood treatment fluid circuit. The method includes pumping fluid serially through first fluid lines connected to second fluid lines through a blood treatment device while blocking flow through the second fluid lines. The pumping includes, using a controller to control the speeds of pumping actuators, each of the pumping actuators determining a flow rate through a respective one of the first fluid lines. The first fluid lines are one of blood lines and treatment fluid lines and the second lines are the other of blood lines and treatment fluid lines. The method includes using the controller, detecting sensor data indicating a difference between the flow rates in the first fluid lines as well as speed data indicating a speed of at least one of the pumping actuators. The method includes using the controller, calculating one or more control parameters from the speed and sensor data, the one or more control parameters indicating the speed of the at least one of the pumping actuators for which the difference is below a predefined threshold. The method includes using the controller, regulating a net transfer of fluid through the first fluid line pair to, or from, the blood treatment device by regulates the speeds of the at least one of the pumping actuators responsively to the one or more control parameters.

In additional embodiments thereof, the eighth embodiments include ones in which the detecting and calculating are performed during a synchronization mode and the regulates is performed during a treatment mode. In additional embodiments thereof, the eighth embodiments include ones in which the calculating includes feedback controlling the at least one of the pumping actuators responsively to the sensor data to achieve a target magnitude indicated by the sensor data.

In additional embodiments thereof, the eighth embodiments include ones in which the sensor data is from a digitized pressure sensor signal, the pressure sensor indicating the pressure inside the blood treatment device.

In additional embodiments thereof, the eighth embodiments include ones in which the second fluid lines are blood lines of a hemodialysis fluid circuit. In additional embodiments thereof, the eighth embodiments include ones in which the blood treatment device is a dialyzer. In additional embodiments thereof, the eighth embodiments include ones in which the regulates includes a net transfer of fluid responsively to both the one or more control parameters and a predefined ultrafiltration rate, such that a net flow from the blood treatment device through the first fluid lines, equal to the predefined ultrafiltration rate, is established.

According to ninth embodiments, the disclosed subject matter includes a system for controlling flow in a blood treatment fluid circuit. A blood treatment machine is engaged with a fluid circuit has first and second fluid lines pairs connected to a blood treatment device. The blood treatment machine has a sensor that generates sensor data indicating a difference between the flow rates in the first fluid line pair. The blood treatment machine has a controller connected to the sensor, pumping actuators that pump fluid through the first and second line pairs and one line of the second fluid line pairs, and a flow regulator that controls flow through the other line of the second fluid line pairs. The controller pumps fluid serially through first fluid line pair connected to second fluid lines through a blood treatment device while blocking flow through the second fluid line pair. The first fluid lines are one of blood lines and treatment fluid lines and the second lines are the other of blood lines and treatment fluid lines. The controller detects the sensor data as well as speed data indicating a speed of at least one of the pumping actuators. The controller calculates one or more control parameters from the speed and the sensor data, the one or more control parameters indicating a speed of the at least one of the pumping actuators for which the difference is below a predefined threshold. The controller regulates a net transfer of fluid through the first fluid line pair to, or from, the blood treatment device by regulates the speeds of the at least one of the pumping actuators responsively to the one or more control parameters.

In additional embodiments thereof, the ninth embodiments include ones in which the detecting and calculating are performed during a synchronization mode and the regulates is performed during a treatment mode. In additional embodiments thereof, the ninth embodiments include ones in which the calculating includes feedback controlling the at least one of the pumping actuators responsively to the sensor data to achieve a target magnitude indicated by the sensor data. In additional embodiments thereof, the ninth embodiments include ones in which, wherein the sensor data is from a digitized pressure sensor signal, the pressure sensor indicating the pressure inside the blood treatment device. In additional embodiments thereof, the ninth embodiments include ones in which, the second fluid lines are blood lines of a hemodialysis fluid circuit. In additional embodiments thereof, the ninth embodiments include ones in which the blood treatment device is a dialyzer. In additional embodiments thereof, the ninth embodiments include ones in which the regulates includes a net transfer of fluid responsively to both the one or more control parameters and a predefined ultrafiltration rate, such that a net flow from the blood treatment device through the first fluid lines, equal to the predefined ultrafiltration rate, is established. In additional embodiments thereof, the ninth embodiments include ones in which the predefined threshold is a pressure in the blood treatment device when there is no flow in the first fluid line pair. In additional embodiments thereof, the ninth embodiments include ones in which the first fluid line pair is connected to a source and collector of dialysate.

According to tenth embodiments, the disclosed subject matter includes a method for controlling flow in a fluid circuit. The method applies to a blood treatment system that regulates the net ultrafiltration of a patient by balancing fluid withdrawn from a blood treatment device against fluid pump into the blood treatment device by controlling the relative volume displaced during a treatment by independently-regulated inflow and outflow pumps. The method includes using a controller, during a testing mode, detecting a difference between the flow rates of the inflow and outflow pumps continuously over a test interval while storing difference data representing the difference over time. The method includes using the controller, while detecting the difference and generating the difference data, controlling the rate of at least one of the inflow and outflow pumps to minimize the difference without establishing a minimum of the difference.

The method includes calculating, from the difference data and the rate of the at least one of the inflow and outflow pumps, a control parameter for regulates the at least one of the inflow and outflow pumps by extrapolating from a trend in the difference data an equilibrium rate of the at least one of the inflow and outflow pumps that corresponds to a minimum of the difference. The method includes performing a treatment includes controlling a net flow of fluid to or from a patient by controlling the inflow and outflow volumetric pumps responsively to the control parameter.

In additional embodiments thereof, the tenth embodiments include ones in which the blood treatment system is a dialysis system. In additional embodiments thereof, the tenth embodiments include ones in which the at least one of the inflow and outflow pumps pump fresh dialysate and spent dialysate, respectively. In additional embodiments thereof, the tenth embodiments include ones in which the calculating includes calculating a time-resolved moving average from the difference data and fitting the time-resolved moving average to a curve of flow difference vs. time.

According to eleventh embodiments, the disclosed subject matter includes a system for controlling flow in a fluid circuit. A blood treatment system that regulates the net ultrafiltration of a patient by balancing fluid withdrawn from a blood treatment device against fluid pump into the blood treatment device by controlling the relative volume displaced during a treatment by independently-regulated inflow and outflow pumps. A controller has a sensor adapted for indicating a difference between the flow rates of the inflow and outflow pumps. The controller, during a testing mode, detects a difference between the flow rates of the inflow and outflow pumps continuously over a test interval while storing difference data representing the difference over time. The controller, while detecting the difference and generating the difference data, controls the rate of at least one of the inflow and outflow pumps to minimize the difference without establishing a minimum of the difference. The controller calculates, from the difference data and the rate of the at least one of the inflow and outflow pumps, a control parameter for regulates the at least one of the inflow and outflow pumps by extrapolating from a trend in the difference data an equilibrium rate of the at least one of the inflow and outflow pumps that corresponds to a minimum of the difference. The controller performs a treatment includes controlling a net flow of fluid to or from a patient by controlling the inflow and outflow volumetric pumps responsively to the control parameter.

In additional embodiments thereof, the eleventh embodiments include ones in which the blood treatment system is a dialysis system. In additional embodiments thereof, the eleventh embodiments include ones in which the at least one of the inflow and outflow pumps pump fresh dialysate and spent dialysate, respectively. In additional embodiments thereof, the eleventh embodiments include ones in which the calculating includes calculating a time-resolved moving average from the difference data and fitting the time-resolved moving average to a curve of flow difference vs. time.

According to twelfth embodiments, the disclosed subject matter includes a blood treatment machine. Inflow and outflow pump actuators and at least one pressure sensor are connectable to a fluid circuit for measuring a pressure in a connected fluid circuit has a blood treatment device a controller, the pressure sensor indicating a difference between the flow rates of the inflow and outflow pump actuators. A controller regulates the inflow and outflow pump actuators to achieve a selected net ultrafiltration of a patient by balancing fluid withdrawn from a blood treatment device against fluid pump into the blood treatment device by independently regulates the speeds of the inflow and outflow pump actuators to achieve a relative volume displaced during a treatment by the inflow and outflow pump actuators. The controller, during a testing mode, detects a difference between the flow rates of the inflow and outflow pumps continuously over a test interval while storing difference data representing the difference over time. The controller, while detecting the difference and generating the difference data, controls the rate of at least one of the inflow and outflow pump actuators to minimize the difference without establishing a minimum of the difference. The controller calculates, from the difference data and the rate of the at least one of the inflow and outflow pump actuators, a control parameter for regulating the at least one of the inflow and outflow pump actuators by extrapolating from a trend in the difference data an equilibrium rate of the at least one of the inflow and outflow pump actuators that corresponds to a predetermined constant magnitude of a pressure indicated by the pressure sensor. The controller controls a net flow of fluid to or from a patient by controlling the inflow and outflow volumetric pumps responsively to the control parameter.

In additional embodiments thereof, the twelfth embodiments include ones in which the blood treatment machine is a dialysis cycler. In additional embodiments thereof, the twelfth embodiments include ones in which the calculating includes calculating a time-resolved moving average from the difference data and fitting the time-resolved moving average to a curve of flow difference vs. time.

According to thirteenth embodiments, the disclosed subject matter includes a method for controlling flow in a fluid circuit. The method includes, using the controller, establishing a blood flow in a blood treatment device with a membrane, at a predefined rate while preventing transmembrane flow across the membrane and detecting and storing a target pressure equal to a detected pressure within the blood treatment device. The method includes, during a synchronization mode, using the controller, feedback-controlling the speed of one or both of the inflow and outflow treatment fluid pumps responsively to a difference between the target pressure and a detected pressure inside the blood treatment device and calculating a control parameter from a resulting speed of the one or both of the inflow and outflow treatment fluid pumps, the control parameter indicating a relationship between the relative speeds of the inflow and outflow treatment fluid pumps under a condition of zero transmembrane flow. The method includes, during a treatment mode, using the controller, regulates the flow of treatment fluid across through the blood treatment device by regulates the relative speeds of the inflow and outflow treatment fluid pumps responsively to the control parameter.

In additional embodiments thereof, the thirteenth embodiments include ones in which the feedback-controlling includes controlling the inlet treatment fluid pump responsive to a difference between the target pressure and a detected pressure in the blood treatment device. In additional embodiments thereof, the thirteenth embodiments include ones in which the preventing includes halting the inflow and outflow treatment fluid pumps to prevent flow of treatment fluid through the blood treatment device. In additional embodiments thereof, the thirteenth embodiments include ones in which the inflow and outflow treatment fluid pumps include peristaltic pumps. In additional embodiments thereof, the thirteenth embodiments include ones in which, the detecting a target pressure includes receiving and averaging pressure signals from pressure sensors connected to detect the pressures of respective fluid lines between the inflow and outflow treatment fluid pumps and the blood treatment device. In additional embodiments thereof, the thirteenth embodiments include ones in which the detecting a target pressure includes receiving a pressure signal from a pressure sensor connected to detect the pressure of a fluid line between one of the inflow and outflow treatment fluid pumps and the blood treatment device.

In additional embodiments thereof, the thirteenth embodiments include ones in which the detected pressure is indicated by a pressure sensor indicating a pressure on a treatment fluid side of the membrane. In additional embodiments thereof, the thirteenth embodiments include ones in which the regulates the relative speeds of the inflow and outflow treatment fluid pumps responsively to the control parameter includes establishing a speed of the outflow treatment fluid pump that is greater than a speed corresponding to the control parameter and responsive to a predefined ultrafiltration rate. In additional embodiments thereof, the thirteenth embodiments include ones in which the regulates the relative speeds of the inflow and outflow treatment fluid pumps responsively to the control parameter includes establishing a speed of the outflow treatment fluid pump that is greater than a speed corresponding to the control parameter by an amount that is proportional to a predefined ultrafiltration rate.

In additional embodiments thereof, the thirteenth embodiments include ones that include adjusting a speed of the outflow treatment fluid pump responsively to an inlet pressure thereof in order to maintain a constant flow therethrough, the outflow treatment fluid pump are of a type whose volume rate of flow, for a given speed, is affected by inlet pressure.

According to fourteenth embodiments, the disclosed subject matter includes a device for controlling flow in a fluid circuit. First and second fluid circuits are coupled by an exchange device in which the first and second fluid circuits are separated by a membrane. T controller controls transmembrane flow between the first or second fluid circuits by regulates the rate of flow into the exchange device through the first fluid circuit by controlling the speed of a first pump relative to the rate out of the exchange device through the first fluid circuit by controlling the speed of a second pump. At a first time, the controller establishes a flow the second fluid circuit while preventing a transmembrane flow across the membrane and detecting and storing a target pressure equal to a detected pressure within the exchange device. At a second time, after the first time, the controller feedback-controls the speeds of one or both of the first and second pumps responsively to a difference between the target pressure and a detected pressure inside the exchange device and calculating a control parameter from a resulting speed of the one or both of the inflow and outflow treatment fluid pumps, the control parameter indicating a relationship between the relative speeds of the inflow and outflow treatment fluid pumps under a condition of zero transmembrane flow. The controller thereafter regulates controlling transmembrane flow between the first or second fluid circuits responsively to the control parameter.

In additional embodiments thereof, the fourteenth embodiments include ones in which the feedback-controlling includes controlling the inlet treatment fluid pump responsive to a difference between the target pressure and a detected pressure in exchange device. In additional embodiments thereof, the fourteenth embodiments include ones in which the preventing includes halting the first and second pumps to prevent flow of fluid in the first circuit. In additional embodiments thereof, the fourteenth embodiments include ones in which the first and second pumps include peristaltic pumps.

In additional embodiments thereof, the fourteenth embodiments include ones in which the feedback-controlling includes receiving and averaging pressure signals from pressure sensors connected to detect the pressures of respective fluid lines between the first and second pumps and the exchange device. In additional embodiments thereof, the fourteenth embodiments include ones in which the detecting a target pressure includes receiving a pressure signal from a pressure sensor connected to detect the pressure of a fluid line between one of the first and second pumps and the exchange device.

In additional embodiments thereof, the fourteenth embodiments include ones in which the detecting a target pressure includes receiving a pressure signal indicating a pressure on a treatment fluid side of the membrane. In additional embodiments thereof, the fourteenth embodiments include ones in which the regulates the relative speeds of the inflow and outflow treatment fluid pumps responsively to the control parameter includes establishing a speed of the outflow treatment fluid pump that is greater than a speed corresponding to the control parameter and responsive to a predefined ultrafiltration rate. In additional embodiments thereof, the fourteenth embodiments include ones in which the regulates the relative speeds of the inflow and outflow treatment fluid pumps responsively to the control parameter includes establishing a speed of the outflow treatment fluid pump that is greater than a speed corresponding to the control parameter by an amount that is proportional to a predefined ultrafiltration rate.

In additional embodiments thereof, the fourteenth embodiments include ones that include adjusting a speed of the second pump responsively to an inlet pressure thereof in order to maintain a constant flow therethrough, the second pump are of a type whose volume rate of flow, for a given speed, is affected by its inlet pressure.

According to fifteenth embodiments, the disclosed subject matter includes, a system for controlling flow in a fluid circuit. A treatment machine has a fluid circuit engaged with first, second, and third pumping actuators. The treatment machine has a controller connected to control the first, second, and third pumping actuators to perform a therapeutic treatment by regulates the flow fluid in a fluid circuit. The fluid circuit has a treatment device that interconnects first fluid lines via a first compartment thereof and second fluid lines via a second compartment thereof, the first and second pumping actuators controlling a net transport of fluid between the first and second compartments during a treatment mode, the pressure sensor indicating a pressure of the first and/or second compartment. The first, second, and third pumping actuators are controlled by the controller, at a first time during a synchronization mode, to block flow in the first fluid lines while pumping fluid through the second compartment at a predefined flow rate and to simultaneously store target pressure data responsive to a pressure signal from the pressure sensor. The controller determines a pump control parameter responsively by feedback-controlling the first and second pumping actuators toward a control goal based on the target pressure data and estimating a speed of one or both of the first and second pumping actuators that establishes the control goal and an identical flow rate of the first and second pumps indicated by a constant pressure signal from the pressure sensor. The first and second pumping actuators are controlled by the controller, at a second time during a treatment mode to pump fluid through the second compartment at the predefined flow rate while simultaneously controlling flow in the first fluid lines responsively to the control parameter.

In additional embodiments thereof, the fifteenth embodiments include ones in which the treatment device is a hemodialyzer and the first and second pumping actuators are engaged with dialysate and waste pumps connected to the hemodialyzer. In additional embodiments thereof, the fifteenth embodiments include ones in which first compartment is a dialysate compartment of a dialyzer. In additional embodiments thereof, the fifteenth embodiments include ones in which second compartment is a blood compartment of a dialyzer. In additional embodiments thereof, the fifteenth embodiments include ones in which the determining includes extrapolating a trend of pressure versus time and estimating therefrom a relationship between the speed of the first pump and the speed of the second pump that provide the same flow rates through the first and second pumps.

According to sixteenth embodiments, the disclosed subject matter includes a system for controlling flow in a fluid circuit. A machine has a fluid circuit engaged with first, second, and third pumping actuators. The treatment machine has a controller connected to control the first, second, and third pumping actuators to regulate a flow fluid in a fluid circuit. The fluid circuit has a fluid exchange device that interconnects first fluid lines via a first compartment thereof and second fluid lines via a second compartment thereof, the first and second pumping actuators controlling a net transport of fluid between the first and second compartments during production mode, the pressure sensor indicating a pressure of the first and/or second compartment. The first, second, and third pumping actuators are controlled by the controller, at a first time during a synchronization mode, to block flow in the first fluid lines while pumping fluid through the second compartment at a predefined flow rate and to simultaneously store target pressure data responsive to a pressure signal from the pressure sensor. The controller determines a pump control parameter responsively by feedback-controlling the first and second pumping actuators toward a control goal based on the target pressure data and estimating a speed of one or both of the first and second pumping actuators that establishes the control goal and an identical flow rate of the first and second pumps indicated by a constant pressure signal from the pressure sensor. The first and second pumping actuators are controlled by the controller, at a second time during the production mode, to pump fluid through the second compartment at the predefined flow rate while simultaneously controlling flow in the first fluid lines responsively to the pressure data.

In additional embodiments thereof, the sixteenth embodiments include ones in which the determining includes extrapolating a trend of pressure versus time and estimating therefrom a relationship between the speed of the first pump and the speed of the second pump that provide the same flow rates through the first and second pumps.

According to seventeenth embodiments, the disclosed subject matter includes a method for controlling flow in a fluid circuit. The method includes regulating the flow of fluid across a blood treatment device membrane contacting a blood flow path responsively to a pressure signal responsive to pressure in the blood treatment device. The regulating includes controlling respective speeds of inflow and outflow pumps, the inflow pump pumping treatment fluid into the blood treatment device and the outflow pump pumping treatment fluid out of the blood treatment device responsively to prediction data correlating pressures on a blood and/or treatment fluid side of the membrane with flow rates on a blood side of the membrane. The method further includes, prior to the regulating, detecting pressure signals indicating pressure on the blood and/or treatment fluid side of the membrane for each of multiple flow rates of fluid on the blood side of the membrane for condition of zero flow across the membrane and storing the prediction data responsively to the pressure signals and flow rates.

In additional embodiments thereof, the seventeenth embodiments include ones that include adjusting the outflow pump to draw fluid through the membrane at a predefined ultrafiltration rate. In additional embodiments thereof, the seventeenth embodiments includes ones in which the regulating includes synchronizing the flow rates inflow and outflow pumps. In additional embodiments thereof, the seventeenth embodiments includes ones in which the regulating includes feedback controlling the flow rates inflow and outflow pumps toward a target pressure to determine rates thereof that produce equal flow.

In additional embodiments thereof, the seventeenth embodiments that include advancing a rate of the outflow pump responsively to a predetermined ultrafiltration rate.

According to eighteenth embodiments, the disclosed subject matter includes, a system for controlling flow in a fluid circuit. A treatment machine has a fluid circuit engaged with first, second, and third pumping actuators. The treatment machine has a controller connected to control the first, second, and third pumping actuators to perform a therapeutic treatment by regulates the flow fluid in the fluid circuit. The fluid circuit has a treatment device that interconnects first fluid lines via a first compartment thereof and second fluid lines via a second compartment thereof, the first and second pumping actuators controlling a net transport of fluid between the first and second compartments during a treatment mode, the pressure sensor indicating a pressure of the first and/or second compartment. The first and second pumping actuators are controlled by the controller, at a first time during a synchronization mode, to block flow in the first fluid lines while pumping fluid through the second compartment at multiple predefined flow rates and to simultaneously store prediction data responsive to a pressure signal from the pressure sensor at each of the flow rates. The first and second pumping actuators are controlled by the controller, at a second time during a treatment mode to pump fluid through the second compartment at a current flow rate while simultaneously controlling flow in the first fluid lines responsively to the prediction data. In additional embodiments thereof, the eighteenth embodiments includes ones in which the controller, at the second time, adjusts the outflow pump to draw fluid through the membrane at a predefined ultrafiltration rate. In additional embodiments thereof, the eighteenth embodiments includes ones in which the controller, after the first time, synchronizes the flow rates inflow and outflow pumps by monitoring the pressure signal from the pressure sensor to achieve a steady pressure indicated by the pressure sensor at the first time, for each of the flow rates. In additional embodiments thereof, the eighteenth embodiments includes ones in which the controller, at the second time, advances a rate of the outflow pump responsively to a predetermined ultrafiltration rate.

According to nineteenth embodiments, the disclosed subject matter includes a method for controlling flow in a fluid circuit. The method includes treating a patient body fluid by pumping a treatment fluid from a source, through a treatment device, to a sink while pumping the body fluid of a patient through the treatment device. The method includes regulating a net transfer of fluid to or from the body fluid by controlling the pumping treatment fluid at respective rates into and out of the treatment device. The method includes, at a time before or during the treating, isolating the source and sink from the treatment device and establishing a closed-loop flow of treatment fluid between an accumulator and the treatment device while detecting a net transfer of fluid through the treatment device and using a result of the detecting to calculate an error in the controlling of the respective rates into and out of the treatment device. The method includes storing data indicating the result of the detecting and subsequently further regulates a net transfer of fluid to or from the body fluid by controlling the pumping treatment fluid at respective rates into and out of the treatment device responsively to the data.

In additional embodiments thereof, the nineteenth embodiments include ones that further include connecting the accumulator with a priming fluid therein to the treatment device. In additional embodiments thereof, the nineteenth embodiments includes ones in which the detecting a net transfer of fluid through the treatment device includes detecting a change in a weight or volume of the accumulator. In additional embodiments thereof, the nineteenth embodiments may include reversing a pump to reverse a flow through the accumulator and collecting air therein. In additional embodiments thereof, the nineteenth embodiments includes ones in which the sink is a collection container or a drain. In additional embodiments thereof, the nineteenth embodiments includes ones in which the body fluid is blood. In additional embodiments thereof, the nineteenth embodiments includes ones in which the treatment fluid is dialysate and the treatment device is a dialyzer. In additional embodiments thereof, the nineteenth embodiments includes ones in which the regulating includes controlling the relative speeds of pumps pumping fluid into and out of the treatment device.

According to twentieth embodiments, the disclosed subject matter includes a system for controlling flow in a fluid circuit. A treatment machine has a fluid circuit engaged with a treatment fluid inlet pump actuator, treatment machine fluid outlet pump actuator, and a blood pump actuator. The treatment machine has a controller connected to control the pumping actuators to perform a therapeutic treatment by regulates the flow fluid in the fluid circuit. The fluid circuit has a treatment device that interconnects treatment fluid lines via a non-blood compartment thereof and blood lines via a blood compartment thereof, the treatment fluid inlet pump actuator and treatment fluid outlet pump actuator controlling a net transport of fluid between the non-blood and blood compartments during a treatment mode of a controller. The treatment fluid lines are selectively connectable by the controller to form a closed loop between an accumulator of the fluid circuit through the non-blood compartment. The treatment fluid lines are selectively connectable, by the controller, between a treatment fluid source and sink and the non-blood compartment to form a circuit that bypasses the accumulator of the fluid circuit. The treatment fluid inlet pump actuator and treatment fluid outlet pump actuator are controlled by the controller, at a first time during a synchronization mode, to pump fluid through the closed loop and to detect a net transfer of fluid through the treatment device and responsively thereto, the controller storing data indicative of the net transfer. The controller calculates a flow regulation parameter from the data. The treatment fluid inlet pump actuator and treatment fluid outlet pump actuator are controlled by the controller responsively to the flow regulation parameter, at a second time during a treatment mode, to pump fluid from the source, through the non-blood compartment, to the sink to perform a treatment.

In additional embodiments thereof, the twentieth embodiments include ones in which the accumulator is a priming fluid bag connected to the treatment fluid lines.

In additional embodiments thereof, the twentieth embodiments include ones in which the net transfer of fluid through the treatment device is detected by detecting a change in a weight or volume of the accumulator. In additional embodiments thereof, the twentieth embodiments include ones in which the sink is a collection container or a drain. In additional embodiments thereof, the twentieth embodiments include ones in which the body fluid is blood. In additional embodiments thereof, the twentieth embodiments include ones in which the treatment fluid is dialysate and the treatment device is a dialyzer.

According to twenty-first embodiments, the disclosed subject matter includes a method for controlling flow in a fluid circuit. The method includes providing a blood treatment system has a blood treatment device with a membrane that separates blood and non-blood compartments of the blood treatment device. The method includes pumping a blood-normal fluid through the non-blood compartment to prime it and pumping a priming fluid through the blood compartment. The method further includes pumping blood through the blood compartment while halting a flow of blood-normal fluid and simultaneously sampling signals from pressure sensors indicating a difference between the pressure of the non-blood compartment and the blood compartment. The method further includes using a controller, storing pressure difference data responsive to the sampling and regulates a net transfer of fluid across the membrane during a treatment cycle responsively to the pressure difference data.

In additional embodiments thereof, the twenty-first embodiments include ones in which the regulates includes controlling speeds of treatment fluid pumps that pump fluid into and out of the blood treatment device. In additional embodiments thereof, the twenty-first embodiments include ones in which the regulating includes controlling speeds of treatment fluid pumps that pump fluid into and out of the blood treatment device, the blood treatment device includes a dialyzer.

In additional embodiments thereof, the twenty-first embodiments include ones in which the regulating a net transfer of fluid across the membrane during a treatment cycle includes repeating the pumping blood through the blood compartment while halting a flow of blood-normal fluid multiple times during a treatment and detecting therefrom a change in the pressure difference data between successive ones of the multiple times. In additional embodiments thereof, the twenty-first embodiments include ones in which the regulating a net transfer of fluid across the membrane during a treatment cycle further includes, between the multiple times, reducing or halting the net transfer of fluid across the membrane and determining a treatment time or an ultrafiltration rate responsively to the pressure difference data between successive ones of the multiple times, whereby a fluid rebound caused by fluid shifting in a patient to the patient's blood compartment is indicated by the change in pressure difference data between the successive ones is used to control the rate and/or extent of fluid withdrawal from a patient.

According to twenty-second embodiments, the disclosed subject matter includes a system for controlling flow in a fluid circuit. A blood treatment machine is connected to a fluid circuit with a blood treatment device with a membrane that separates blood and non-blood compartments of the blood treatment device. The blood treatment machine has a programmable controller connected to control a treatment fluid inflow pump, a treatment fluid outflow pump, a blood pump, and to receive pressure signals from one or more pressure sensors indicating the difference between the pressures of the blood and non-blood compartments. An inflow pump is connected to a source of blood-normal fluid, the controller are programmed to control the inflow and outflow treatment fluid pumps to pump fluid through the non-blood compartment to prime it during a non-treatment operating mode. A blood pump is connected to the blood compartment, the controller are programmed to pump a priming fluid through the blood compartment during the non-treatment operating mode. The controller is programmed to pump blood through the blood compartment while halting the inflow and outflow treatment fluid pumps and simultaneously sample signals from the one or more pressure sensors. The controller stores pressure difference data responsive to the sampling and controlling the inflow and outflow treatment fluid pumps responsively to the pressure difference data to regulate a net transfer of fluid across the membrane during a treatment cycle. In additional embodiments thereof, the twenty-second embodiments include ones in which the blood treatment device includes a dialyzer. In additional embodiments thereof, the twenty-second embodiments include ones in which the controller regulates a net transfer of fluid across the membrane during a treatment cycle by repeating the pumping blood through the blood compartment while halting a flow of blood-normal fluid multiple times during a treatment and detecting therefrom a change in the pressure difference data between successive ones of the multiple times. In additional embodiments thereof, the twenty-second embodiments include ones in which the controller regulates a net transfer of fluid across the membrane during a treatment cycle by repeating the pumping blood through the blood compartment while halting a flow of blood-normal fluid multiple times during a treatment and detecting therefrom a change in the pressure difference data between successive ones of the multiple times and, between the multiple times, reducing or halting the net transfer of fluid across the membrane and determining a treatment time or an ultrafiltration rate responsively to the pressure difference data between successive ones of the multiple times, whereby a fluid rebound caused by fluid shifting in a patient to the patient's blood compartment is indicated by the change in pressure difference data between the successive ones is used to control the rate and/or extent of fluid withdrawal from a patient.

According to twenty-third embodiments, the disclosed subject matter includes a method for controlling flow in a fluid circuit. The method includes using a controller of a treatment machine that controls flow of fluids and blood in a fluid circuit, measuring oncotic pressure of blood during a treatment by halting a flow of a blood-normal treatment fluid in a blood treatment device separating flowing blood from the treatment fluid while measuring a pressure difference between the treatment fluid and blood compartments of the blood treatment device. The method includes repeating the measuring multiple times during a treatment to obtain multiple oncotic pressure samples. The method includes comparing a trend in the oncotic pressure samples to a predefined trend and determining a treatment parameter therefrom. In additional embodiments thereof, the twenty-third embodiments include ones in which the treatment parameter includes a further duration of an on-going treatment. In additional embodiments thereof, the twenty-third embodiments include ones in which the treatment parameter includes an ultrafiltration rate during an on-going treatment.

In additional embodiments thereof, the twenty-third embodiments include ones in which the controller reduces or increases a rate of ultrafiltration of the blood treatment device responsively to the trend.

According to twenty-fourth embodiments, the disclosed subject matter includes a system for controlling flow in a fluid circuit. A blood treatment machine has a controller that controls flow of fluids and blood in a fluid circuit, the controller are programmed to selectively place the fluid circuit in a condition for measuring oncotic pressure of blood during a treatment by halting a flow of a blood-normal treatment fluid in a blood treatment device separating flowing blood from the treatment fluid while measuring a pressure difference between the treatment fluid and blood compartments of the blood treatment device. The controller repeats the measuring multiple times during a treatment to obtain multiple oncotic pressure samples. The controller compares a trend in the oncotic pressure samples to a predefined trend and determining a treatment parameter of a treatment delivered by the blood treatment machine responsively to the trend or a value of the oncotic pressure.

In additional embodiments thereof, the twenty-fourth embodiments include ones in which the treatment parameter includes a further duration of an on-going treatment. In additional embodiments thereof, the twenty-fourth embodiments include ones in which the treatment parameter includes an ultrafiltration rate during an on-going treatment.

In additional embodiments thereof, the twenty-fourth embodiments include ones in which the controller reduces or increases a rate of ultrafiltration of the blood treatment device responsively to the trend.

According to twenty-fifth embodiments, the disclosed subject matter includes method for controlling flow in a fluid circuit. The method includes providing a blood treatment system has a blood treatment device with a membrane that separates blood and non-blood compartments of the blood treatment device. The method includes pumping a blood-normal fluid through the non-blood compartment to prime it. The method includes pumping a priming fluid through the blood compartment. The method includes pumping blood through the blood compartment while halting a flow of blood-normal fluid and simultaneously sampling signals from pressure sensors indicating a difference between the pressure of the non-blood compartment and the blood compartment. The method includes using a controller, storing property pressure difference data responsive to the sampling and controlling the inflow and outflow treatment fluid pumps responsively to the pressure difference data to calculate a status of a treatment, a blood property, or a fluid level of a patient are treated and outputting data responsive to the status, property, or level includes one or more of: an amount of fluid to be removed from or transferred to or from the patient or an estimated remaining time of treatment.

In additional embodiments thereof, the twenty-fifth embodiments include ones in which the controller outputs the responsive data on a display or stores it in a treatment log.

According to twenty-sixth embodiments, the disclosed subject matter includes a system for controlling flow in a fluid circuit. A blood treatment machine is connected to a fluid circuit with a blood treatment device with a membrane that separates blood and non-blood compartments of the blood treatment device. The blood treatment machine has a programmable controller connected to control a treatment fluid inflow pump, a treatment fluid outflow pump, a blood pump, and to receive pressure signals from one or more pressure sensors indicating the difference between the pressures of the blood and non-blood compartments. An inflow pump is connected to a source of blood-normal fluid, the controller are programmed to control the inflow and outflow treatment fluid pumps to pump fluid through the non-blood compartment to prime it during a non-treatment operating mode. A blood pump is connected to the blood compartment, the controller are programmed to pump a priming fluid through the blood compartment during the non-treatment operating mode. The controller is programmed to pump blood through the blood compartment while halting the inflow and outflow treatment fluid pumps and simultaneously sampling signals from the one or more pressure sensors. The controller stores property pressure difference data responsive to the sampling and controlling the inflow and outflow treatment fluid pumps responsively to the pressure difference data to calculate a status of a treatment, a blood property, or a fluid level of a patient are treated and outputting data responsive to the status, property, or level includes one or more of: an amount of fluid to be removed from or transferred to the from the patient, an estimated remaining time of treatment, a plasma protein concentration, or a hematocrit of the patient.

In additional embodiments thereof, the twenty-sixth embodiments include ones in which the controller outputs the responsive data on a display or stores it in a treatment log.

According to twenty-seventh embodiments, the disclosed subject matter includes a method for controlling flow in a fluid circuit. The method includes providing a treatment machine with a controller, pumps, and at least one pressure sensor, the pumps are engaged with inflow and outflow lines to regulate flow therethrough responsively to the controller. The method includes connecting the inflow and outflow fluid lines to flow fluid to and from a patient, respectively, or to flow fluid to and from a treatment device connected to a patient, respectively. The method includes, at treatment times, using the controller, regulating a net transport of fluid to the patient or the treatment device by controlling the relative flow rates in the inflow and outflow lines. The method includes, at at least one synchronization time, using the controller, temporarily establishing a direct connection between the inflow and outflow lines, bypassing the patient or the treatment device connected to a patient and simultaneously using a predefined pressure sensor, detecting a difference between the flow rates in the inflow and outflow lines. The method includes, using the detected pressure in the detecting to regulate the net transport at one or more of the treatment times. The method includes, at a configuration time, after connecting the inflow and outflow lines, using the controller, detecting if there is a connection error using the pressure sensor and outputting a signal indicating a result of the detecting on a user interface.

According to further embodiments, the disclosed subject matter includes a system for controlling flow in a fluid circuit. A treatment machine has a programmable controller, pumps, and at least one pressure sensor, the pumps are engaged with inflow and outflow lines to regulate flow therethrough responsively to the controller. The inflow and outflow fluid lines are connectable to a patient access or a blood treatment device and arranged to flow fluid to and from a patient, respectively, or to flow fluid to and from the treatment device connected to a patient, respectively. The controller is programmed to, at treatment times, regulate a net transport of fluid to the patient or the treatment device by controlling the relative flow rates in the inflow and outflow lines. The controller is programmed to, at at least one synchronization time, temporarily establish a direct connection between the inflow and outflow lines such that the patient or the treatment device connected to a patient is bypassed. At the at least at synchronization time, the controller samples and storing pressure signals from a predefined pressure sensor to detect a difference between the flow rates in the inflow and outflow lines and calculate a flow control parameter from the stored samples. The controller thereafter uses the flow control parameter to regulate the net transport at one or more of the treatment times. The controller is further programmed to receive a set-up signal indicating that the patient access or the treatment device has been connected to the inflow and outflow lines and in response thereto, detect whether there is a connection error using the predefined pressure sensor and to output a signal responsive to the detection.

According to further embodiments, the disclosed subject matter includes a method for controlling flow in a fluid circuit. The method includes using a controller, regulates the flow of fluid across a blood treatment device membrane contacting a blood flow path responsively to a pressure signal indicating pressure in the blood treatment device. The regulating includes controlling speeds of inflow and outflow pumps, the inflow pump pumping treatment fluid into the blood treatment device and the outflow pump pumping treatment fluid out of the blood treatment device responsively to a target pressure on a blood and/or treatment fluid side of the membrane. The method includes using the controller, at a synchronization time prior to the regulates, obtaining and storing the target pressure in a data store of the controller. The target pressure are calculated from a detected pressure on the blood and/or treatment fluid side of the membrane at a time when the inflow and outflow pumps are halted. The controller, at the synchronization time, halts the inflow and outflow pumps.

According to further embodiments, the disclosed subject matter includes a system for controlling flow in a fluid circuit. A treatment machine has a fluid circuit engaged with first, second, and third pumping actuators. The treatment machine has a controller connected to control the first, second, and third pumping actuators to perform a therapeutic treatment by regulates the flow fluid in the fluid circuit. The fluid circuit has a treatment device that interconnects first fluid lines via a first compartment thereof and second fluid lines via a second compartment thereof, the first and second pumping actuators controlling a net transport of fluid between the first and second compartments during a treatment mode, the pressure sensor indicating a pressure of the first and/or second compartment. The first and second pumping actuators are controlled by the controller, at a first time during a synchronization mode, to block flow in the first fluid lines while pumping fluid through the second compartment at a predefined flow rate and to simultaneously store pressure data responsive to a pressure signal from the pressure sensor. The first and second pumping actuators are controlled by the controller, at a second time during a treatment mode to pump fluid through the second compartment at the predefined flow rate while simultaneously controlling flow in the first fluid lines responsively to the pressure data.

According to further embodiments, the disclosed subject matter includes a method for controlling flow in a fluid circuit. The method applies to a hemofiltration machine with a controller that controls a net ultrafiltration by independently regulates the speed of a waste pump that draws fluid from a hemofilter and the speed of a replacement fluid pump that pumps replacement fluid into a patient blood line, using the controller to control the pumps to implement synchronization and treatment modes. According to the method, in a synchronization mode, the controller detecting a target pressure at an inlet of the waste pump while flowing blood through the hemofilter and while blocking flow through the replacement fluid and waste pumps. Subsequently, in the synchronization mode, the controller connects the replacement fluid pump and the waste pump directly in series and, while flowing replacement fluid between them and controlling the waste pump speed to establish a predetermined hemofiltration rate, controlling the replacement fluid pump speed to determine a synchronized replacement fluid pump speed that maintains the waste pump inlet pressure at the target pressure. Subsequently, in a treatment mode, the controller connects the replacement fluid pump to pump replacement fluid into a blood circuit at the synchronized replacement pump speed.

According to further embodiments, the disclosed subject matter includes a system for controlling flow in a fluid circuit. A hemofiltration machine with fluid circuit has blood and non-blood portions, a controller that controls waste and treatment fluid pumps connected to a hemofilter, a pressure sensor at an inlet of the waste pump, and flow controllers permitting selective interconnection of the blood and non-blood portions. The waste pump draws fluid from a hemofilter and the replacement fluid pump pumping replacement fluid into the blood portion. The controller controls a net ultrafiltration, during a treatment mode, by independently regulates the speeds of the waste and replacement fluid pumps. The controller is programmed to establish a synchronization mode in which the controller detects a target pressure from the pressure sensor while flowing blood through the hemofilter and while halting flow through the replacement fluid and waste pumps. Subsequently, in the synchronization mode, the controller connects the replacement fluid pump and the waste pump directly in series through the non-blood portion, flowing replacement fluid between the pumps and controlling the waste pump speed establish a predetermined hemofiltration rate, controlling the replacement fluid pump speed to determine a synchronized replacement pump speed that maintains the waste pump inlet pressure at the target pressure. Subsequently, in the treatment mode, the controller connects the replacement fluid pump to pump replacement fluid into the blood portion at the synchronized replacement pump speed.

According to twenty-eighth embodiments, the disclosed subject matter includes a method for controlling flow in a fluid circuit. The method applies to a hemodiafiltration machine with a controller that controls a net ultrafiltration by independently regulates the speed of a waste pump that draws fluid from a hemodiafilter, the speed of a dialysate pump that pumps dialysate into the hemodiafilter, and the speed of a replacement fluid pump that pumps replacement fluid into a patient blood line, using the controller to control the pumps to implement first and second synchronization and treatment modes. In the first synchronization mode, the controller detects a first target pressure at an inlet of the waste pump and a second target pressure equal to the average of pressure at the outlet of the dialysate pump and the pressure at the inlet of the waste pump both while flowing blood through the hemodiafilter and while blocking flow through the replacement fluid and waste pumps. Subsequently, in the first synchronization mode, the controller pumps dialysate through the hemodiafilter using the dialysate and waste pumps and controlling the waste pump speed to establish a predetermined dialysate flow rate, controlling the dialysate pump speed to determine a synchronized dialysate pump speed that maintains the average of the outlet of the dialysate pump and the pressure at the inlet of the waste pump at the second target pressure. Subsequently, in the second synchronization mode, the controller connects the replacement fluid pump and the waste pump directly in series and, while flowing replacement fluid between them and controlling the waste pump speed establish a predetermined hemofiltration rate, controlling the replacement fluid pump speed to determine a synchronized replacement fluid pump speed that maintains the waste pump inlet pressure at the first target pressure. Subsequently, in a treatment mode, the controller connects the replacement fluid pump to pump replacement fluid into the blood portion at the synchronized replacement fluid pump speed, connect the dialysate pump to pump dialysate into the hemodiafilter at the synchronized dialysate pump speed, and to connect the waste pump to draw waste fluid from the hemodiafilter at a rate responsive to the predetermined dialysate flow rate and the predetermined hemofiltration rate.

In additional embodiments thereof, the twenty-eighth embodiments include ones in which in the treatment mode, the waste pump is controlled to draw waste fluid from the hemodiafilter at a rate equal to the sum of the predetermined dialysate flow rate and the predetermined hemofiltration rate.

According to twenty-ninth embodiments, the disclosed subject matter includes a system for controlling flow in a fluid circuit. A hemofiltration machine has fluid circuit has blood and non-blood portions, a controller waste, dialysate, and treatment fluid pumps connected to a hemodiafilter, a pressure sensor at an inlet of the waste pump, and flow controllers permitting selective interconnection of the blood and non-blood portions. The controller controls a net ultrafiltration, during a treatment mode, by independently regulates the speed of the waste pump that draws fluid from a hemodiafilter, the speed of a replacement fluid pump that pumps replacement fluid into the blood portion, and the speed of the dialysate pump that pumps dialysate into the hemodiafilter. The controller controls the pumps to implement first and second synchronization modes and a treatment mode. In the first synchronization mode, the controller detects a target pressure at an inlet of the waste pump while flowing blood through the hemodiafilter and while blocking flow through the replacement fluid and waste pumps. Subsequently, in the first synchronization mode, the controller pumps dialysate through the hemodiafilter using the dialysate and waste pumps and controlling the waste pump speed to establish a predetermined dialysate flow rate, controlling the dialysate pump speed to determine a synchronized dialysate pump speed that maintains the waste pump inlet pressure at the target pressure. Subsequently, in the second synchronization mode, the controller connects the replacement fluid pump and the waste pump directly in series and, while flowing replacement fluid between them and controlling the waste pump speed establish a predetermined hemofiltration rate, controlling the replacement fluid pump speed to determine a synchronized replacement fluid pump speed that maintains the waste pump inlet pressure at the target pressure. Subsequently, in a treatment mode, the controller connects the replacement fluid pump to pump replacement fluid into the blood portion at the synchronized replacement fluid pump speed, connect the dialysate pump to pump dialysate into the hemodiafilter at the synchronized dialysate pump speed, and to connect the waste pump to draw waste fluid from the hemodiafilter at a rate responsive to the predetermined dialysate flow rate and the predetermined hemofiltration rate. In additional embodiments thereof, the twenty-ninth embodiments include ones in which wherein, in the treatment mode, the waste pump is controlled to draw waste fluid from the hemodiafilter at a rate equal to the sum of the predetermined dialysate flow rate and the predetermined hemofiltration rate.

According to thirtieth embodiments, the disclosed subject matter includes a method for controlling flow in a fluid circuit. The method applies to a treatment machine that controls the total volume of fluid flowing into or from a patient against the total volume of fluid drawn from the patient by regulates the relative speeds of peristaltic pumps that flow fluid in a fluid circuit connected to the patient. The method includes implementing a priming mode in which priming fluid is pumped through the fluid circuit the priming mode includes pumping fluid through the fluid pumps for a break-in interval of at least five minutes before establishing a treatment mode in which the peristaltic pumps are used to control a net flow of fluid into or from the patient. In additional embodiments thereof, the thirtieth embodiments include ones in which the treatment machine is a hemodialysis machine and the pumps regulate the flow of dialysate into and out of a dialyzer. In additional embodiments thereof, the thirtieth embodiments include ones that further include, after the break-in interval, performing a flow calibration procedure in which the flow of one of the peristaltic pumps is calibrated against a standard or another of the peristaltic pumps. In additional embodiments thereof, the thirtieth embodiments include ones in which the calibration procedure generates a control parameter that is used by the controller to regulate the peristaltic pumps during the treatment mode.

It will be appreciated that the modules, controllers, processes, systems, and sections described above can be implemented in hardware, hardware programmed by software, software instruction stored on a non-transitory computer readable medium or a combination of the above. For example, a method for balancing fluid flow can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of controllers and especially digital controllers and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, flow balancing devices, methods and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method for controlling fluid flow in a fluid circuit, comprising:
providing a blood treatment device having a blood compartment and a non-blood compartment separated from each other by a membrane;
connecting a first inflow line and a first outflow line to one of the blood and the non-blood compartments of the blood treatment device;
connecting a second inflow line and a second outflow line to the other of the blood and the non-blood compartments of the blood treatment device;
using a controller, regulating a speed of a first inflow pump fluidly connected to the first inflow line, to establish a flow into said one of the blood and the non-blood compartments of the blood treatment device;
using the controller, regulating a speed of a first outflow pump fluidly connected to the first outflow line to establish a flow out of said one of the blood and the non-blood compartments of the blood treatment device;
detecting a pressure of at least one of the blood and the non-blood compartments, said pressure indicating a magnitude of a difference between rates of the flows into and out of said one of the blood and the non-blood compartments;
during said detecting, blocking a flow of fluid through the second inflow and outflow lines such that the first inflow and outflow lines and said one of the blood and the non-blood compartments of the blood treatment device constitute a fixed volume fluid channel;
calculating a flow control parameter responsively to said pressure; and
thereafter regulating a net transfer of fluid between the blood and the non-blood compartments responsively to the control parameter.

2. The method of claim 1, further comprising, during said detecting, flowing fluid through the second inflow and outflow lines.

3. The method of claim 1, wherein the pressure indicates a magnitude of a transmembrane transport between the blood and the non-blood compartments.

4. The method of claim 1, wherein the pressure indicates a magnitude of a transmembrane transport between the blood and the non-blood compartments and the calculating includes comparing the pressure to a predefined threshold pressure indicative of zero magnitude of the transmembrane transport between the blood and the non-blood compartments.

5. The method of claim 1, wherein the pressure indicates a magnitude of a transmembrane transport between the blood and the non-blood compartments;
the calculating includes comparing the pressure to a predefined threshold pressure indicative of zero magnitude of the transmembrane transport between the blood and the non-blood compartments; and
the method further includes determining the predefined threshold pressure by detecting a pressure of the at least one of the blood and the non-blood compartments while blocking transport between the blood and the non-blood compartments.

6. The method of claim 1, wherein the pressure indicates a magnitude of a transmembrane transport between the blood and the non-blood compartments;
the calculating includes comparing the pressure to a predefined threshold pressure indicative of zero magnitude of the transmembrane transport between the blood and the non-blood compartments; and
the method further includes determining the predefined threshold pressure by detecting a pressure of the at least one of the blood and the non-blood compartments while blocking transport between the blood and the non-blood compartments and while establishing flow through the second inflow and outflow lines at a predefined flow rate.

7. The method of claim 1, wherein the controller includes an embedded computer with a data store having instructions readable thereby to regulate, detect, and calculate and to store data responsive thereto.

8. The method of claim 1, wherein the control parameter includes a constant of proportionality that relates a command speed of a slave pump to a command speed of a master pump coinciding with identical flow rates therethrough.

9. The method of claim 1, wherein the controller adjusts the first outflow pump in response to a predefined ultrafiltration flow rate and said control parameter such that the first outflow pump generates a flow rate that is higher than that of the first inflow pump.

10. The method of claim 1, wherein the controller continuously updates a speed of the first outflow pump in response to a signal from the detected pressure.

11. The method of claim 1, wherein the detected pressure of at least one of the blood and the non-blood compartments is indicated by at least one of a pressure in the first inflow line and a pressure in the first outflow line.

12. The method of claim 11, wherein the pressure of at least one of the blood and the non-blood compartments is an average of the pressure in the first inflow line and the pressure in the first outflow line.

13. The method according to claim 1, wherein the detecting the pressure of at least one of the blood and the non-blood compartments is detecting the pressure of the blood compartment.

14. A method for controlling flow in a blood treatment fluid circuit, the method comprising:
pumping fluid serially through first fluid lines connected to second fluid lines through a blood treatment device while blocking flow through the second fluid lines;
the pumping including, using a controller to control speeds of pumping actuators, each of the pumping actuators determining a flow rate through a respective one of the first fluid lines;
the first fluid lines being one of blood lines and treatment fluid lines and the second lines being the other of blood lines and treatment fluid lines;
using the controller, detecting sensor data indicating a difference between said flow rates in the first fluid lines as well as speed data indicating a speed of at least one of the pumping actuators;
using the controller, calculating one or more control parameters from said speed and sensor data, the one or more control parameters indicating said speed of said at least one of the pumping actuators for which said difference is below a predefined threshold; and
using the controller, regulating a net transfer of fluid through a pair of the first fluid lines to, or from, the blood treatment device by regulating the speeds of said at least one of the pumping actuators responsively to said one or more control parameters.

15. The method of claim 14, wherein the detecting and calculating are performed during a synchronization mode and said regulating is performed during a treatment mode.

16. The method of claim 14, wherein the calculating includes feedback controlling the at least one of the pumping actuators responsively to the sensor data to achieve a target magnitude indicated by said sensor data.

17. The method of claim 14, wherein said sensor data is from a digitized pressure sensor signal, the pressure sensor indicating the pressure inside the blood treatment device.

18. The method of claim 14, wherein said second fluid lines are blood lines of a hemodialysis fluid circuit.

19. The method of claim 18, wherein the blood treatment device is a dialyzer.

20. The method of claim 14, wherein the regulating includes a net transfer of fluid responsively to both the one or more control parameters and a predefined ultrafiltration rate, such that a net flow from said blood treatment device through said first fluid lines, equal to said predefined ultrafiltration rate, is established.

* * * * *